US012716901B2

(12) United States Patent
Peng et al.

(10) Patent No.: US 12,716,901 B2
(45) Date of Patent: Aug. 25, 2026

(54) DETECTION OF ALZHEIMER'S DISEASE USING SPECIFIC BIOMARKERS

(71) Applicant: St. Jude Children's Research Hospital, Memphis, TN (US)

(72) Inventors: Junmin Peng, Memphis, TN (US); Hong Wang, Memphis, TN (US); Kaushik Kumar Dey, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 744 days.

(21) Appl. No.: 17/999,165

(22) PCT Filed: May 19, 2021

(86) PCT No.: PCT/IB2021/054339
§ 371 (c)(1),
(2) Date: Nov. 17, 2022

(87) PCT Pub. No.: WO2021/234607
PCT Pub. Date: Nov. 25, 2021

(65) Prior Publication Data

US 2023/0088509 A1 Mar. 23, 2023

Related U.S. Application Data

(60) Provisional application No. 63/032,047, filed on May 29, 2020, provisional application No. 63/027,697, filed on May 20, 2020.

(51) Int. Cl.
*G01N 33/68* (2006.01)

(52) U.S. Cl.
CPC ..... *G01N 33/6896* (2013.01); *G01N 2800/52* (2013.01); *G01N 2800/60* (2013.01)

(58) Field of Classification Search
CPC ........... A61K 45/06; G01N 2333/9015; G01N 2800/50; G01N 2800/52; G01N 2800/60;
(Continued)

(56) References Cited

U.S. PATENT DOCUMENTS

2004/0226056 A1* 11/2004 Roch .................. G01N 33/6896 800/12
2005/0260697 A1* 11/2005 Wang ................. G01N 33/6896 435/23

(Continued)

FOREIGN PATENT DOCUMENTS

EP 3 077 533 A1 10/2016
WO WO-2015082721 A1 * 6/2015 ........... C12Q 1/6883
WO WO 2018/111099 A1 6/2018

OTHER PUBLICATIONS

Hondius, D., et al., "Proteomics analysis identifies new markers associated with capillary cerebral amyloid angiopathy in Alzheimer's disease," *Acta Neuropathologica Communications,* 2018, vol. 6(1), pp. 1-19.

(Continued)

*Primary Examiner* — Jennifer Wecker
(74) *Attorney, Agent, or Firm* — Womble Bond Dickinson (US) LLP

(57) ABSTRACT

This disclosure relates to compositions and methods of diagnosing neurodegenerative disease by analyzing protein expression profiles in a subject.

20 Claims, 20 Drawing Sheets

(58) Field of Classification Search
CPC .. G01N 33/6848; G01N 33/6896; A61P 25/28
See application file for complete search history.

(56) References Cited

U.S. PATENT DOCUMENTS

2007/0042437 A1* 2/2007 Wands .................. A61K 38/28 514/342
2010/0124756 A1* 5/2010 Ray .................... G01N 33/6896 435/287.9
2014/0045713 A1* 2/2014 Everett ............. G01N 33/6896 506/18
2014/0142095 A1* 5/2014 Cortopassi ............. A61P 25/00 514/547
2014/0303041 A1* 10/2014 Hayes .................... C07K 16/18 506/18
2015/0119278 A1* 4/2015 Goetzl .............. G01N 33/6896 435/7.1
2015/0268252 A1* 9/2015 Svetlov ............. G01N 33/6896 435/7.1
2016/0041153 A1* 2/2016 Brown ............... G01N 33/5308 436/501
2016/0333063 A1* 11/2016 Hyman ................... A61P 25/28
2017/0292963 A1* 10/2017 Worley .............. G01N 33/6896
2018/0340945 A1* 11/2018 Mitsuhashi ............ A61P 35/00
2019/0219578 A1* 7/2019 Mitsuhashi .......... G01N 33/553
2019/0249147 A1* 8/2019 Davila ................ C12N 5/0697
2021/0311076 A1* 10/2021 Kipnis .................. A61B 5/055

OTHER PUBLICATIONS

Rahman, R., et al., "Common molecular biomarker signatures in blood and brain of Alzheimer's disease," 2018, *bioRxiv,* pp. 1-19—abstract.

Ramirez, A., et al., "SUCLG2 identified as both a determinator of CSF Aβ1-42 levels and an attenuator of cognitive decline in Alzheimer's disease," *Human Molecular Genetics,* 2014, vol. 23(24), pp. 1-15.

* cited by examiner

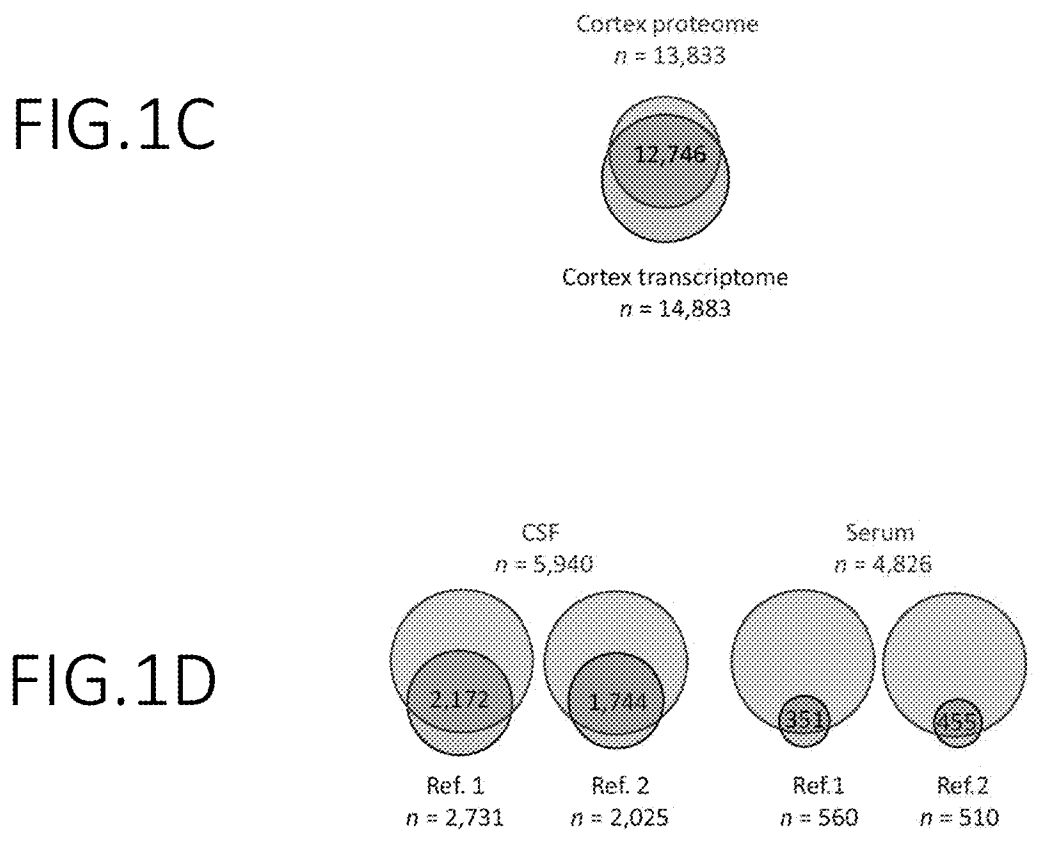

Cortex proteome
$n$ = 13,833
12,746
Cortex transcriptome
$n$ = 14,883

FIG.1C

CSF
$n$ = 5,940
2,172
Ref. 1
$n$ = 2,731
1,788
Ref. 2
$n$ = 2,025
Serum
$n$ = 4,826
351
Ref.1
$n$ = 560
455
Ref.2
$n$ = 510

FIG.1D

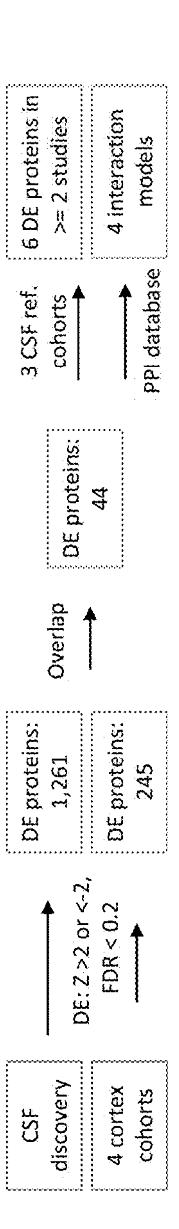
FIG.3A
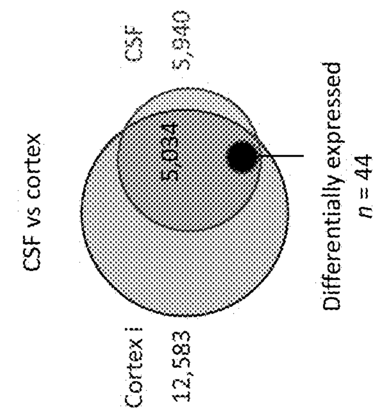
FIG.3B
TGFB2
IGFBP5
SLC5A3
HTRA1
SMOC1
C1QTNF5
OLFML3
SPON1
GPNM8
SLIT2
CTHRC1
Abi3
MDK
FAM19A5
CAMKK2
SGTB
CAMK4
BBOX1
DPYD
S100A4
All three studies
Overlap with study 1
Overlap with study 2
This study only
CSF Z value (AD vs Ctl)
Cortex Z value (AD vs Ctl)
5
0
−5
−10
0
10
20
30
FIG.3C HTRA1
Cortex 1
P = 8.9E-4
Cortex 2
P = 3.0E-8
CSF
P = 1.9E-2
CAMK4
Cortex 1
P = 8.9E-4
Cortex 2
P = 8.6E-2
CSF
P = 5.1E-2
S100A4
Cortex 1
P = 3.1E-6
Cortex 2
P = 6.2E-3
CSF
P = 6.7E-3
SLC5A3
Cortex 1
P = 1.0E-3
Cortex 2
P = 6.3E-4
CSF
P = 8.6E-3
CAMKK2
Cortex 1
P = 9.6E-4
Cortex 2
P = 1.3E-4
CSF
P = 1.9E-2
BBOX1
Cortex 1
P = 5.0E-4
Cortex 2
P = 8.9E-7
CSF
P = 1.2E-2
TMT intensity ($log_2$)
Ctl MCI AD
Ctl AD

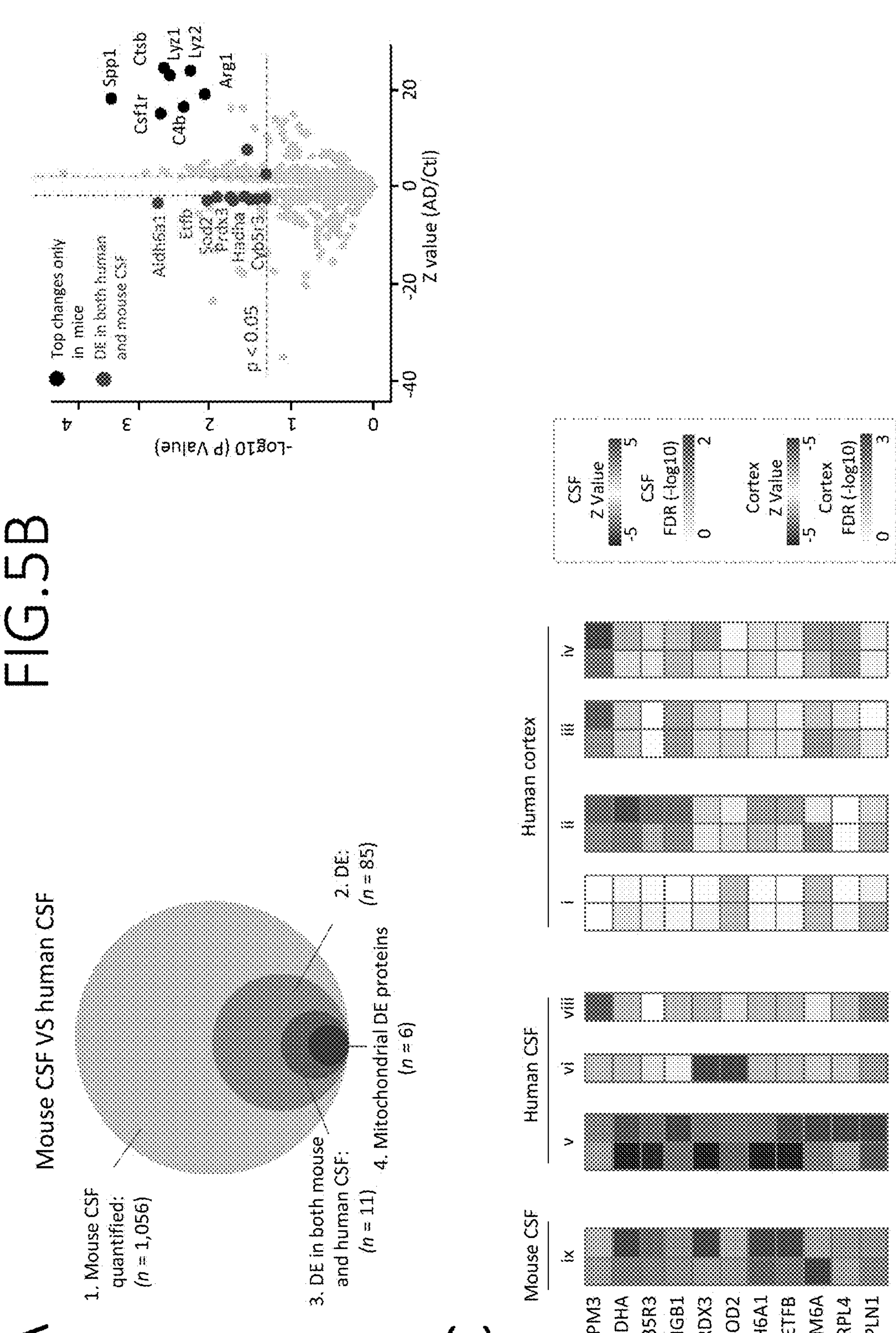
FIG.5A
Mouse CSF VS human CSF
1. Mouse CSF quantified: (n = 1,056)
2. DE: (n = 85)
3. DE in both mouse and human CSF: (n = 11)
4. Mitochondrial DE proteins (n = 6)
FIG.5B
Top changes only in mice
DE in both human and mouse CSF
p < 0.05
Spp1
Ctsb
Lyz1
Lyz2
Csf1r
Arg1
C4b
Aldh6a1
Etfb
Sod2
Prdx3
Hadha
Cyb5r3
-Log10 (P Value)
Z value (AD/Ctl)
FIG.5C
Mouse CSF
Human CSF
Human cortex
ix
v
vi
viii
i
ii
iii
iv
TPM3
HADHA
CYB5R3
HMGB1
PRDX3
SOD2
ALDH6A1
ETFB
GPM6A
RPL4
HAPLN1
CSF Z Value
CSF FDR (-log10)
Cortex Z Value
Cortex FDR (-log10)

FIG.5D
FIG.5E
HADHA
CYB5R3
$P$ = 5.7E-05
$P$ = 2.6E-05
$P$ = 2.2E-02
$P$ = 4.4E-04
$P$ = 8.0E-04
$P$ = 3.1E-02

C4B
SPP1
Human cortex
$P$ = 9.8E-07
Human CSF
$P$ = 2.5E-01
Mouse CSF
$P$ = 4.9E-03
Human cortex
$P$ = 6.8E-02
Human CSF
$P$ = 3.7E-01
Mouse CSF
$P$ = 6.4E-04
TMT intensity ($log_2$)
Ctl
AD Human serum
Top changes only in serum
Mito. DE in human CSF & serum, and in mouse CSF
GGT1
PIANP
SOD2
ETF6
ALDH6A1
PRDX3
FRMD7
ANO2
REV3L
p < 0.05
-Log10 (P Value)
Z value (AD/Ctl)
0
1
2
3
−10
0
10

Serum VS CSF VS cortex
1. Serum quantified: (n = 4,826)
2. DE: (n = 396)
3. DE in serum and CSF: (n = 107)
4. DE in serum and cortex: (n = 94)
5. DE in serum, CSF, and cortex: (n = 37)
6. Mito. DE in serum, CSF, and cortex (n = 22)

FIG.7A

| Gene name | Selected peptides | Discovery: Log2(AD/Ctl) | Validation: Log2(AD/Ctl) ± SEM |
|---|---|---|---|
| AK2 | AVLLGPPGAGK | -1.12 | -1.02 ± 0.37 |
| PCK2 | ETPIGLVPK | -1.36 | -1.34 ± 0.38 |

FIG. 9

| GN | Category | Protein Accession | Annotation | Brain Tissu | Subcellular | AD genes | Serum_Banner Sun | | | | PrecisionMed | | | Brain Tissue | | | CSF | | |
|---|---|---|---|---|---|---|---|---|---|---|---|---|---|---|---|---|---|---|---|
| | | | | | | | PSM | logFC | P Value | adj.P Val | PSM | logFC_ADv | P_ADvsCtl | PSM | Median of log2(AD/Ctl) | BH FDR | PSM | Median of | BH FDR |
| NPTX2 | Serum + Br | sp\|P47972 | Neuronal p | Brain eleva | #N/A | #N/A | 17 | -0.27 | 3.9E-02 | 3.8E-01 | 17 | 0.17 | 5.0E-01 | 43 | -1.03 | 4.4E-22 | 69 | -0.32 | 7.3E-04 |
| OLFM1 | Serum + Br | sp\|Q99784 | Noelin OS= | Brain enric | Nucleoplas | #N/A | 97 | -0.56 | 2.2E-03 | 1.3E-01 | 97 | -0.06 | 7.3E-01 | 131 | -0.41 | 9.7E-18 | 67 | 0.01 | 2.6E-01 |
| NGEF | Serum | sp\|Q8N5V | Ephexin-1 | Brain eleva | Plasma me | #N/A | 10 | -0.42 | 3.8E-02 | 3.0E-01 | 10 | -0.25 | 3.9E-01 | 97 | -0.31 | 1.2E-12 | #N/A | #N/A | #N/A |
| DGKG | Serum | sp\|P49619 | Diacylglyce | Brain eleva | Vesicles,Pl | #N/A | 3 | 0.57 | 2.1E-02 | 2.4E-01 | 3 | -0.09 | 8.3E-01 | 305 | 0.30 | 6.3E-08 | #N/A | #N/A | #N/A |
| SLC6A1 | Serum | sp\|P30531 | Sodium- ar | Brain eleva | #N/A | #N/A | 9 | -0.55 | 4.6E-02 | 3.3E-01 | 9 | 0.01 | 9.9E-01 | 104 | 0.03 | 3.0E-01 | 17 | -0.59 | 1.8E-02 |
| GRIN1 | Serum | sp\|Q05586 | Glutamate | Brain enric | #N/A | #N/A | 3 | -0.62 | 4.5E-02 | 3.2E-01 | 3 | -1.24 | 7.5E-02 | 149 | -0.27 | 1.7E-05 | #N/A | #N/A | #N/A |
| APOC2 | Serum | sp\|P02655 | Apolipopro | #N/A | #N/A | PMID:3134 | 848 | -0.46 | 1.3E-02 | 3.1E-01 | 848 | -0.39 | 2.2E-01 | 24 | -0.04 | 1.0E+00 | 57 | -1.07 | 1.4E-02 |
| SDHA | Serum | sp\|P31040 | Succinate c | #N/A | Nucleoli,M | #N/A | 9 | -0.42 | 1.7E-03 | 1.1E-01 | 9 | -0.15 | 5.6E-01 | 725 | -0.13 | 5.5E-07 | 87 | -0.96 | 7.1E-04 |
| ECI1 | Serum | sp\|P42126 | Enoyl-CoA | #N/A | Mitochond | #N/A | 29 | -0.49 | 3.0E-02 | 2.7E-01 | 29 | -0.09 | 7.1E-01 | 59 | 0.06 | 6.0E-02 | 39 | -0.86 | 5.1E-03 |
| HSPA9 | Serum | sp\|P38646 | Stress-70 p | #N/A | Mitochond | #N/A | 39 | -0.53 | 5.0E-03 | 1.6E-01 | 39 | 0.08 | 6.9E-01 | 1014 | -0.02 | 7.2E-01 | 208 | -0.62 | 1.9E-02 |
| ETFB | Serum | sp\|P38117 | Electron tr | #N/A | Mitochond | #N/A | 44 | -0.56 | 2.9E-02 | 2.7E-01 | 44 | -0.17 | 5.3E-01 | 364 | 0.03 | 3.9E-01 | 77 | -1.03 | 1.4E-02 |
| MYL3 | Serum | sp\|P08590 | Myosin ligh | #N/A | Nucleoli,M | #N/A | 77 | 0.86 | 5.9E-05 | 5.0E-02 | 77 | 0.28 | 4.2E-01 | 18 | 0.06 | 8.1E-02 | 23 | 0.23 | 5.8E-01 |
| MAPT | CSF + Brain | sp\|P10636 | Microtubul | Brain eleva | Nuclear sp | doi:https:/ | #N/A | #N/A | #N/A | #N/A | #N/A | #N/A | #N/A | 1134 | 0.48 | 2.1E-16 | 226 | 1.01 | 1.2E-23 |
| SMOC1 | CSF + Brain | sp\|Q9H4F8 | SPARC-rela | Brain eleva | #N/A | #N/A | 23 | -0.17 | 7.5E-01 | 6.1E-01 | 23 | 0.05 | 7.7E-01 | 47 | 1.20 | 3.9E-31 | 96 | 0.35 | 2.0E-12 |
| VGF | Brain | sp\|O15240 | Neurosecr | Brain eleva | #N/A | #N/A | #N/A | #N/A | #N/A | #N/A | #N/A | #N/A | #N/A | 197 | -0.62 | 3.0E-21 | 373 | -0.17 | 5.1E-03 |
| GPNMB | Brain | sp\|Q14956 | Transmem | #N/A | #N/A | #N/A | 27 | 0.00 | 1.0E+00 | 1.0E+00 | 27 | -0.04 | 8.9E-01 | 13 | 0.96 | 2.1E-17 | 39 | 0.28 | 1.1E-02 |
| RPH3A | Brain | sp\|Q9Y2J0 | Rabphilin-3 | Brain eleva | 0 | #N/A | #N/A | #N/A | #N/A | #N/A | #N/A | #N/A | #N/A | 367 | -0.48 | 1.4E-16 | 30 | -0.56 | 1.5E-02 |
| HSPB1 | Brain | sp\|P04792 | Heat shock | #N/A | Plasma me | #N/A | 56 | -0.04 | 8.2E-01 | 9.4E-01 | 56 | 0.53 | 3.0E-01 | 103 | 0.71 | 3.5E-19 | 151 | 0.14 | 9.9E-02 |
| MDK | Brain | sp\|P21741 | Midkine | #N/A | #N/A | #N/A | #N/A | #N/A | #N/A | #N/A | #N/A | #N/A | #N/A | 39 | 2.56 | 2.8E-33 | 22 | -0.10 | 3.3E-01 |
| CD109 | Brain | sp\|Q6YHK3 | CD109 anti | #N/A | #N/A | #N/A | 109 | -0.18 | 7.8E-02 | 3.9E-01 | 109 | -0.10 | 5.9E-01 | 115 | 0.57 | 2.1E-16 | 397 | 0.07 | 4.6E-01 |
| ICAM1 | Brain | sp\|P05362 | Intercellula | #N/A | #N/A | #N/A | 83 | 0.12 | 4.3E-01 | 7.7E-01 | 83 | 0.18 | 3.7E-01 | 58 | 1.08 | 2.2E-25 | 60 | -0.07 | 4.7E-01 |
| CTHRC1 | Brain | sp\|Q96CG8 | Collagen tr | #N/A | Nucleoplas | #N/A | #N/A | #N/A | #N/A | #N/A | #N/A | #N/A | #N/A | 12 | 1.35 | 2.4E-24 | 17 | -0.05 | 5.9E-01 |
| NTN1 | Brain | sp\|O95631 | Netrin-1 | #N/A | 0 | #N/A | #N/A | #N/A | #N/A | #N/A | #N/A | #N/A | #N/A | 34 | 1.84 | 7.2E-23 | #N/A | #N/A | #N/A |
| APP (Aβ) | Brain | cu\|P05067 | Amyloid be | #N/A | #N/A | #N/A | #N/A | #N/A | #N/A | #N/A | #N/A | #N/A | #N/A | 35 | 2.54 | 1.2E-19 | #N/A | #N/A | #N/A |
| CHI3L1 | CSF | sp\|P36222 | Chitinase-3 | #N/A | Golgi appa | #N/A | 136 | -0.06 | 7.7E-01 | 9.1E-01 | 136 | 0.48 | 3.2E-01 | 30 | 0.24 | 5.6E-02 | 347 | 0.39 | 9.6E-08 |
| ENO2 | CSF | sp\|P09104 | Gamma-en | Brain enric | Plasma me | #N/A | 33 | -0.30 | 3.0E-01 | 3.9E-01 | 33 | 0.98 | 3.3E-02 | 3393 | -0.01 | 7.4E-02 | 386 | 0.27 | 7.7E-08 |
| SOD1 | CSF | sp\|P00441 | Superoxide | #N/A | Nucleoplas | #N/A | 124 | -0.10 | 7.5E-01 | 9.2E-01 | 124 | 0.58 | 2.0E-01 | 194 | 0.03 | 1.0E-02 | 578 | 0.19 | 1.0E-09 |
| MDH1 | CSF | sp\|P40925 | Isoform 3 | #N/A | Centrosom | #N/A | 188 | 0.17 | 5.4E-01 | 8.2E-01 | 188 | 0.64 | 1.1E-01 | 1050 | 0.04 | 5.6E-01 | 814 | 0.28 | 4.3E-10 |
| PGAM1 | CSF | sp\|P18669 | Phosphogl | #N/A | Nucleoplas | #N/A | 132 | 0.03 | 8.8E-01 | 9.6E-01 | 132 | 0.48 | 4.4E-02 | 734 | 0.62 | 7.7E-01 | 836 | 0.32 | 9.9E-11 |
| LDHA | CSF | sp\|P00338 | L-lactate d | #N/A | Vesicles,Cy | #N/A | 435 | 0.05 | 8.3E-01 | 9.5E-01 | 435 | 0.33 | 1.4E-01 | 610 | -0.13 | 5.4E-04 | 499 | 0.45 | 1.1E-13 |
| GOT1 | CSF | sp\|P17174 | Aspartate a | #N/A | Nucleoplas | #N/A | 397 | -0.12 | 6.0E-01 | 8.5E-01 | 397 | 0.26 | 2.8E-01 | 826 | -0.02 | 7.0E-03 | 658 | 0.18 | 1.3E-13 |
| GDA | CSF | sp\|Q9Y2T3 | Isoform 3 c | Brain eleva | Nucleoplas | #N/A | 31 | -0.04 | 8.5E-01 | 9.5E-01 | 31 | 0.12 | 5.1E-01 | 863 | 0.01 | 3.7E-01 | 174 | 0.33 | 5.5E-17 |
| YWHAZ | CSF | sp\|P63104 | 14-3-3 pro | #N/A | Nucleoplas | #N/A | 231 | -0.25 | 3.0E-01 | 6.9E-01 | 231 | 0.60 | 5.9E-02 | 1135 | -0.02 | 2.3E-03 | 728 | 0.41 | 3.9E-19 |
| ALDOA | CSF | sp\|P04075 | Fructose-b | #N/A | Cytosol | #N/A | 333 | -0.02 | 9.3E-01 | 9.8E-01 | 333 | 0.90 | 9.7E-02 | 3241 | -0.05 | 2.7E-02 | 1729 | 0.39 | 4.3E-22 |
| YWHAG | CSF | sp\|P61981 | 14-3-3 pro | Brain eleva | Nucleoplas | #N/A | 157 | -0.20 | 3.6E-01 | 6.9E-01 | 157 | 0.44 | 1.2E-01 | 806 | -0.03 | 7.0E-04 | 387 | 0.75 | 3.8E-20 |
| PKM | CSF | cu\|uc010u | Pyruvate ki | #N/A | Cytosol | #N/A | 304 | -0.08 | 8.2E-01 | 9.6E-01 | 304 | 0.32 | 2.3E-01 | 3295 | -0.04 | 4.1E-01 | 3254 | 0.44 | 5.3E-21 |

DETECTION OF ALZHEIMER'S DISEASE USING SPECIFIC BIOMARKERS

CROSS-REFERENCE TO RELATED APPLICATIONS

This application is a national stage filing under 35 U.S.C. 371 of International Application No. PCT/IB2021/054339, filed May 19, 2021, which was published by the International Bureau in English on Nov. 25, 2021, which international application claims priority to U.S. Provisional Application No. 63/027,697, filed May 20, 2020, and U.S. Provisional Application No. 63/032,047, filed May 29, 2020, each of which is hereby incorporated in its entirety by reference herein.

STATEMENT OF FEDERALLY SPONSORED RESEARCH OR DEVELOPMENT

This invention was made with government support under grant number AG053987 awarded by the National Institutes of Health. The government has certain rights in the invention.

BACKGROUND

Alzheimer's disease (AD), the most common cause of dementia, affects more than 5 million Americans and an estimated 47 million individuals worldwide (Alzheimer's Assoc., *Alzheimer's Dement.* 12(4): p. 459-509 (2016)). AD is a progressive neurodegenerative brain disorder clinically characterized by extracellular amyloid plaque deposition, intracellular neurofibrillary tangle growth, memory and cognitive impairments. Traditionally, AD is diagnosed by assessing a patient's symptoms, memory and results of behavior tests, and can be confirmed by post-mortem brain pathologies, and also, more recently, using brain imaging technologies of these pathologies (McKhann, G. M., et al., *Alzheimer's Dement.* 7(3): p. 263-9 (2011)). Techniques such as structural magnetic resonance imaging (MM), and molecular imaging of deposited Aβ and tau proteins using positron emission tomography (PET) are highly accurate in detecting the presence of pathophysiological and neuropathological changes of AD and are useful in the drug development, but their high cost and insufficient accessibility are significant limitations (Sperling, R. A., et al., *Alzheimer's Dement.* 7(3): p. 280-92 (2011)). Proteomic profiling of human specimens is largely achieved using modern mass spectrometry (MS), however, compared with the analysis of human cell cultures or solid tissues, comprehensive proteomic analysis of human CSF and blood is challenging because individual protein concentration spans a large dynamic range of at least 10 orders of magnitude. Although a large number of protein biomarker candidates have been reported using the MS analysis, the candidates identified using the MS analysis are not reliably indicative of a given disease state, at least due to the inability to successfully reproduce these data across different laboratories, across distinct platforms and/or across indifferent independent cohorts. As such, there remains a need for compositions and methods of identifying biomarkers that systematically reflect AD pathogenesis for diagnosing and treating patients with AD.

SUMMARY OF THE INVENTION

This disclosure relates to compositions and methods for diagnosing neurodegenerative disease by analyzing protein (and/or nucleic acid, e.g., RNA) expression profiles in a subject. In certain embodiments, the present disclosure describes the diagnosis of Alzheimer's disease by detecting, analyzing and/or the identification changes in protein expression profiles as described herein. In other embodiments, the present disclosure describes monitoring the efficacy of a treatment for Alzheimer's disease by detecting, analyzing and/or the identification changes in protein expression profiles as described herein.

Accordingly, in a first aspect, the disclosure features a method for determining whether a subject has or is at risk of developing Alzheimer's disease comprising contacting a biological sample from the subject with a reagent for assaying the level of at least one signature protein selected from one or more of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3, detecting the amount of the at least one signature protein in the biological sample using the reagent, comparing the level of the at least one signature protein from the biological sample to the level of the at least one signature protein from a control sample, and determining whether the level of the at least one signature protein in the biological sample is an equivalent level, an increased level or a decreased level of the at least one signature protein compared to the control sample, wherein an increased level or a decreased level of the at least one signature protein in the biological sample relative to the level of the at least one signature protein from the control sample indicates that the subject has or is at risk of developing Alzheimer's disease.

In another aspect, the disclosure features a method of monitoring the progression of Alzheimer's disease in a subject comprising contacting a biological sample from the subject with a reagent for assaying for the level of at least one signature protein selected from one or more of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3, measuring the amount of the at least one signature protein in the biological sample as compared to a control sample, wherein an increased or a decreased level of the at least one signature protein relative to the control sample indicates progression of Alzheimer's disease in the subject.

In another aspect, the disclosure features a method of treatment of Alzheimer's disease comprising contacting a biological sample from the subject with a reagent for assaying for the level of at least one signature protein selected from one or more of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3, measuring the amount of the at least one signature protein in the biological sample as compared to a control sample, wherein an increased or a decreased level of the at least one signature protein relative to the control sample indicates progression of Alzheimer's disease in said subject, and treating said subject having a progression of Alzheimer's disease.

In certain embodiments, an increased level of at least one signature protein, at least two signature proteins, at least three signature proteins, at least four signature proteins, at least five signature proteins, at least six signature proteins, at least seven signature proteins, at least eight signature proteins, at least nine signature proteins, at least ten signature proteins, or at least eleven signature proteins indicates the subject has or is at risk of developing Alzheimer's disease or indicates a progression of Alzheimer's disease in said subject. In other embodiments, an increased level of at least twelve signature protein, at least thirteen signature proteins, at least fourteen signature proteins, at least fifteen signature proteins, at least sixteen signature proteins, at least seventeen signature proteins, at least eighteen signature proteins, at least nineteen signature proteins, at least twenty signature proteins, at least twenty-one signature proteins, or at least twenty-two signature proteins, at least twenty-three signature proteins, at least twenty-four signature proteins, at least twenty-five signature proteins, at least twenty-six signature proteins, at least twenty-seven signature proteins, at least twenty-eight signature proteins, at least twenty-nine signature proteins, indicates the subject has or is at risk of developing Alzheimer's disease or indicates a progression of Alzheimer's disease in said subject. In some embodiments, the signature protein includes at least one signature protein is selected from the group consisting of SLIT2, SPON1, GPNMB, C1QTNF5, OLFML3, SMOC1, TAU, GFAP, SUCLG2, PRDX3, and NTN1.

In certain embodiments, a decreased level of at least one signature protein, at least two signature proteins, at least three signature proteins, at least for signature proteins, at least five signature proteins, at least six signature proteins, at least seven signature proteins, at least eight signature proteins, or at least nine signature proteins, at least ten signature proteins, or at least eleven signature proteins, at least twelve signature protein, at least thirteen signature proteins, at least fourteen signature proteins, at least fifteen signature proteins, at least sixteen signature proteins, at least seventeen signature proteins, at least eighteen signature proteins, at least nineteen signature proteins, at least twenty signature proteins, at least twenty-one signature proteins, or at least twenty-two signature proteins, at least twenty-three signature proteins, at least twenty-four signature proteins, at least twenty-five signature proteins, at least twenty-six signature proteins, at least twenty-seven signature proteins, at least twenty-eight signature proteins, at least twenty-nine signature proteins indicates the subject has or is at risk of developing Alzheimer's disease or indicates a progression of Alzheimer's disease in said subject. In some embodiments, the signature protein includes at least one signature protein selected from the group consisting of SOD2, PRDX3, ALDH6A1, ETFB, HADHA, CYB5R3, CTHRC1, GFAP and OLFM3.

In another aspect, the disclosure features a method for determining whether a subject has or is at risk of developing Alzheimer's disease, comprising contacting a biological sample from the subject with a reagent for assaying the level of at least one signature protein selected from one or more of ALDH6A1, ETFB, SOD2, PRDX3, CTHRC1, GFAP, OLFM3, NPTX2, OLFM1, NGEF, DGKG, SLC6A1, GRIN1, APOC2, SDHA, ECI1, HSPA9, and MYL3, detecting the amount of the at least one signature protein in the biological sample using the reagent, comparing the level of the at least one signature protein from the biological sample to the level of the at least one signature protein from a control sample, and determining whether the level of the at least one signature protein in the biological sample is an equivalent level, an increased level or a decreased level of the at least one signature protein compared to the control sample, wherein an increased level or a decreased level of the at least one signature protein in the biological sample relative to the level of the at least one signature protein from the control sample indicates that the subject has or is at risk of developing Alzheimer's disease.

In another aspect, the disclosure features a method of monitoring the progression of Alzheimer's disease in a subject, said method comprising contacting a biological sample from the subject with a reagent for assaying for the level of at least one signature protein selected from one or more of ALDH6A1, ETFB, SOD2, PRDX3, CTHRC1, GFAP, OLFM3, NPTX2, OLFM1, NGEF, DGKG, SLC6A1, GRIN1, APOC2, SDHA, ECI1, HSPA9, and MYL3, measuring the amount of the at least one signature protein in the biological sample as compared to a control sample, wherein an increased or a decreased level of the at least one signature protein relative to the control sample indicates progression of Alzheimer's disease in the subject.

In another aspect, the disclosure features a method of treatment of Alzheimer's disease comprising contacting a biological sample from the subject with a reagent for assaying for the level of at least one signature protein selected from one or more of ALDH6A1, ETFB, SOD2, PRDX3, CTHRC1, GFAP, OLFM3, NPTX2, OLFM1, NGEF, DGKG, SLC6A1, GRIN1, APOC2, SDHA, ECI1, HSPA9, and MYL3, measuring the amount of the at least one signature protein in the biological sample as compared to a control sample, wherein an increased or a decreased level of the at least one signature protein relative to the control sample indicates progression of Alzheimer's disease in said subject, and treating said subject having a progression of Alzheimer's disease.

In certain embodiments, an increased level of at least one signature protein, at least two signature proteins, at least three signature proteins, at least four signature proteins, at least five signature proteins, at least six signature proteins, at least seven signature proteins, at least eight signature proteins, at least nine signature proteins, at least ten signature proteins, or at least eleven signature proteins indicates the subject has or is at risk of developing Alzheimer's disease or indicates a progression of Alzheimer's disease in said subject. In other embodiments, an increased level of at least twelve signature protein, at least thirteen signature proteins, at least fourteen signature proteins, at least fifteen signature proteins, at least sixteen signature proteins, at least seventeen signature proteins, at least eighteen signature proteins, at least nineteen signature proteins, at least twenty signature proteins, at least twenty-one signature proteins, or at least twenty-two signature proteins, at least twenty-three signature proteins, at least twenty-four signature proteins, at least twenty-five signature proteins, at least twenty-six signature proteins, at least twenty-seven signature proteins, at least twenty-eight signature proteins, at least twenty-nine signature proteins, indicates the subject has or is at risk of developing Alzheimer's disease or indicates a progression of Alzheimer's disease in said subject. In some embodiments, the signature protein includes at least one signature protein is selected from the group consisting of SLIT2, SPON1, GPNMB, C1QTNF5, OLFML3, SMOC1, TAU, GFAP, SUCLG2, PRDX3, and NTN1.

In certain embodiments, a decreased level of at least one signature protein, at least two signature proteins, at least three signature proteins, at least for signature proteins, at least five signature proteins, at least six signature proteins, at least seven signature proteins, at least eight signature proteins, or at least nine signature proteins, at least ten signature proteins, or at least eleven signature proteins, at least twelve signature protein, at least thirteen signature proteins, at least fourteen signature proteins, at least fifteen signature proteins, at least sixteen signature proteins, at least seventeen signature proteins, at least eighteen signature proteins, at least nineteen signature proteins, at least twenty signature proteins, at least twenty-one signature proteins, or at least twenty-two signature proteins, at least twenty-three signature proteins, at least twenty-four signature proteins, at least twenty-five signature proteins, at least twenty-six signature proteins, at least twenty-seven signature proteins, at least twenty-eight signature proteins, at least twenty-nine signature proteins indicates the subject has or is at risk of developing Alzheimer's disease or indicates a progression of Alzheimer's disease in said subject. In some embodiments, the signature protein includes at least one signature protein selected from the group consisting of SOD2, PRDX3, ALDH6A1, ETFB, HADHA, CYB5R3, CTHRC1, GFAP and OLFM3.

In some embodiments, the biological sample comprises a blood sample, a serum sample, a plasma sample, a lymph sample, a urine sample, a saliva sample, a tear sample, a sweat sample, a semen sample, a vaginal sample, a bronchial sample, a mucosal sample, a cerebrospinal fluid (CSF) sample, or brain microdialysate. In other embodiments, the level of said at least one signature protein is measured or detected using an immunoassay, a western blot analysis, mass spectrometry, tandem mass (MS/MS) spectrometry, multiplexed tandem mass-tag, liquid chromatography (LC) fractionation, TOMAHAQ, a TMT-LC/LC/MS/MS platform, or an ultra-deep proteomic platform. In another embodiment, the reagent is a reagent useful for performing an immunoassay, a western blot analysis, a mass spectrometry analysis, a tandem mass (MS/MS) spectrometry analysis, a multiplexed tandem mass-tag analysis, a liquid chromatography (LC) fractionation analysis, a TOMAHAQ analysis, a TMT-LC/LC/MS/MS platform analysis, or an ultra-deep proteomic platform analysis. In another embodiment, the reagent comprises protein-sequence and protein-fragment-specific peptides, and where in the detecting or measuring comprises targeted quantitative mass spectrometry.

In certain embodiments, the method further comprises detecting levels of beta-amyloid in the brain of the subject, wherein the detecting is performed using structural imaging and assessing whether wherein the levels of beta-amyloid in the brain of the subject indicates (i) that the subject has or is at risk of developing Alzheimer's disease or (ii) efficacy of treatment. In yet another embodiment, the method further comprises administering a cognitive test to the subject, and assessing whether results of the cognitive test indicates (i) that the subject has or is at risk of developing Alzheimer's disease or (ii) efficacy of treatment. In certain embodiments, the treating comprises administering a therapeutically effective amount of an antagonist of at least one signature protein. In certain other embodiments, the antagonist is an antagonist of SMOC1, an antagonist of C1QTNF5, an antagonist of OLFML3, an antagonist of SLIT2, an antagonist of SPON1, an antagonist of GPNMB, an antagonist of TAU, an antagonist of GFAP, an antagonist of SUCLG2, an antagonist of PRDX3, an antagonist of NTN1, or any combination thereof. In one embodiment, the treating comprises administering a therapeutically effective amount of an agonist of at least one signature protein. In another embodiment, the agonist is an agonist of SOD2, an agonist of PRDX3, an agonist of ALDH6A1, an agonist of ETFB, an agonist of HADHA, an agonist of CYB5R3, an agonist of CTHRC1, an agonist of GFAP, an agonist of OLFM3, or any combination thereof. In certain embodiments, the treating comprises administering a therapeutically effective amount of an antagonist/agonist of SUCLG2, an antagonist/agonist of NTN1, an antagonist/agonist of C1QTNF5, an antagonist/agonist of OLFML3, an antagonist/agonist of SLIT2, an antagonist/agonist of SPON1, an antagonist/agonist of GPNMB, an antagonist/agonist of SOD2, an antagonist/agonist of PRDX3, an antagonist/agonist of ALDH6A1, an antagonist/agonist of ETFB, an antagonist/agonist of HADHA, an antagonist/agonist of CYB5R3, an antagonist/agonist of CTHRC1, an antagonist/agonist of OLFM3, an antagonist/agonist of SMOC1, an antagonist/agonist of TAU, an antagonist/agonist of GFAP, an antagonist/agonist of NPTX2, an antagonist/agonist of OLFM1, an antagonist/agonist of NGEF, an antagonist/agonist of DGKG, an antagonist/agonist of SLC6A1, an antagonist/agonist of GRIN1, an antagonist/agonist of APOC2, an antagonist/agonist of SDHA, an antagonist/agonist of ECI1, an antagonist/agonist of HSPA9, and an antagonist/agonist of MYL3, or any combination thereof.

In certain embodiments, the method further comprises administering an additional agent, wherein the additional agent is a cholinesterase inhibitor. In one embodiment, the cholinesterase inhibitor is Aricept, Exelon, and/or Razadyne.

In certain embodiments, the method further comprises administering an additional agent, wherein the additional agent is memantine.

In another aspect, the disclosure features a method of monitoring efficacy of an Alzheimer's disease treatment regimen in a human subject having Alzheimer's disease, comprising the steps of obtaining a first biological sample from the subject at a first time point; administering the treatment regimen to the subject; obtaining a second biological sample from the subject at a second time point; detecting levels of at least one signature protein selected from one or more of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3 in the first sample and detecting protein levels for the at least one signature protein in the second sample. In one embodiment, the method further comprises changing the treatment regimen when the levels of the at least one signature protein for the first sample are the same or nearly the same as the levels of at least one signature protein for the second sample. In one embodiment, the method further comprises repeating the treatment regimen when the levels of the at least one signature protein for the first sample are the same or nearly the same as the levels of the at least one signature protein for the second sample. In another embodiment, the method further comprises discontinuing the treatment regimen when the levels of the at least one signature protein of the second sample return to the levels of the at least one signature protein corresponding to a healthy individual. In one embodiment, the biological sample comprises a blood sample, a serum sample, a plasma sample, a lymph sample, a urine sample, a saliva sample, a tear sample, a sweat sample, a semen sample, a vaginal sample, a bronchial sample, a mucosal sample, a cerebrospinal fluid (CSF) sample, or brain microdialysate.

In another aspect, the disclosure features a composition comprising at least two (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or more) signature proteins useful for diagnosing, predicting, and/or monitoring Alzheimer's disease in a sample of a subject, wherein the at least two (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or more) signature proteins are selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3, or fragments, or variants thereof.

In another aspect, the disclosure features a composition comprising at least two (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or more) signature proteins useful for diagnosing, predicting, and/or monitoring Alzheimer's disease in a sample of a subject, wherein the at least two (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or more) signature proteins are selected from the group consisting of ALDH6A1, ETFB, SOD2, PRDX3, CTHRC1, GFAP, OLFM3, NPTX2, OLFM1, NGEF, DGKG, SLC6A1, GRIN1, APOC2, SDHA, ECI1, HSPA9, and MYL3, or fragments, or variants thereof.

In another aspect, the disclosure features a test panel comprising a composition comprising at least two (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or more) signature proteins useful for diagnosing, predicting, and/or monitoring Alzheimer's disease in a sample of a subject, wherein the at least two (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or more) signature proteins are selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3, or fragments, or variants thereof.

In another aspect, the disclosure features a test panel comprising a composition comprising at least two (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or more) signature proteins useful for diagnosing, predicting, and/or monitoring Alzheimer's disease in a sample of a subject, wherein the at least two (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or more) signature proteins are selected from the group consisting of ALDH6A1, ETFB, SOD2, PRDX3, CTHRC1, GFAP, OLFM3, NPTX2, OLFM1, NGEF, DGKG, SLC6A1, GRIN1, APOC2, SDHA, ECI1, HSPA9, and MYL3, or fragments, or variants thereof.

In some embodiments, the test panel has at least ten signature proteins. In some embodiments, the test panel has at least twelve signature proteins. In some embodiments, the test panel has at least fourteen signature proteins. In some embodiments, the test panel has at least fifteen or more signature proteins. In some embodiments, the test panel less than fifteen signature proteins. In some embodiments, the test panel less than fourteen signature proteins. In some embodiments, the test panel less than twelve signature proteins. In some embodiments, the test panel less than ten signature proteins. In some embodiments, the test panel less than eight signature proteins. In some embodiments, the test panel less than six signature proteins.

In another aspect, the disclosure features a kit or assay device comprising a test panel comprising a composition comprising at least two signature proteins useful for diagnosing, predicting, and/or monitoring Alzheimer's disease in a sample of a subject, wherein the at least two signature proteins are selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3, or fragments, or variants thereof.

In another aspect, the disclosure features a kit or assay device comprising a test panel comprising a composition comprising at least two signature proteins useful for diagnosing, predicting, and/or monitoring Alzheimer's disease in a sample of a subject, wherein the at least two signature proteins are selected from the group consisting of ALDH6A1, ETFB, SOD2, PRDX3, CTHRC1, GFAP, OLFM3, NPTX2, OLFM1, NGEF, DGKG, SLC6A1, GRIN1, APOC2, SDHA, ECI1, HSPA9, and MYL3, or fragments, or variants thereof.

In another aspect, the disclosure features a composition for use in the treatment of Alzheimer's disease, said use comprising contacting a biological sample from the subject with a reagent for assaying for the level of at least one signature protein selected from one or more of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3, measuring the amount of the at least one signature protein in the biological sample as compared to a control sample, wherein an increased or a decreased level of the at least one signature protein relative to the control sample indicates progression of Alzheimer's disease in said subject, and treating said subject having a progression of Alzheimer's disease. In some embodiments, an increased level of at least one signature protein, at least two signature proteins, at least three signature proteins, at least for signature proteins, at least five signature proteins, at least six signature proteins, at least seven signature proteins, at least eight signature proteins, at least nine signature proteins, at least ten signature proteins, or at least eleven signature proteins indicates the subject has or is at risk of developing Alzheimer's disease or indicates a progression of Alzheimer's disease in said subject. In some embodiments, the signature protein includes at least one signature protein is selected from the group consisting of SLIT2, SPON1, GPNMB, C1QTNF5, OLFML3, SMOC1, TAU, GFAP, SUCLG2, PRDX3, and NTN1. In another embodiment, a decreased level of at least one signature protein, at least two signature proteins, at least three signature proteins, at least for signature proteins, at least five signature proteins, at least six signature proteins, at least seven signature proteins, at least eight signature proteins, or at least nine signature proteins indicates the subject has or is at risk of developing Alzheimer's disease or indicates a progression of Alzheimer's disease in said subject. In another embodiment, the signature protein includes at least one signature protein selected from the group consisting of SOD2, PRDX3, ALDH6A1, ETFB, HADHA, CYB5R3, CTHRC1, GFAP and OLFM3. In some embodiments, the treating comprises administering a therapeutically effective amount of an antagonist of at least one signature protein. In other embodiments, the antagonist is an antagonist of SMOC1, an antagonist of C1QTNF5, an antagonist of OLFML3, an antagonist of SLIT2, an antagonist of SPON1, an antagonist of GPNMB, an antagonist of TAU, an antagonist of GFAP, an antagonist of SUCLG2, an antagonist of PRDX3, an antagonist of NTN1, or any combination thereof. In other embodiments, the treating comprises administering a therapeutically effective amount of an agonist of at least one signature protein. In yet other embodiments, the agonist is an agonist of SOD2, an agonist of PRDX3, an agonist of ALDH6A1, an agonist of ETFB, an agonist of HADHA, an agonist of CYB5R3, an agonist of CTHRC1, an agonist of GFAP, an agonist of OLFM3, or any combination thereof. In another embodiment, the treating comprises administering a therapeutically effective amount of an antagonist/agonist of SUCLG2, an antagonist/agonist of NTN1, an antagonist/agonist of C1QTNF5, an antagonist/agonist of OLFML3, an antagonist/agonist of SLIT2, an antagonist/agonist of SPON1, an antagonist/agonist of GPNMB, an antagonist/agonist of SOD2, an antagonist/agonist of PRDX3, an antagonist/agonist of ALDH6A1, an antagonist/agonist of ETFB, an antagonist/agonist of HADHA, an antagonist/agonist of CYB5R3, an antagonist/agonist of CTHRC1, an antagonist/agonist of OLFM3, an antagonist/agonist of SMOC1, an antagonist/agonist of TAU, an antagonist/agonist of GFAP, an antagonist/agonist of NPTX2, an antagonist/agonist of OLFM1, an antagonist/agonist of NGEF, an antagonist/agonist of DGKG, an antagonist/agonist of SLC6A1, an antagonist/agonist of GRIN1, an antagonist/agonist of APOC2, an antagonist/agonist of SDHA, an antagonist/agonist of ECI1, an antagonist/agonist of HSPA9, and an antagonist/agonist of MYL3, or any combination thereof. In some embodiments, the method further comprises administering an additional agent, wherein the additional agent is a cholinesterase inhibitor. In some embodiments, the cholinesterase inhibitor is Aricept, Exelon, and/or Razadyne. In some embodiments, the method further comprises administering an additional agent, wherein the additional agent is memantine.

BRIEF DESCRIPTION OF THE DRAWINGS

FIG. 1 depicts the comprehensive integration of ultra-deep cortex, CSF and serum proteome datasets for biomarker analyses in Alzheimer's disease. FIG. 1C shows the advanced tissue proteome profiling pipeline achieves ultra-deep proteome coverage in the cortex. The unique proteins quantified in the cortex discovery cohorts were combined and then compared to the cortex transcriptome with consensus normalized expression (NX) values >1 in the Human Protein Atlas database. FIG. 1D shows advanced biofluid proteome profiling platform achieves ultra-deep proteome coverage in the human CSF and the serum. The CSF proteome was compared to the two deepest MS-based CSF proteome studies in AD so far, Reference 1 (data vi, Higginbotham L, BioRxiv, 2019) and Reference 2 (data viii, Sathe G, Proteomics Clin Appl. 2019), similarly the serum proteome data was compared to the two recent MS-based AD serum protein biomarker studies, Reference 1 (Ashton N, Science Advances, 2019) and Reference 2 (Lan J, Journal of Proteome Research, 2018).

FIG. 2 shows that ultra-deep CSF proteome profiling identifies mitochondrial protein reduction in Alzheimer's disease.

FIG. 3 shows the integrated analysis of cortex and CSF proteomes identifies consistent CSF biomarkers in AD across independent studies. FIG. 3A depicts the scheme for the integration of the cortex and the CSF proteomes. FIG. 3B shows a Venn diagram depicting the overlap of quantified proteins in the cortex discovery cohort (data i) and the CSF discovery cohort (data v). FIG. 3C shows the integration of the cortex and the CSF proteomes identifies consistent CSF biomarkers in AD across independent studies. Proteins quantified in both the cortex and the CSF are plotted as a function of their Z score comparing AD to Ctl in cortex (x-axis) and their Z score comparing AD to Ctl in CSF (y-axis). 44 DE proteins with Z score difference >2 and FDR <0.2 in both proteomes are plotted in black. Proteins consistently showed up as AD biomarkers in all three independent CSF studies are labeled in red, proteins stood out in this study and reference study 1 (Higginbotham L, BioRxiv, 2019) are labeled in blue, and proteins described herein and in reference study 2 (Sathe G, Proteomics Clin Appl. 2019) are labeled in turquoise. Red dashed lines indicate Z value difference >2 in CSF and serum.

FIG. 4 shows the expression levels of reported and novel AD CSF biomarker candidates in the cortex and the CSF proteomes.

FIG. 5 shows the integration of the human and the mouse CSF proteomes identifies consistent mitochondrial protein decrease in Alzheimer's disease. FIG. 5A shows a summary of the DE analysis of mouse CSF proteome, and its integration with human CSF proteome. The analysis was performed in 4 steps. 1) 1,056 proteins were quantified in 6 5×FAD and 5 WT groups that were pooled from 32 mice. 2) 85 proteins were identified as DE proteins with a Z score difference >2 and p value <0.05. 3) 11 out of these 85 proteins are differentially expressed in both human and mouse CSF samples. 4) 6 out of these 11 DE proteins are mitochondrial proteins. FIG. 5B shows a volcano plot for the quantified mouse CSF proteome. The x-axis shows the Z score transformed log 2 fold changes comparing AD to Ctl. The y-axis shows the −log 10 p value. The top DE proteins in mice CSF are plotted in black and labeled. Proteins that are differentially expressed in both human and mouse CSF are plotted in red, and the mitochondrial proteins are further labeled. The red dashed lines indicate the DE cutoff of p value <0.05 and Z score difference >2. FIG. 5C shows a heatmap shows Z score, −log 10 FDR value or p value of the 11 DE proteins in the mouse CSF, the human CSF, and the human cortex proteomes.

FIG. 6 shows the integration of the CSF, the serum, and the cortex datasets identifies consistent mitochondrial signatures in Alzheimer's disease across proteomes.

FIG. 7 shows the integration of the protein rankings in individual datasets though order statistics prioritizes top AD signatures. FIG. 7A depicts the workflow for tiered integration of individual proteome ranking by order statistics. The rank of each individual dataset was integrated by discovery or reference cohorts separately first, and was then combined into the cortex, the CSF, or the serum ranking. The three ranks were then integrated into a final integrative ranking.

FIG. 8 shows the validation of MS discoveries by ELISA and TOMAHAQ assays.

FIG. 9 shows results from an analysis of serum protein biomarker candidates performed via serum, CSF, and brain cortex tissue proteomics integration.

DETAILED DESCRIPTION

I. Definitions

Figures 1A, 1B:
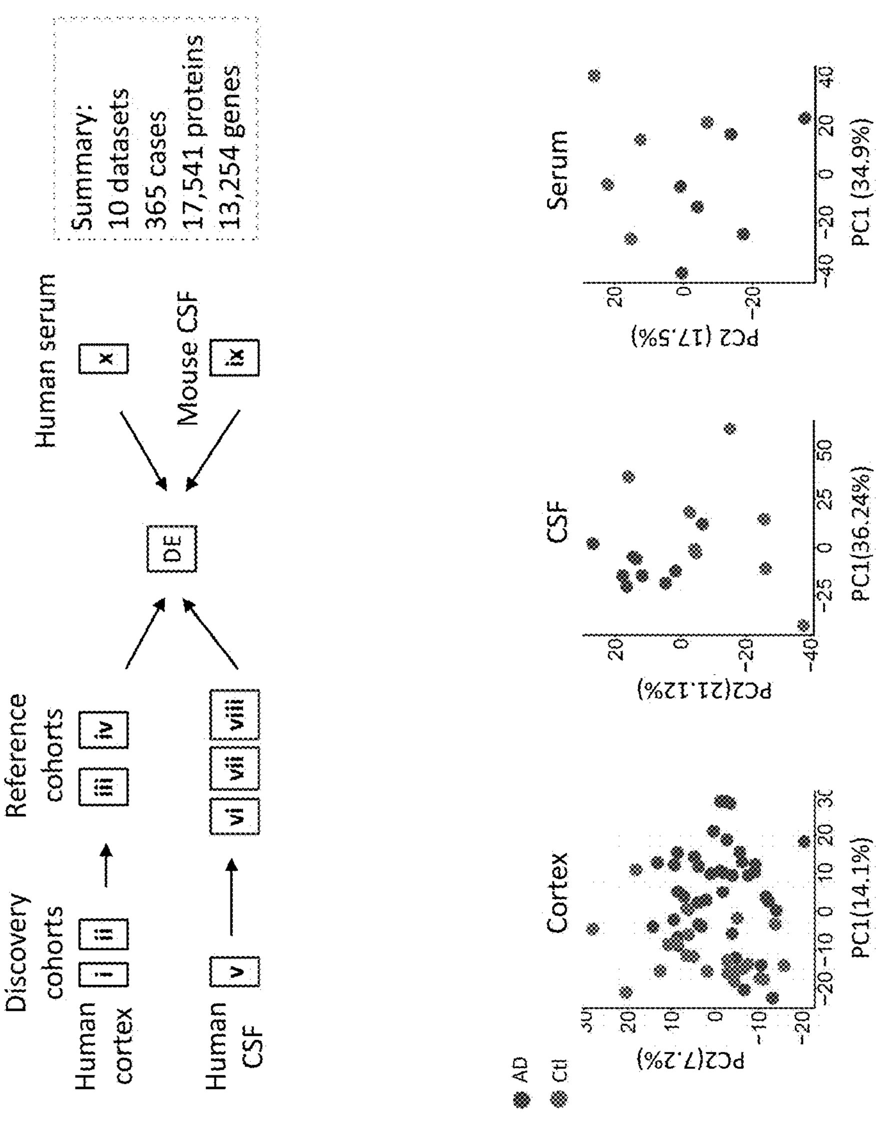
FIG. 1A depicts the workflow for data integration. The human brain cortex proteomes consist of 4 datasets including 2 discovery cohorts (data i and ii) that were validated by 2 reference cohorts (data iii and iv). The human cerebrospinal fluid (CSF) proteomes consist of 4 individual datasets including one discovery cohort (data v) that was validated by 3 reference cohorts (data vi, vii, viii). Differential expression (DE) of CSF proteome was carried out through LIMMA R package, and then integrated with cortex proteome. The human CSF proteome was compared with mouse CSF (data ix). Finally, the cortex and CSF proteomes were integrated with the serum proteome (data x).
FIG. 1B shows the principle component analyses (PCA) of discovery proteomes. Dot plots show two-dimensional principle component analyses of all quantified proteins in the representative discovery datasets including human cortex (ii), Human CSF (v), and human serum (x). Protein expression values of all datasets were log 2-transformed for PCA analyses.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, immunology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

"Subject" or "patient," as used interchangeably, refers either a human or non-human animal. In one embodiment, a subject is a human subject. In certain other embodiments, a subject is livestock, a rodent, a monkey or a domestic pet.

The term "sample" or "biological sample" as used herein refers to any biological or chemical mixture for use in the method of the disclosure. The sample can be a biological sample. The biological samples are generally derived from a patient, preferably as a bodily fluid (such as tumor tissue, lymph node, sputum, blood, bone marrow, cerebrospinal fluid, phlegm, saliva, or urine) or cell lysate. The cell lysate can be prepared from a tissue sample (e.g. a tissue sample obtained by biopsy), for example, a tissue sample (e.g. a tissue sample obtained by biopsy), blood, cerebrospinal fluid, phlegm, saliva, urine, or the sample can be cell lysate. In preferred examples, the sample is one or more of CSF, blood, blood plasma, serum, cells, a cellular extract, a cellular aspirate, tissues, a tissue sample, or a tissue biopsy.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that reduces symptoms and/or delays disease progression. Treatment also includes diminishment of the extent of the disease or condition; delay or slowing the progress of the disease or condition. Treatment does not require the complete amelioration of a symptom or disease and encompasses embodiments in which one reduces symptoms and/or underlying risk factors. "Treatment" can also mean prolonging survival as compared to expected survival if not receiving treatment.

The term "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

As used herein, the term "signature protein" refers to a protein that is associated with Alzheimer's disease, and/or with an increased or a decreased risk of Alzheimer's disease. In one embodiment, an increase in the level of a signature protein relative to a healthy control level, or a known standard control level indicates the subject has Alzheimer's disease or is at an increased risk of developing Alzheimer's disease. In another embodiment, a decrease in the level of a signature protein relative to a healthy control level, or a known standard control level indicates the subject has Alzheimer's disease or is at an increased risk of developing Alzheimer's disease. Accordingly, in one embodiment, a signature protein useful in the present disclosure, is any protein (or combination of proteins) the expression of which is regulated (up or down) in a subject with Alzheimer's disease, or in a subject at risk of developing Alzheimer's disease, when compared to a normal control, i.e., an unaffected (healthy) control subject (or known standard control level). In one embodiment, selected sets of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, or more of the signature proteins as disclosed herein can be used as end-points for rapid diagnostics or prognostics for determining whether a patient has Alzheimer's disease, or is at risk of developing Alzheimer's disease.

As used herein, the term “comparable level” refers to a level of a protein (e.g., a signature protein) that is substantially similar to the level of another, e.g., a healthy protein control level, or a known standard protein control level. In one embodiment, two proteins have a comparable level if the level of a first protein (e.g., a signature protein) is within one standard deviation of a second protein (e.g., a healthy control level, or a known standard control level). In another embodiment, two proteins have a comparable level if the level of a first protein (e.g., a signature protein) is within 20%, 15%, 10%, 9%, 8%, 7%, 6%, 5%, 4%, 3%, 2%, 1%, or less of the level of a second protein (e.g., a healthy control level, or a known standard control level).

As used herein, the term “expression” when used in connection with detecting the expression of a protein (e.g., a signature protein) of the present disclosure, can refer to detecting transcription of the gene encoding a signature protein, to detecting translation of the signature protein, and/or detecting the signature protein which results from metabolism of a larger protein. To detect expression of a signature protein refers to the act of actively determining whether a signature protein is expressed or not. To quantitate expression refers to the act of determining the level of the given signature protein, e.g., ng/ml. Detecting and/or quantitating expression can include determining whether the signature protein expression is upregulated as compared to a known standard level, downregulated as compared to a known standard level, or substantially unchanged as compared to a known standard level. Therefore, the step of quantitating and/or detecting expression does not require that expression of the signature protein actually is upregulated or downregulated, but rather, can also include detecting no expression of the signature protein or detecting that the expression of the signature protein has not changed or is not different (i.e., detecting no significant expression of the signature protein or no significant change in expression of the signature protein as compared to a control).

As used herein, the term “known standard level”, “known standard control level”, “reference level” or “control level” refers to an accepted or pre-determined level of a protein (e.g., a signature protein) which is used to compare the signature protein level derived from the biological sample of a subject. In one embodiment, when compared to the known standard level of a certain signature protein, deviation from the known standard level generally indicates either an improvement or deterioration in a disease state. In one embodiment, when compared to the known standard level of a certain signature protein, deviation from the known standard level generally indicates an increased or a decreased likelihood of disease progression in a subject. Alternatively, when compared to the known standard level of a certain signature protein, equivalence to the known standard level generally indicates confirmation of the disease activity, confirmation of a non-disease state, or, if the signature protein level of the subject is obtained following therapeutic treatment for the disease, failure of a therapy to improve a patient’s disease state. In one embodiment, the known standard level of a signature protein indicates an unaffected, i.e., non-disease, state of a subject who is not characterized as having Alzheimer’s disease.

The term “level” or “amount” of a protein (e.g., a signature protein), as used herein, refers to the measurable quantity of a protein (e.g., a signature protein). The amount may be either (a) an absolute amount as measured in molecules, moles or weight per unit volume or cells or (b) a relative amount, e.g., measured by densitometric analysis.

The term “therapeutically effective amount” refers to an amount which, when administered to a living subject, achieves a desired effect on the living subject. The exact amount will depend on the purpose of the treatment, and may be ascertainable by one skilled in the art using known techniques. As is known in the art, adjustments for systemic versus localized delivery, age, body weight, general health, sex, diet, time of administration, drug interaction and the severity of the condition may be necessary, and may be ascertainable with routine experimentation by those skilled in the art. For example, an effective amount of an agent described herein for administration to a living subject is an amount that prevents and/or treats Alzheimer’s disease. For example, for an antagonist or agonist of any one of the signature proteins disclosed herein, a therapeutically effective amount can be an amount that has been shown to provide an observable therapeutic benefit compared to baseline clinically observable signs and symptoms of Alzheimer’s disease.

II. Signature Proteins for Identifying Alzheimer’s Disease

The present disclosure is based, at least in part, on the discovery that certain signature proteins are associated with Alzheimer’s disease. As described in the Examples below, the disclosure provides signature proteins whose levels can be used to diagnose and/or predict whether a subject has, or is at risk of developing Alzheimer’s disease, and/or monitor the efficacy of an Alzheimer’s disease treatment regimen. Moreover, the signature proteins disclosed herein can incorporated into treatment regimens of Alzheimer’s disease.

Thus, in one embodiment, the present disclosure relates to signature proteins that are reliably associated with Alzheimer’s disease. These signature proteins may be used to determine whether a subject, e.g., with mild cognitive impairment, has, or is at risk of developing, Alzheimer’s disease. These signature proteins may also be used to monitor the therapeutic efficacy of an Alzheimer’s disease treatment regimen. In certain embodiments, the signature proteins are selected from any one or more of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3 (or any combination thereof). In certain embodiments, the signature proteins include at least two signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least three signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least four signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least five signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least six signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least seven signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least eight signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least nine signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least ten signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least eleven signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least twelve signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least thirteen signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least fourteen signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least fifteen signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least sixteen signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least seventeen signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least eighteen signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature proteins include at least nineteen signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In another embodiment, the signature protein(s) include at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, or more signature proteins selected from the group consisting of the SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3.

In one embodiment, a subject having or is at risk of developing Alzheimer's disease may be identified by determining the relative level of a signature protein, or a group of signature proteins, in a sample from the subject, wherein the signature protein, or group of signature proteins, is at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, or more signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3.

Determining whether a level of a signature protein in a biological sample derived from a subject is different from a level of the signature protein(s) present in a control (e.g., a healthy, non-AD control) subject may be ascertained by comparing the level of the signature protein(s) in the sample from the subject with a suitable control of the same signature protein(s). The skilled person can select an appropriate control for the assay in question.

In one embodiment, in determining whether a subject has, or is at risk of developing Alzheimer's disease and has levels of signature protein(s) associated with having, or at risk of developing, Alzheimer's disease, a statistically significant increase (or decrease) in the level of at least one signature protein(s) in a sample from the subject relative to the suitable control is indicative that the subject has, or is at risk of developing, Alzheimer's disease. Alternatively, if a suitable control is obtained from a subject known to have Alzheimer's disease, levels of the at least one signature protein(s) comparable to such a control (i.e., a control subject known to have Alzheimer's disease) are indicative of a subject having Alzheimer's disease or being at risk of developing Alzheimer's disease.

Generally, a suitable control may also be a reference standard. A reference standard serves as a reference level for comparison, such that biological samples can be compared to the reference standard in order to infer Alzheimer's disease or to infer risk of developing Alzheimer's disease in a subject. A reference standard may be representative of the level of one or more signature protein(s) in a known subject, e.g., a subject known to be a normal subject (e.g., a healthy subject without Alzheimer's disease). Likewise, a reference standard may be representative of the level of one or more signature protein(s) in a population of known subjects, e.g., a population of subjects known to be normal subjects, or in an alternative embodiment, a population of subjects known to have Alzheimer's disease.

In certain aspects, the present disclosure features a method for identifying a subject who has, or is at risk of developing, Alzheimer's disease, said method comprising determining the relative level of a signature protein(s) in a biological sample from the subject, wherein a higher or a lower level of the signature protein(s) in the sample relative to a control level of the signature protein(s) (e.g., a healthy control level, or a known standard control level of the signature protein(s)) indicates that the subject has, or is at risk of developing, Alzheimer's disease. In certain embodiments, the signature protein(s) are selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3 (or any combination thereof).

The signature protein(s) described herein can be used individually or in any combination in methods to identify a subject who has, or is at risk of developing Alzheimer's disease (e.g. diagnostic tests). Based on the identification of a subject who has Alzheimer's disease, or a subject who is at risk of developing Alzheimer's disease, additional procedures may be indicated, including, for example, additional diagnostic tests or therapeutic procedures. The signature protein(s) described herein can also be used individually or in any combination in methods to monitor the therapeutic efficacy of an Alzheimer's disease treatment regimen in a subject who has, or is at risk of developing Alzheimer's disease.

The present disclosure has identified particular signature protein(s) that are differentially present in subjects who have, or are at risk of developing Alzheimer's disease. The signature protein(s) disclosed herein are differentially present in biological samples derived from subjects who have, or who are at risk of developing Alzheimer's disease, and thus are individually (or collectively in any combination) useful in facilitating the identification of subjects having Alzheimer's disease of facilitating the determination of subjects at risk of developing Alzheimer's disease. Such methods involve determining the level of the signature protein(s) (or any combination of signature protein(s)) in a biological sample derived from the subject. Determining the level of the signature protein(s) in a biological sample may include measuring, detecting, or assaying the level of the signature protein(s) in the biological sample using any suitable method, including, for example, the methods described herein. Determining the level of the signature protein(s) in a biological sample may also include examining the results of an assay that measured, detected, or assayed the level of the signature protein(s) in the biological sample. The method may also involve comparing the level of the signature protein(s) in a biological sample with a suitable control. A change in the level of the signature protein(s) relative to that in a normal (e.g., non-AD) subject as assessed using a suitable control is indicative of whether the subject has Alzheimer's disease, or is at risk of developing Alzheimer's disease. A diagnostic amount of a signature protein(s) that represents an amount of the signature protein(s) above or below which a subject is classified as having Alzheimer's disease or having a particular risk status associated with Alzheimer's disease can also be used. For example, if the signature protein(s) is downregulated in a biological sample derived from the subject as compared to a control sample, a measured amount below the diagnostic cutoff provides an indication of having Alzheimer's disease or being at risk of developing Alzheimer's disease. Alternatively, if the signature protein(s) is upregulated in a biological sample derived from the subject as compared to a control sample, a measured amount above the diagnostic cutoff provides an indication of having Alzheimer's disease or being at risk of developing Alzheimer's disease. As is well-understood in the art, adjusting the particular diagnostic cut-off used in an assay allows one to adjust the sensitivity and/or specificity of the diagnostic assay as desired.

In certain embodiments, the method may further comprise providing a diagnosis that the subject has or does not have Alzheimer's disease based on the level of at least one signature protein(s) in a biological sample. In other embodiments, the method may further comprise providing a diagnosis that the subject is at risk or is not at risk of developing Alzheimer's disease based on the level of at least one signature protein(s) in a biological sample.

While individual signature proteins are useful in identifying a subject who has or is at risk of developing Alzheimer's disease, as shown herein, a combination of signature proteins may also be used to provide a greater predictive value of whether a subject who has or is at risk of developing Alzheimer's disease. Without wishing to be bound by any particular theory, the present disclosure provides that mitochondrial changes in the cortex, CSF and serum may be highly associated with Alzheimer's disease. These changes may coincide with early amyloid deposition in the brain of asymptomatic cases with amyloid pathology, as well in patients with mild cognitive impairment (MCI), and may be at least partially due to amyloid peptides aggregating in the mitochondrial compartment. Specifically, in certain embodiments, the detection of a plurality (or combination) of signature proteins can increase the accuracy, sensitivity, and/or specificity of a diagnostic test described herein. Accordingly, the present invention includes the individual signature proteins as described herein, as well as combinations of signature proteins, and their use in the compositions and methods described herein. In certain embodiments, the levels of at least two signature proteins in a biological sample are determined, wherein the at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins as described herein) are selected from SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3.

The level of at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins as described herein) that are reliably indicative of having Alzheimer's disease or being at risk of developing Alzheimer's disease may be used as a stand-alone diagnostic indicator. In certain other embodiments, the methods described herein may further include the measurement or detection of at least one additional indicator (e.g., the detection of levels of beta-amyloid in the brain of a subject via structural imaging (e.g., magnetic resonance imaging (MM) or computed tomography (CT)) or performance of a subject in a cognitive test (e.g., Mini-Mental State Exam (MMSE) and the Mini-Cog test)) to facilitate identifying a subject who has or is at risk of developing Alzheimer's disease.

In one embodiment, the present disclosure features a method of diagnosing Alzheimer's disease (AD) in a patient, said method comprising obtaining a biological sample from a human patient, detecting the relative level of at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) as described herein selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3, and diagnosing a patient with Alzheimer's disease when a higher level of the at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or all nineteen signature proteins) is detected in comparison to, for example, a known standard control level (or a healthy (non-AD) control level) of the at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) in the biological sample.

In another embodiment, the present disclosure features a method of diagnosing Alzheimer's disease (AD) in a patient, said method comprising obtaining a biological sample from a human patient, detecting the relative level of at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3, and diagnosing a patient with Alzheimer's disease when a lower level of the at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) is detected in comparison to, for example, a known standard control level (or a healthy (non-AD) control level) of the at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) in the biological sample.

In one embodiment, the present disclosure features a method of identifying a subject who is at risk of developing Alzheimer's disease (AD), said method comprising obtaining a biological sample from a human patient, detecting the relative level of at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3 in the biological sample, and identifying the subject who is at risk of developing Alzheimer's disease when a higher level of the at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3 is detected in comparison to, for example, a known standard control level (or a healthy (non-AD) control level) of the at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) in the biological sample.

In one embodiment, the present disclosure features a method of identifying a subject who is at risk of developing Alzheimer's disease (AD), said method comprising obtaining a biological sample from a human patient, detecting the relative level of at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3 in the biological sample, and identifying the subject who is at risk of developing Alzheimer's disease when a lower level of the at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3 is detected in comparison to, for example, a known standard control level (or a healthy (non-AD) control level) of the at least two signature proteins (or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine signature proteins) in the biological sample.

III. Methods and Compositions Relating to Identifying Alzheimer's Disease

The methods and compositions as described herein are based, at least in part, on the discovery that certain proteins (i.e., signature proteins) are associated with Alzheimer's disease (AD). Examples of signature proteins that may be used in the methods and compositions as described herein are provided below. As described herein, the term signature protein is intended to include the protein (and nucleic acids encoding the protein), as well as functional fragments thereof (of either the protein or the nucleic acids). A functional fragment would retain, for example, the ability ascribed to corresponding full length (or non-fragment) equivalent.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes SUCLG2 (also known as Succinate-CoA Ligase GDP-Forming Subunit Beta, Succinate—CoA Ligase [GDP-Forming] Subunit Beta, Mitochondrial, GTP-Specific Succinyl-CoA Synthetase Subunit Beta, Succinate-CoA Ligase GDP-Forming Beta Subunit, EC 6.2.1.4, SCS-BetaG, GTPSCS, G-SCS, Succinyl-CoA Ligase [GDP-Forming] Subunit Beta, Mitochondrial, GTP-Specific Succinyl-CoA Synthetase Beta Subunit, Succinyl-CoA Synthetase, Beta-G Chain, EC 6.2.1 and GBETA). The sequence of SUCLG2 can be found at, for example, UniProt Accession No. Q96199.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes NTN1 (also known as Netrin 1, Netrin-1, Epididymis Tissue Protein Li 131P, NTN1L, Netrin 1, Mouse, Homolog Of, and MRMV4). The sequence of NTN1 can be found at, for example, UniProt Accession No. 095631.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or at the least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes C1QTNF5 (also known as C1q And TNF Related 5, Complement C1q Tumor Necrosis Factor-Related Protein 5, C1q And Tumor Necrosis Factor Related Protein 5, Myonectin, CTRP5, Complement-C1q Tumor Necrosis Factor-Related Protein 5, Membrane Frizzled-Related Protein, C1q TNF-Alpha-Related Protein 5, and MFRP). The sequence of C1QTNF5 can be found at, for example, UniProt Accession No. Q9BXJ0.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes OLFML3 (also known as Olfactomedin Like 3, Olfactomedin-Like Protein 3, HNOEL-Iso, Olfactomedin, 44-Kd, Olfactomedin-Like 3, HOLF44, and OLF44). The sequence of OLFML3 can be found at, for example, UniProt Accession No. Q9NRN5.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes SLIT2 (also known as Slit Guidance Ligand 2, Slit Homolog 2 Protein, Slit-2, SLIL3, Slit (*Drosophila*) Homolog 2, and Slit Homolog 2 (*Drosophila*)). The sequence of SLIT2 can be found at, for example, UniProt Accession No. 094813.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes SPON1 (also known as Spondin 1, Vascular Smooth Muscle Cell Growth-Promoting Factor, Spondin 1, (F-Spondin) Extracellular Matrix Protein, F-Spondin, Spondin-1, Spondin 1, Extracellular Matrix Protein, VSGP/F-Spondin, KIAA0762 and VSGP). The sequence of SPON1 can be found at, for example, UniProt Accession No. Q9HCB6.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes GPNMB (also known as Glycoprotein Nmb, Hematopoietic Growth Factor Inducible Neurokinin-1 Type, Hematopoietic Growth Factor Inducible Neurokinin-1, Glycoprotein Nonmetastatic Melanoma Protein B, Glycoprotein (Transmembrane) Nmb, Transmembrane Glycoprotein NMB, Glycoprotein Nmb-Like Protein, Osteoactivin, HGFIN, NMB, Transmembrane Glycoprotein HGFIN, Transmembrane Glycoprotein, Glycoprotein NMB and PLCA3). The sequence of GPNMB can be found at, for example, UniProt Accession No. Q14956.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes SOD2 (also known as Superoxide Dismutase 2, Superoxide Dismutase [Mn], Mitochondrial, Superoxide Dismutase 2, Mitochondrial, EC 1.15.1.1, Epididymis Secretory Sperm Binding Protein, Manganese-Containing Superoxide Dismutase, Mangano-Superoxide Dismutase, Mn Superoxide Dismutase, Indophenoloxidase B, Mn-SOD, IPO-B, MNSOD, MVCD6, and IPOB). The sequence of SOD2 can be found at, for example, UniProt Accession No. P04179.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes PRDX3 (also known as Peroxiredoxin 3, Antioxidant Protein 1, Thioredoxin-Dependent Peroxide Reductase, Mitochondrial, Protein MER5 Homolog, Peroxiredoxin III, EC 1.11.1.15, Prx-III, HBC189, AOP-1, AOP1, Epididymis Secretory Sperm Binding Protein, Peroxiredoxin-3, PRO1748, SP-22 and MER5). The sequence of PRDX3 can be found at, for example, UniProt Accession No. P30048.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes ALDH6A1 (also known as Aldehyde Dehydrogenase 6 Family Member A1, Methylmalonate-Semialdehyde Dehydrogenase [Acylating], Mitochondrial, Malonate-Semialdehyde Dehydrogenase (Acetylating), MMSDH, Mitochondrial Acylating Methylmalonate-Semialdehyde Dehydrogenase, Malonate-Semialdehyde Dehydrogenase [Acylating], Aldehyde Dehydrogenase 6 Family, Member A1, Aldehyde Dehydrogenase Family 6 Member A1, Malonate-Semialdehyde Dehydrogenase, Testicular Tissue Protein Li 122, EC 1.2.1.18, EC 1.2.1.27, and MMSADHA). The sequence of ALDH6A1 can be found at, for example, UniProt Accession No. Q02252.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes ETFB (also known as Electron Transfer Flavoprotein Subunit Beta, Beta-ETF, Electron-Transferring-Flavoprotein, Beta Polypeptide, FP585, and MADD). The sequence of ETFB can be found at, for example, UniProt Accession No. P38117.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes HADHA (also known as Hydroxyacyl-CoA Dehydrogenase Trifunctional Multienzyme Complex Subunit Alpha, Hydroxyacyl-Coenzyme A Dehydrogenase/3-Ketoacyl-Coenzyme A, Thiolase/Enoyl-Coenzyme A Hydratase (Trifunctional Protein), Alpha Subunit, Hydroxyacyl-CoA Dehydrogenase/3-Ketoacyl-CoA Thiolase/Enoyl-CoA Hydratase (Trifunctional Protein), Alpha Subunit, Mitochondrial Trifunctional Protein, Alpha Subunit, Trifunctional Enzyme Subunit Alpha, Mitochondrial, Long-Chain-3-Hydroxyacyl-CoA Dehydrogenase, Monolysocardiolipin Acyltransferase, Long-Chain 2-Enoyl-CoA Hydratase, 78 KDa Gastrin-Binding Protein, Gastrin-Binding Protein, HADH, Mitochondrial Long-Chain L-3-Hydroxyacyl-Coenzyme A (CoA) Dehydrogenase, Mitochondrial Long-Chain 2-Enoyl-Coenzyme A (CoA) Hydratase, Alpha Subunit, 3-Ketoacyl-Coenzyme A (CoA) Thiolase, Alpha Subunit, and Mitochondrial Trifunctional Enzyme, Alpha Subunit). The sequence of HADHA can be found at, for example, UniProt Accession No. P40939.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes CYB5R3 (also known as Cytochrome B5 Reductase 3, NADH-Cytochrome B5 Reductase 3, Diaphorase-1, EC 1.6.2.2, DIA1, B5R, NADH-Cytochrome B5 Reductase 3 Membrane-Bound Form, Diaphorase (NADH) (Cytochrome B-5 Reductase), NADH-Cytochrome B5 Reductase 3 Soluble Form, Mutant NADH-Cytochrome B5 Reductase, and Cytochrome B5 Reductase). The sequence of CYB5R3 can be found at, for example, UniProt Accession No. P00387.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes CTHRC1 (also known as Collagen Triple Helix Repeat Containing 1, Collagen Triple Helix Repeat-Containing Protein 1, and Protein NMTC1). The sequence of CTHRC1 can be found at, for example, UniProt Accession No. Q96CG8.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes OLFM3 (also known as Olfactomedin 3, Optimedin, Noelin-3, NOE3, Olfactomedin Related ER Localized Protein 3, Olfactomedin-3, OPTIMEDIN, and NOELIN3). The sequence of OLFM3 can be found at, for example, UniProt Accession No. Q96PB7.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes SMOC1 (also known as SPARC Related Modular Calcium Binding 1, SPARC-Related Modular Calcium-Binding Protein 1, Secreted Modular Calcium-Binding Protein 1, SMOC-1, and OAS). The sequence of SMOC1 can be found at, for example, UniProt Accession No. Q9H4F8.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes TAU (also known as Microtubule Associated Protein Tau, G Protein Beta1/Gamma2 Subunit-Interacting Factor 1, Protein Phosphatase 1, Regulatory Subunit 103, Microtubule-Associated Protein Tau, Neurofibrillary Tangle Protein, Paired Helical Filament-Tau, PHF-Tau, MAPTL, MTBT1, Microtubule-Associated Protein Tau, Isoform 4, PPP1R103, FTDP-17, MTBT2, DDPAC, MSTD and PPND). The sequence of TAU can be found at, for example, UniProt Accession No. P10636.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or the at least nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes GFAP (also known as Glial Fibrillary Acidic Protein, Intermediate Filament Protein and ALXDRD). The sequence of GFAP can be found at, for example, UniProt Accession No. P14136.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes NPTX2 (also known as Neuronal Pentraxin 2, Neuronal Pentraxin II, Neuronal Pentraxin-2, Apexin, NP-II, NP2, Neuronal Activity-Regulated Pentaxin, and NARP). The sequence of NPTX2 can be found at, for example, UniProt Accession No. P47972.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes OLFM1 (also known as Olfactomedin 1, Noelin, NOE1, Neuronal Olfactomedin-Related ER Localized Protein, OlfA, AMY, Olfactomedin Related ER Localized Protein, Neuroblastoma Protein, Olfactomedin-1, Pancortin 1, Pancortin, NOELIN1, NOELIN, and NOEL1). The sequence of OLFM1 can be found at, for example, UniProt Accession No. Q99784.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes NGEF (also known as Neuronal Guanine Nucleotide Exchange Factor, Eph-Interacting Exchange Protein, Ephexin-1, Ephexin1, ARHGEF27, Ephexin, and EPHEXIN). The sequence of NPTX2 can be found at, for example, UniProt Accession No. Q8N5V2.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes DGKG (also known as Diacylglycerol Kinase Gamma, Diacylglycerol Kinase, Gamma 90 kDa, Diglyceride Kinase Gamma, DAG Kinase Gamma, EC 2.7.1.107, DAGK3, Diacylglycerol Kinase, Gamma (90 kD), Diacylglyerol Kinase Gamma, DGK-GAMMA, and DGK-Gamma). The sequence of NPTX2 can be found at, for example, UniProt Accession No. P49619.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes SLC6A1 (also known as Solute Carrier Family 6 Member 1, GABATR, GAT1, Solute Carrier Family 6 (Neurotransmitter Transporter, GABA), Member 1, Solute Carrier Family 6 (Neurotransmitter Transporter), Member 1, Sodium- And Chloride-Dependent GABA Transporter 1, GABA Transporter 1, GABATHG, GABT1, GAT-1 and MAE). The sequence of SLC6A1 can be found at, for example, UniProt Accession No. P30531.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes GRIN1 (also known as Glutamate Ionotropic Receptor NMDA Type Subunit 1, N-Methyl-D-Aspartate Receptor Subunit NR1, GluN1, Glutamate Receptor, Ionotropic, N-Methyl D-Aspartate 1, Glutamate [NMDA] Receptor Subunit Zeta-1, Glutamate Receptor Ionotropic, NMDA 1, NMD-R1, NMDAR1, N-Methyl-D-Aspartate Receptor Channel, Subunit Zeta-1, NDHMSD, NDHMSR, NMDA1, MRD8 and NR1). The sequence of GRIN1 can be found at, for example, UniProt Accession No. Q05586.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes APOC2 (also known as Apolipoprotein C2, Apolipoprotein C-II, APO-CII, APOC-II, Apo-CII, ApoC-II and APC2). The sequence of APOC2 can be found at, for example, UniProt Accession No. P02655.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes SDHA (also known as Succinate Dehydrogenase Complex Flavoprotein Subunit A, Flavoprotein Subunit Of Complex II, SDHF, Succinate Dehydrogenase [Ubiquinone] Flavoprotein Subunit, Mitochondrial, Succinate Dehydrogenase Complex, Subunit A, Flavoprotein (Fp), SDH2, FP, Succinate Dehydrogenase [Ubiquinone] Flavoprotein Subunit, EC 1.3.5.1, CMD1GG, MC2DN1, PGL5, SDH1 and Fp). The sequence of SDHA can be found at, for example, UniProt Accession No. P31040.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes ECI1 (also known as Enoyl-CoA Delta Isomerase 1, Dodecenoyl-Coenzyme A Delta Isomerase (3,2 Trans-Enoyl-Coenzyme A Isomerase), Enoyl-CoA Delta Isomerase 1, Mitochondrial, Delta(3), Delta(2)-Enoyl-CoA Isomerase, D3,D2-Enoyl-CoA Isomerase, Dodecenoyl-CoA Isomerase, DCI, Dodecenoyl-CoA Delta Isomerase (3,2 Trans-Enoyl-CoA Isomerase), 3,2-Trans-Enoyl-CoA Isomerase, Mitochondria, Epididymis Secretory Sperm Binding Protein, 3,2 Trans-Enoyl-Coenzyme A Isomerase, 3,2 Trans-Enoyl-CoA Isomerase, 3,2-Trans-Enoyl-CoA Isomerase, Acetylene-Allene Isomerase, EC 5.3.3.8 and ECI1). The sequence of ECI1 can be found at, for example, UniProt Accession No. P42126.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes HSPA9 (also known as Heat Shock Protein Family A (Hsp70) Member 9, 75 KDa Glucose-Regulated Protein, Stress-70 Protein, Mitochondrial, GRP75, PBP74, PBP74, Peptide-Binding Protein 74, Mortalin2, Mortalin, GRP-75, HSPA9B, MOT, Epididymis Secretory Sperm Binding Protein Li 124m, Heat Shock 70 kDa Protein 9B (Mortalin-2), Catecholamine-Regulated Protein 40, Heat Shock 70 KDa Protein 9, Heat Shock 70 kD Protein 9B, Mortalin, Perinuclear, P66-Mortalin, HEL-S-124m, Mortalin-2, Mt-HSP70, MTHSP75, Mthsp75, SIDBA4, CRP40, EVPLS, Mot-2, MOT2, SAAN and CSA). The sequence of HSPA9 can be found at, for example, UniProt Accession No. P38646.

In one embodiment of the disclosure, the at least one signature protein (or the at least two, or the at least three, or the at least four, or the at least five, or the at least six, or the at least seven, or the at least eight, or the at least nine, or the at least ten, or the at least eleven, or the at least twelve, or the at least thirteen, or the at least fourteen, or at the least fifteen, or the at least sixteen, or the at least seventeen, or the at least eighteen, or all nineteen, or the at least twenty, or the at least twenty-one, or the at least twenty-two, or the at least twenty-three, or the at least twenty-four, or the at least twenty-five, or the at least twenty-six, or the at least twenty-seven, or the at least twenty-eight, or the at least twenty-nine signature proteins) used in the methods and compositions described herein includes MYL3 (also known as Myosin Light Chain 3, MLC1SB, Myosin, Light Polypeptide 3, Alkali; Ventricular, Skeletal, Slow, Myosin, Light Chain 3, Alkali; Ventricular, Skeletal, Slow, Ventricular/Slow Twitch Myosin Alkali Light Chain, Ventricular Myosin Alkali Light Chain, Ventricular Myosin Light Chain 1, Cardiac Myosin Light Chain 1, MLC-LV/Sb, MLC1V, CMLC1, CMH8, VLC1, VLC1 and Myosin Light Chain 1, Slow-Twitch Muscle B/Ventricular Isoform). The sequence of MYL3 can be found at, for example, UniProt Accession No. P08590.

Biological Samples

The expression level of one or more signature proteins may be determined in a biological sample derived from a subject. A sample derived from a subject is one that originates and is obtained from a subject. Such a sample may be further processed after it is obtained from the subject. For example, protein or nucleic acid (e.g., a mRNA) may be isolated from a sample. In one embodiment, the signature protein isolated from the sample is also a sample derived from a subject. In another embodiment, the signature protein may be detected in a sample obtained from a subject non-invasively. In other embodiments, the biological sample is a bodily fluid, for example, a blood sample, or a fraction thereof, a serum sample, a plasma sample, a lymph sample, a urine sample, a saliva sample, a tear sample, a sweat sample, a semen sample, a vaginal sample, a bronchial sample, a mucosal sample, or a cerebrospinal fluid (CSF) sample.

Determining the Level of the One or More Signature Proteins in a Biological Sample As described herein, the present disclosure provides signature proteins useful in identifying/diagnosing a subject having Alzheimer's disease or having an increased risk of developing Alzheimer's disease. Accordingly, the present disclosure provides that signature proteins levels can be assayed from a biological sample obtained from a subject in order to determine whether the subject has Alzheimer's disease, or has an increased risk of developing Alzheimer's disease. In certain embodiments, the signature proteins are identified by comparing the levels of certain proteins in biological samples from subjects with Alzheimer's disease with the levels of certain proteins in a biological sample from subjects who do not have Alzheimer's disease (or with the levels of certain proteins in a biological sample from healthy control subjects, or with the levels of certain proteins of a known standard control level or known reference level). Many differentially expressed proteins were identified in this manner, and were determined to be reliably indicative of a subject having Alzheimer's disease, including the following the signature proteins, i.e., SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3 (or any combination thereof). Thus, in a particular embodiment, a difference in the level of one or more of these signature proteins as compared to the level of one or more of these signature proteins in a biological sample derived from a healthy control subject (i.e., a subject known to not have Alzheimer's disease) is indicative of whether the subject has (or is at risk of developing) Alzheimer's disease.

The level of one or more signature proteins in a biological sample may be determined by any suitable method. Any reliable method for measuring the level or amount of protein in a sample may be used. Accordingly, practicing the methods disclosed herein may utilize routine techniques in the field of molecular biology. Basic texts disclosing the general methods of use in this disclosure include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

In some embodiments, the present disclosure relates to a method (e.g., in vitro method) of measuring the amount of protein levels found in a biological sample of a subject, as a means to detect the presence, to assess the risk of developing, diagnosing, prognosing, and/or monitoring the progression of and/or monitoring the efficacy of a treatment for Alzheimer's disease. Thus, the first steps of practicing the methods of this disclosure are to obtain a biological sample from a subject and extract and/or isolate protein from the sample.

Preparation of Biological Samples

In some embodiments, a biological sample is obtained from a subject to be tested or monitored for Alzheimer's disease. In one embodiment, biological samples of the same type should be taken from both a test subject (e.g., a subject suspected of having Alzheimer's disease) and a control subject (e.g., a subject not suffering from Alzheimer's disease). In yet another embodiment, a biological sample may be taken from a test subject (e.g., a subject suspected of having Alzheimer's disease) and compared to a known control standard. Collection of a biological sample from a subject may be performed in accordance with the standard protocol hospitals or clinics generally follow. An appropriate amount of biological sample is collected and may be stored according to standard procedures prior to further preparation.

The analysis of signature proteins, as described herein, found in a biological sample of a subject according to the method disclosed herein may be performed in certain embodiments, using, e.g., a blood sample, or a fraction thereof, a serum sample, a plasma sample, a lymph sample, a urine sample, a saliva sample, a tear sample, a sweat sample, a semen sample, a vaginal sample, a bronchial sample, a mucosal sample, or a cerebrospinal fluid (CSF) sample. The methods for preparing biological samples for protein extraction/isolation are well known among those of skill in the art. For example, a cell population or a tissue sample of a subject should be first treated to disrupt cellular membrane so as to release protein contained within the cells.

For the purpose of detecting the presence of signature proteins disclosed herein or assessing whether a test subject has or is at risk of developing Alzheimer's disease, a biological sample may be collected from the subject and the level of at least one signature protein may be measured and then compared to the normal level of the same at least one signature protein in the same type of biological sample from a healthy control subject (e.g., a subject who does not have Alzheimer's disease), and/or compared to a known standard control level or baseline levels of the same at least one signature protein. If an increase or decrease in the level of the at least one signature protein disclosed herein is observed when compared to the normal (non-AD) level of the same at least one signature protein, the test subject is deemed to have Alzheimer's disease or have an increased risk of developing Alzheimer's disease. For the purpose of monitoring disease progression or assessing therapeutic effectiveness in Alzheimer's disease patients, a biological sample from a subject may be taken at different time points (e.g., hours, days, weeks, months, years, etc.) such that the level of the at least one signature protein can be measured to provide information indicating the state of disease (i.e., Alzheimer's disease). For instance, when the level of the at least one signature protein from a subject shows a general trend of stabilizing at a level comparable to a healthy control subject (or known standard level) over time, the subject is deemed to be improving or stabilizing in the severity of Alzheimer's disease or the therapy the patient has been receiving is deemed effective. A lack of stabilization to a level comparable to a healthy control subject (or known standard level) over time or a continuing trend of an increase or decrease in the level the at least one signature protein when compared to the normal level of the same at least one signature protein would indicate a worsening of the condition and ineffectiveness of the therapy given to the patient. Generally, a comparatively higher level (or lower level) of the at least one signature protein in a subject when compared to the normal level of the same at least one signature protein indicates that the subject has Alzheimer's disease and/or that the subject's Alzheimer's disease is worsening.

Determining the Level of Signature Proteins

A protein of any particular identity, such as a signature protein as disclosed herein, can be detected using a variety of immunological assays. In one embodiment, an immunoassay (e.g., a sandwich assay) can be performed by capturing the signature protein from a biological sample with an antibody (or antibodies) having specific binding affinity for the signature protein. The signature protein can subsequently be detected using, e.g., a labeled antibody having specific binding affinity for the signature protein. One common method of detection is the use of autoradiography by using a radiolabeled detection agent (e.g., a radiolabeled anti-biomarker specific antibody) that is labeled with radioisotopes (e.g., $^{3}H$, $^{125}I$, $^{35}S$, $^{14}C$, or $^{32}P$, $^{99m}Tc$, or the like). The choice of radioactive isotope depends on research preferences due to ease of synthesis, stability, and half-lives of the selected isotopes. Other labels that can be used for labeling of detection agents include compounds (e.g., biotin and digoxigenin), which bind to anti-ligands or antibodies labeled with fluorophores, chemiluminescent agents, fluorophores, and enzymes (e.g., HRP). Such immunological assays can be carried out using microfluidic devices such as microarray protein chips. A signature protein can also be detected by gel electrophoresis (such as 2-dimensional gel electrophoresis) and western blot analysis using specific antibodies. In some embodiments, standard ELISA techniques can be used to detect a signature protein, using an appropriate antibody (or antibodies). In other embodiments, standard western blot analysis techniques can be used to detect a signature protein, using the appropriate antibodies. Alternatively, standard immunohistochemical (IHC) techniques can be used to detect a signature protein, using an appropriate antibody (or antibodies). Both monoclonal and polyclonal antibodies (including an antibody fragment with desired binding specificity) can be used for specific detection of the signature protein. Such antibodies and their binding fragments with specific binding affinity to a signature protein can be generated by known techniques.

In some embodiments, a signature protein can be detected in a detection assay with an antibody that binds to the signature protein, such as an anti-signature protein specific antibody, or an antigen-binding fragment thereof. In certain embodiments, an anti-signature protein specific antibody is used as a detection agent, such as a detection antibody that binds to a signature protein and detects the signature protein (e.g., from a biological sample), such as detects the signature protein in a detection assay (e.g., in western blot analysis, immunohistochemistry analysis, autoradiography analysis, and/or ELISA). In certain embodiments, an anti-signature protein specific antibody is used as a capture agent that binds to the signature protein and detects the signature protein (e.g., from a biological sample), such as detects the protein biomarker in a detection assay (e.g., in western blot analysis, immunohistochemistry analysis, autoradiography analysis, and/or ELISA). In some embodiments, an anti-signature protein specific antibody, or an antigen-binding fragment thereof is labeled for ease of detection. In some embodiments, anti-signature protein specific antibody, or an antigen-binding fragment thereof is radiolabeled (e.g., labeled with a radioisotope, such as labeled with $^{3}H$, $^{12}I$, $^{35}S$, $^{14}C$, or $^{32}P$, $^{99m}Tc$, or the like), enzymatically labelled (e.g., labeled with an enzyme, such as with horseradish peroxidase (HRP)), fluorescent labeled (e.g., labeled with a fluorophore), labeled with a chemiluminescent agent and/or labeled with a compound (e.g., with biotin and digoxigenin).

Other methods may also be employed for measuring the level of a signature protein in practicing the present disclosure. For instance, a variety of methods have been developed based on the mass spectrometry technology to rapidly and accurately quantify proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res* 2009 February; 8(2):787-797.

In other embodiments, the expression level of a signature protein is evaluated by assessing the signature protein as disclosed herein. In some embodiments, an anti-signature protein specific antibody, or fragment thereof, can be used to assess the signature protein. Such methods may involve using IHC, western blot analyses, ELISA, immunoprecipitation, autoradiography, or an antibody array. In other embodiments, the expression level of a signature protein is evaluated by using a multiplexed tandem mass-tag analysis, a liquid chromatography (LC) fractionation analysis, a TOMAHAQ analysis, a TMT-LC/LC/MS/MS platform analysis, or an ultra-deep proteomic platform analysis.

Quantification of Nucleic Acids

In certain embodiments, the present disclosure relates to a method (e.g., in vitro method) of measuring the amount of certain nucleic acid levels (e.g., nucleic acid levels corresponding to the signature proteins as disclosed herein, or certain mRNA signature protein levels) found in a biological sample of a subject, as a means to detect the presence, to assess the risk of developing, diagnosing, prognosing, monitoring the progression of and/or monitoring the efficacy of a treatment for Alzheimer's disease. Thus, in certain embodiments, the first steps of practicing the methods of this disclosure (e.g., in vitro methods of using certain nucleic acid levels of certain signature proteins for diagnosis, prognosis, and/or monitoring of Alzheimer's disease) are to obtain a biological sample from a subject and extract nucleic acid (e.g., genomic DNA, RNA, and/or mRNA) from the biological sample. In some embodiments, a biological sample is obtained from a subject to be tested or monitored for Alzheimer's disease. Collection of a biological sample from a subject, may be performed in accordance with the standard protocol hospitals or clinics generally follow. An appropriate amount of biological sample is collected and may be stored according to standard procedures prior to further preparation.

The analysis of levels of certain nucleic acids (e.g., DNA or mRNA corresponding to the signature proteins as disclosed herein, or corresponding to unique nucleic acid biomarkers), found in biological sample of a subject according to the method disclosed herein may be performed in certain embodiments, using, e.g., a blood sample, or a fraction thereof, a serum sample, a plasma sample, a lymph sample, a urine sample, a saliva sample, a tear sample, a sweat sample, a semen sample, a vaginal sample, a bronchial sample, a mucosal sample, or a cerebrospinal fluid (CSF) sample. The methods for preparing biological samples for nucleic acid extraction are well known among those of skill in the art. For example, a cell population or a tissue sample of a subject should be first treated to disrupt cellular membrane so as to release nucleic acids contained within the cells.

Methods for extracting DNA from a biological sample are well known and routinely practiced in the art of molecular biology (e.g., described by Sambrook and Russell, Molecular Cloning: A Laboratory Manual 3d ed., 2001). RNA contamination should be eliminated to avoid interference with DNA analysis. There are numerous methods for extracting RNA from a biological sample. General methods of RNA preparation are provided, for example, in Sambrook and Russell, see above. In addition, numerous commercially available reagents or kits and combinations thereof, such as Oligotex Direct mRNA Kits (Qiagen, Valencia, Calif.) and RNeasy Mini Kits (Qiagen, Hilden, Germany), may also be used to extract mRNA from a biological sample from a test subject. All contaminating DNA be eliminated from the RNA preparations, using, for example, careful handling of the samples, and treatment with DNase, and proper negative controls in the amplification and quantification steps.

Once nucleic acid is extracted from a sample, the amount of nucleic acid (e.g., genomic DNA, RNA, and/or mRNA) may be quantified. Generally, nucleic acids can be detected and quantified from a sample by various methods known for mRNA, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), Northern Blot analysis, in situ hybridization, etc.), and sequencing-based methods. In one embodiment, the level of the mRNA in a biological sample is determined using quantitative PCR (qPCR) or a Northern blot.

IV. Predictive Methods and Compositions Relating to Determining Risk of Alzheimer's Disease Provided herein are methods and compositions for detecting one or more signature proteins (e.g., SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3) in a biological sample from a subject having, or suspected of having, Alzheimer's disease. In certain embodiments, such methods and compositions are used to determine the risk of Alzheimer's disease for a subject. In particular embodiments, the compositions disclosed herein contemplate a panel composed of at least two (or at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, or at least twenty-nine) signature proteins.

Provided herein are methods and compositions (e.g., panels or kits or assay devices) for determining and/or predicting a subject's risk of having and/or developing Alzheimer's disease based on measuring the levels of signature proteins (e.g., any combination of signature proteins described herein) using one or more of the panels as disclosed herein.

In some embodiments, the levels at least two signature proteins are useful for determining the approximate risk of Alzheimer's disease in a subject. In some embodiments, the levels at least three signature proteins are useful for determining the approximate risk of Alzheimer's disease in a subject. In some embodiments, the levels at least four signature proteins are useful for determining the approximate risk of Alzheimer's disease in a subject. In some embodiments, the levels at least five signature proteins are useful for determining the approximate risk of Alzheimer's disease in a subject. In some embodiments, the levels at least six signature proteins are useful for determining the approximate risk of Alzheimer's disease in a subject. In some embodiments, the levels at least seven signature proteins are useful for determining the approximate risk of Alzheimer's disease in a subject. In some embodiments, the levels at least eight signature proteins are useful for determining the approximate risk of Alzheimer's disease in a subject. In some embodiments, the levels at least nine signature proteins are useful for determining the approximate risk of Alzheimer's disease in a subject. In some embodiments, the levels at least ten signature proteins are useful for determining the approximate risk of Alzheimer's disease in a subject. In some embodiments, the levels at least eleven signature proteins are useful for determining the approximate risk of Alzheimer's disease in a subject. In some embodiments, the levels at least twelve signature proteins are useful for determining the approximate risk of Alzheimer's disease in a subject. In some embodiments, the levels at least thirteen signature proteins are useful for determining the approximate risk of Alzheimer's disease in a subject. In some embodiments, the levels at least fourteen signature proteins are useful for determining the approximate risk of Alzheimer's disease in a subject. In some embodiments, the levels at least fifteen signature proteins are useful for determining the approximate risk of Alzheimer's disease in a subject. In some embodiments, the levels at least sixteen signature proteins are useful for determining the approximate risk of Alzheimer's disease in a subject. In some embodiments, the levels at least seventeen signature proteins are useful for determining the approximate risk of Alzheimer's disease in a subject. In some embodiments, the levels at least eighteen signature proteins are useful for determining the approximate risk of Alzheimer's disease in a subject. In some embodiments, the levels at least nineteen signature proteins are useful for determining the approximate risk of Alzheimer's disease in a subject. In some embodiments, the levels of at least twenty signature proteins are useful for determining the approximate risk of Alzheimer's disease in a subject. In some embodiments, the levels of at least twenty-one signature proteins are useful for determining the approximate risk of Alzheimer's disease in a subject. In some embodiments, the levels of at least twenty-two signature proteins are useful for determining the approximate risk of Alzheimer's disease in a subject. In some embodiments, the levels of at least twenty-three signature proteins are useful for determining the approximate risk of Alzheimer's disease in a subject. In some embodiments, the levels of at least twenty-four signature proteins are useful for determining the approximate risk of Alzheimer's disease in a subject. In some embodiments, the levels of at least twenty-five signature proteins are useful for determining the approximate risk of Alzheimer's disease in a subject. In some embodiments, the levels of at least twenty-six signature proteins are useful for determining the approximate risk of Alzheimer's disease in a subject. In some embodiments, the levels of at least twenty-seven signature proteins are useful for determining the approximate risk of Alzheimer's disease in a subject. In some embodiments, the levels of at least twenty-eight signature proteins are useful for determining the approximate risk of Alzheimer's disease in a subject. In some embodiments, the levels of at least twenty-nine signature proteins are useful for determining the approximate risk of Alzheimer's disease in a subject. Described below are exemplary, non-limiting, methods that are employed using the disclosed panels on samples from subjects with, or suspected of having, Alzheimer's disease.

In certain embodiments, the signature proteins that are detected as part of a panel described herein include at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five, or at least twenty-six, or at least twenty-seven, or at least twenty-eight, or at least twenty-nine, signature proteins selected from any one of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3.

V. Methods of Treatment or Prevention

Methods and compositions for treating or preventing Alzheimer's disease in a subject in need thereof are also featured in the disclosure. In one embodiment, the present disclosure provides methods of treating a subject with, or suspected of having, Alzheimer's disease, e.g., a subject having increased levels of one or more of the signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In other embodiments, a subject having Alzheimer's disease may be treated using the methods described herein without having been identified by the predictive methods of the invention. Accordingly, in one embodiment, the disclosure provides a method of treating a subject who has Alzheimer's disease, or who has been identified as being at risk for developing Alzheimer's disease, comprising determining the relative level of at least one signature protein in a sample from the subject, wherein a higher level of the at least one signature protein in the sample relative to a healthy control level of the at least one signature protein (or a standard control level of the at least one signature protein) indicates that the subject has or is at risk of developing Alzheimer's disease, and administering a therapeutically effective amount of an at least one signature protein antagonist to the subject, such that Alzheimer's disease in the subject is treated or prevented.

In another embodiment, the present disclosure provides methods of treating a subject with, or suspected of having, Alzheimer's disease, e.g., a subject having decreased levels of one or more of the signature proteins selected from the group consisting of SUCLG2, NTN1, C1QTNF5, OLFML3, SLIT2, SPON1, GPNMB, SOD2, PRDX3, ALDH6A1, ETFB, HADHA, CYB5R3, CTHRC1, OLFM3, SMOC1, TAU, GFAP, NPTX2, OLFM1, NGEF, DGKG, SLC6A1, GRIN1, APOC2, SDHA, ECI1, HSPA9, and MYL3. In certain embodiments, a subject having Alzheimer's disease may be treated using the methods described herein without having been identified by the predictive methods of the invention. Accordingly, in one embodiment, the disclosure provides a method of treating a subject who has Alzheimer's disease, or who has been identified as being at risk for developing Alzheimer's disease, comprising determining the relative level of at least one signature protein in a sample from the subject, wherein a lower level of the at least one signature protein in the sample relative to a healthy control level of the at least one signature protein (or a standard control level of the at least one signature protein) indicates that the subject has or is at risk of developing Alzheimer's disease, and administering a therapeutically effective amount of an at least one signature protein agonist to the subject, such that Alzheimer's disease in the subject is treated or prevented.

Accordingly, in some aspects, the present disclosure provides a method of treating (e.g., curing, suppressing, ameliorating associated symptoms of, delaying or preventing the progression of, delaying or preventing onset of, or preventing recurrence or relapse of) Alzheimer's disease in a subject. The amount sufficient to treat the disease is preferably an effective amount, e.g., a therapeutically effective amount, as provided herein.

Alteration of symptoms as a result of treatment can be measured relative to any suitable control. For example, alteration of symptoms can be measured relative to the frequency, severity, or duration, or number of symptoms experienced by the same subject prior to initiating treatment. In other embodiments, alteration of symptoms can be measured relative to the frequency, severity, duration, or number of symptoms experienced by a different subject, or group of subjects, with like symptoms who do not receive the treatment. In some embodiments, the degree of improvement is at least 5%, i.e., at least 5%, 10%, 20%, 30%, 40%, 50%, 60%, 70%, 80%, 90%, 95%, 99% or more, as determined relative to a suitable control.

As used herein, the term treating is used to refer to the reduction of a symptom and/or a biochemical marker of Alzheimer's disease by at least 2%, 4%, 5%, 10%, 15%, 20%, 25%, 30%, 35%, 40%, 45%, 50%, 55%, 60%, 65%, 70%, 75%, 80%, 85%, 90%, 95%, or 99% or more. For example, symptoms can include, but are not limited to, a reduction in a biochemical marker of Alzheimer's disease, for example a reduction in amyloid plaque deposition by 10%, a reduction in the activation of glial cells, for example a reduction in cells expressing GFAP (as an exemplary signature protein) by 10%, or a reduction in an accumulation in the severity of abnormal tangles of threads of tau protein (as an exemplary signature protein) inside brain cells, for example a reduction in the severity of abnormal tangles by 10%, would be considered effective treatments by the methods as disclosed herein. As used herein, symptoms of Alzheimer's disease include but are not limited to memory loss, memory decline, difficulty solving problems, difficulty in performing tasks, confusion with time and place, trouble understanding visual images and spatial relationships, gradual loss of speech, agnosia, and any other symptom of Alzheimer's disease. As alternative examples, a reduction in a symptom, for example, a slowing of the rate of memory loss by 10% or a cessation of the rate memory decline, or a reduction in memory loss by 10% or an improvement in memory by 10% would also be considered as effective treatments by the methods as disclosed herein. As used herein, the methods of treatment can refer to methods of reducing symptoms such as a reduction of any known symptom of Alzheimer's disease by at least 2%, 4%, 5%, 10%, 15%, 20%, 25%, 30%, 35%, 40%, 45%, 50%, 55%, 60%, 65%, 70%, 75%, 80%, 85%, 90%, 95%, or 99% or more. In specific embodiments methods disclosed herein comprise methods of reducing at least one symptom of Alzheimer's disease comprising detecting differential expression of any signature protein disclosed herein and administration of any treatment disclosed herein.

Therapeutic agents useful in the invention may include, but are not limited to, an antagonist of SMOC1, an antagonist of C1QTNF5, an antagonist of OLFML3, an antagonist of SLIT2, an antagonist of SPON1, an antagonist of GPNMB, an antagonist of TAU, an antagonist of GFAP, an antagonist of SUCLG2, an antagonist of PRDX3, an antagonist of NTN1, or any combination thereof.

Therapeutic agents useful in the invention may include, but are not limited to, an agonist of SOD2, an agonist of PRDX3, an agonist of ALDH6A1, an agonist of ETFB, an agonist of HADHA, an agonist of CYB5R3, an agonist of CTHRC1, an agonist of GFAP, an agonist of OLFM3, or any combination thereof.

In yet other embodiments, therapeutic agents useful in the present disclosure may include, but are not limited to, an antagonist/agonist of SUCLG2, an antagonist/agonist of NTN1, an antagonist/agonist of C1QTNF5, an antagonist/agonist of OLFML3, an antagonist/agonist of SLIT2, an antagonist/agonist of SPON1, an antagonist/agonist of GPNMB, an antagonist/agonist of SOD2, an antagonist/agonist of PRDX3, an antagonist/agonist of ALDH6A1, an antagonist/agonist of ETFB, an antagonist/agonist of HADHA, an antagonist/agonist of CYB5R3, an antagonist/agonist of CTHRC1, an antagonist/agonist of OLFM3, an antagonist/agonist of SMOC1, an antagonist/agonist of TAU, an antagonist/agonist of GFAP, an antagonist/agonist of NPTX2, an antagonist/agonist of OLFM1, an antagonist/agonist of NGEF, an antagonist/agonist of DGKG, an antagonist/agonist of SLC6A1, an antagonist/agonist of GRIN1, an antagonist/agonist of APOC2, an antagonist/agonist of SDHA, an antagonist/agonist of ECI1, an antagonist/agonist of HSPA9, and an antagonist/agonist of MYL3, or any combination thereof.

The methods of the invention also include, in certain embodiments, administering an additional agent to the subject, for example a cholinesterase inhibitor (e.g., Aricept®, Exelon®, Razadyne®). The methods of the invention also include, in certain embodiments, administering an additional agent to the subject, for example memantine (e.g., Namenda®). The methods of the invention also include, in certain embodiments, administering an additional agent to the subject, for example, memantine and donepezil (e.g., Namzaric®).

In some embodiments, a therapeutic agent as described herein is administered to a subject as a single dose. In some embodiments, a composition comprising the EV described herein is administered in multiple doses. For example, the composition can be administered, in some embodiments, once every day, twice a day, once every 2 days, once every 3 days, once every 4 days, once every 5 days, once every 6 days, once every 7 days, once every 2 weeks, once every 3 weeks, once every 4 weeks, once every 8 weeks, once every 12 weeks, or once every 6 months. It will be readily apparent to those skilled in the art that other suitable modifications and adaptations of the methods described herein are obvious and may be made using suitable equivalents without departing from the scope of the invention or the embodiments disclosed herein.

The therapeutic agents useful in the present disclosure may be formulated as a variety of pharmaceutical compositions. Pharmaceutical compositions may be prepared in a form appropriate for the intended application. Generally, this will entail preparing compositions that are essentially free of pyrogens, as well as other impurities that could be harmful to humans or animals. Exemplary delivery/formulation systems include colloidal dispersion systems, macromolecule complexes, nanocapsules, microspheres, beads, and lipid-based systems including oil-in-water emulsions, micelles, mixed micelles, and liposomes. Commercially available fat emulsions that are suitable for delivering therapeutic agents useful in the present disclosure include Intralipid, Liposyn, Liposyn II, Liposyn III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are hereby incorporated by reference in their entireties.

The pharmaceutical compositions described herein are formulated to employ appropriate salts and buffers to render delivery vehicles stable and allow for uptake by target cells. Aqueous compositions of the present invention comprise an effective amount of the delivery vehicle comprising therapeutic agents useful in the present disclosure, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present disclosure may be via any route so long as the target tissue is available via that route. For example, administration may be by intrathecal, intradermal, subcutaneous, intramuscular, intraperitoneal or intravenous injection, or by direct injection into target tissue.

The compositions may also be appropriately formulated to be administered parenterally or intraperitoneally. Under ordinary conditions of storage and use, these compositions generally contain a preservative to prevent the growth of microorganisms.

The pharmaceutical forms suitable for injectable use or delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agent(s), for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by their use in the compositions of agents delaying absorption, for example, aluminum monostearate and gelatin.

Sterile injectable solutions may be prepared by incorporating the therapeutic agents described herein in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The invention is further illustrated by the following examples, which should not be construed as limiting. The entire contents of all references, patents and published patent applications cited throughout this application are hereby incorporated by reference in their entirety.

EXAMPLES

Described herein are compositions and methods for detecting, analyzing and/or identifying proteins useful diagnosing, prognosing, and/or treating subjects with, or suspected of having, Alzheimer's disease (AD). The following examples are included for purpose of illustration only and are not intended to be limiting.

Research Design and Methods

The following research design and methods relate to the study described in Examples 1 to 6.

Human Brain Cortex, Cerebrospinal Fluid, and Serum

Human brain cortex, CSF, and serum specimen were provided by the brain and body donation program at Banner Sun Health Research Institute and the Alzheimer's Disease Research Center at Icahn School of Medicine at Mount Sinai with well-established criteria for clinical and pathological diagnoses (Beach, T. G., et al., *Neuropathology* 35(4): p. 354-89 (2015; Wang, M., et al., Sci Data 5: p. 180185 (2018)). All subjects consented to the study. A total of 110 human brain tissue, 20 CSF, and 11 serum cases were used as discovery cohorts (datasets i, ii, v, x in Table 1) for the present proteomics study. All samples were frozen and stored at −80° C. in aliquots of polyethylene tubes until use. Sample information is provided in Table 1.

TABLE 1

Summary of Human and Mouse Proteome Datasets for Biomarker Analysis

| Tissue Type | Dataset | Total Case | AD | MCI | Control | Proteins Quantified | Reference |
|---|---|---|---|---|---|---|---|
| Human Cortex | i | 48 | 19 | 7 | 22 | 12,578 | This study and cohort 1 in Bai B, et al. Neuron. 2020 |
| Human Cortex | ii | 62 | 23 | 0 | 39 | 13,702 | Cohort 2 in Bai B, et al. Neuron. 2020 |
| Human Cortex | iii | 40 | 10 | 20 | 10 | 8,817 | Cortex cohort 1 in Higginbotham L, bioRxiv. 2019 |
| Human Cortex | iv | 27 | 9 | 8 | 10 | 11,244 | Cortex cohort 2 in Higginbotham L, bioRxiv. 2019 |
| Human CSF | v | 20 | 11 | 0 | 9 | 5,941 | This study and Bai B, et al. Neuron. 2020 |
| Human CSF | vi | 40 | 20 | 0 | 20 | 2,875 | CSF cohort 1 in Higginbotham L, bioRxiv. 2019 |
| Human CSF | vii | 96 | 33 | 31 | 32 | 792 | CSF cohort 2 in Higginbotham L, bioRxiv. 2019 |
| Human CSF | viii | 10 | 5 | 0 | 5 | 2,321 | Sathe G, et al. Proteomics Clinical Applications. 2019 |
| * Mouse CSF | ix | 11 | 6 | 0 | 5 | 1,058 | This study |
| Human Serum | x | 11 | 6 | 0 | 5 | 4,826 | Dey K K, et al. Clinical Proteomics. 2019 |
| Summary | 10 | 365 | 142 | 66 | 157 | 17,541 | |

* Note:
AD cases are 5× FAD mice, control cases are age matched healthy mice

Mouse Cerebrospinal Fluid

Wide type (WT) control and 5×FAD transgenic mice that overexpress familial AD mutants (the Swedish mutation, K670N/M671L; the Florida mutation, I716V; and the London mutation, V717I) and PS1 (M146L, L286V) transgenes at the age of 9-12 months were used for the spinal fluid collection. Mice were bred and maintained in a specific pathogen free facility in the Animal Resource Center at St. Jude Children's Research Hospital. All protocols were approved by the Institutional Animal Care and Use Committee. CSF samples were collected following an established protocol (Liu, L. and K. Duff, J Vis Exp. 21 (2008)), and then were snap-frozen in liquid nitrogen, and stored at −80° C. before analysis.

Protein Extraction and Quantification

The frozen samples were lysed in the fresh lysis buffer comprises of 50 mM HEPES, pH 8.5, 8 M urea, and 0.5% sodium deoxycholate with 1× phosphatase inhibitor cocktail (PhosSTOP, Sigma-Aldrich). Protein extraction and concentration measurement were performed using an established protocol (Dey, K. K., et al. Clin Proteomics, 16: p. 16 (2019); Bai, B., et al., Methods Enzymol. 585: p. 377-95 (2017)). Briefly, a BCA assay (Thermo Fisher Scientific) was used for measuring protein amount, and the quantifications were further confirmed by short SDS Coomassie-stained gel (Xu, P., D. M. Duong, and J. M. Peng, *J Proteome Res.* 8(8): p. 3944-50 (2009)). The protein lysates were stored at −80° C. in aliquots before use.

Protein Digestion and Tandem-Mass-Tag (TMT) Labeling

Protein digestion and labeling were performed using a previously optimized protocol (Bai, B., et al., Methods Enzymol. 585: p. 377-95 (2017); Pagala, V. R., et al., *Methods Mol Biol.* 1278: p. 281-305 (2015)). ~0.1 mg of quantified proteins in the lysis buffer with 8 M urea were first digested with Lys-C (Wako, 1:100 w/w) at 21° C. for 2 h, and then the solution was diluted 4-fold to urea concentration of 2 M, trypsin (Promega, 1:50 w/w) was further added for digestion at 21° C. for overnight. The digestion process was terminated by 1% trifluoroacetic acid (TFA). The supernatant was desalted with Sep-Pak C18 cartridge (Waters), and then dried by a speed vacuum. Each sample was re-dissolved in 50 mM HEPES (pH 8.5) for TMT reaction for 30 minutes, and then mixed and pooled equally. Pooled samples were desalted for the subsequent fractionation by offline basic pH Liquid chromatography (LC).

Extensive Two-Dimensional LC/LC-MS/MS Analysis

The pooled TMT labeled peptides were resolved and fractionated by offline basic pH reverse phase LC, and each of the fractions was analyzed by the acidic pH reverse phase LC coupled with MS/MS analysis (Niu, M., et al., *Anal Chem.* 89(5): p. 2956-63 (2017); Wang, H., et al., J. Proteome Res. 14(2): p. 829-38 (2015); Cheng, Y., et al., Nat Neurosci. 21(12): p. 1689-1703 (2018)). The offline basic pH LC was performed with a)(Bridge C18 column (3.5 μm particle size, 4.6 mm×25 cm, Waters), buffer A (10 mM ammonium formate, pH 8.0), buffer B (95% acetonitrile, 10 mM ammonium formate, pH 8.0), using a 2-3 h gradient of 15-35% buffer B (Bai, B., et al., Methods Enzymol. 585: p. 377-95 (2017)). Up to 180 fractions were collected every minute for biofluid samples, and a total of 40 concatenated fractions were collected for cortex. In the acidic pH LC-MS/MS analysis, fractions were analyzed sequentially on a column (75 μm×15-30 cm, 1.9 μm C18 resin from Dr. Maisch GmbH, 65° C. to reduce backpressure) coupled with a Fusion or Q Exactive HF Orbitrap mass spectrometer (Thermo Fisher Scientific). Peptides were analyzed with a 1-3 h gradient (buffer A: 0.2% formic acid, 5% DMSO; buffer B: buffer A plus 65% acetonitrile). For mass spectrometer (MS) settings, positive ion mode and data-dependent acquisition were applied with one full MS scan followed by a 20 MS/MS scans. MS1 scans were collected at a resolution of 60,000, $1\times10^6$ AGC and 50 ms maximal ion time, higher energy collision-induced dissociation (HCD) was set to 32-38% normalized collision energy, —1.0 m/z isolation window with 0.3 m/z offset was applied, MS2 spectra were acquired at a resolution of 60,000, fixed first mass of 120 m/z, 410-1600 m/z, 1×105 AGC, 100-150 ms maximal ion time, and ~15 seconds of dynamic exclusion.

Protein Identification and Quantification by the JUMP Software Suite

The bioinformatics processing of protein identification and quantification were carried out with the JUMP software suite (Li, Y., et al., *Proteome Res,* 15(7): p. 2309-20 (2016); Shi, H., et al., Immunity. 51(6): p. 1012-1027 (2019); Wang, X., et al., *Mol Cell Proteomics* 13(12): p. 3663-73)). Briefly, MS/MS raw data were searched against a target-decoy database to estimate false discovery rate (FDR) (Peng, J., et al., J Proteome Res. 2: p. 43-50 (2003)). The downloaded Swiss-Prot, TrEMBL, and UCSC databases were combined and redundancy removed (human: 83,955 entries) to create the database. Main search parameters were set at precursor and product ion mass tolerance (±15 ppm), full trypticity, maximal modification sites (n=3), maximal missed cleavage (n=2), static mass shift including carbamidomethyl modification (+57.02146 on Cys), TMT tags (+229.16293 on Lys and N-termini), and dynamic mass shift for oxidation (+15.99491 on Met). Peptide spectrum matches (PSM) were filtered by mass accuracy, clustered by precursor ion charge, and the cutoffs of JUMP-based matching scores (J-score and AJn). The peptide was represented by the protein with the highest PSMs according to the rule of parsimony when one peptide is matched to multiple homologous proteins (Nesvizhskii, A. I. and R. Aebersold, Mol Cell Proteomics, 4(10): p. 1419-40 (2005)). Protein quantification was performed based on the reporter ions from MS2 using our previously optimized method (Niu, M., et al., *Anal Chem.* 89(5): p. 2956-63 (2017)).

Differential Expression Analyses of Proteome Datasets

Blood contamination is a major established covariate in tissue/biofluids proteome analysis, especially in serum/plasma (Geyer, P. E., et al., *EMBO Mol Med.* 11(11): p. e10427). Accordingly, a robust linear regression model for blood contamination correction was applied (Zhang, B., et al., Cell. 153(3): p. 707-20 (2013)). The residual was then used for the following differential expression analysis except for certain blood covariates (e.g. coagulation in serum proteome) that are biased in AD and control groups in the small cohorts of discovery proteomes. Blood contamination outlier samples were removed when biased blood covariates were detected. For instance, three outlier samples were removed in CSF due to erythrocyte contamination. Differential expression analyses of discovery proteomes were carried out via the LIMMA R package (Ritchie, M. E., et al., *Nucleic Acids Res.* 43(7): p. e47 (2015)), and multiple test correction was performed by Benjamini-Hochberg (BH) procedure (Benjamini, Y. and H. Y., *J R Stat Soc Series B.* 57: p. 289-300 (1995)). For individual proteome analysis, two cutoffs were applied, including Z score transformed $Log_2$ fold change >2 and FDR <0.05 or p value <0.05. For multiple proteome integration, Z score difference >2 and FDR <0.2 were used.

Principal Component Analysis

Principal component analysis (PCA) was used to visualize the differences among different sample groups in discovery proteomes. Log 2 transformed relative expression of all proteins was used as features of PCA. The pairwise Euclidean distance between features was calculated. PCA was performed using the R package prcomp (Ihaka, R. and R. Gentleman, R. *J. Comput. Graph. Stat.* 5(3): p. 299-314 (1996)).

Integrated Ranking of Proteins in Individual Datasets Though Order Statistics

To integrate multiple proteome datasets from distinct tissue/biofluids and independent studies to prioritize disease proteins and pathways in AD, a comprehensive order statistics-based protein ranking was carried out similarly as previously described (Bai, B., et al., *Neuron* (2020); Stewart, E., et al., *Cancer Cell.* 34(3): p. 411-426.e.19 (2018)), which combined N distinct sets of protein rankings to output one integrated ranking. Briefly, a total of 10 individual datasets from three independent deep proteomic studies were integrated for this analysis. The ranks of proteins were normalized by the total number of proteins in each dataset and the integrated protein ranking was generated by the framework of order statistics (Aerts, S., et al., *Nat Biotechnol.* 24(5): p. 537-44 (2006)); Zhang, J., et al., Nature. 481(7381): p. 329-34 (2012)). Specifically, the ranks of each data source were randomly permutated for 1,000 times to derive null Q values, and the empirical p values were then derived from the estimated null Q distribution. Multiple test was corrected by BH method. The integration was carried out in a 3-step tiered manner, discovery cohorts or reference cohorts were combined separately first. Proteomes of individual tissue/biofluids were then combined into cortex, CSF, or serum ranking. Finally, the three ranks were integrated into a final integrative rank. Pathway enrichment by GSEA (Subramanian, A., et al., *Proc Natl Acad Sci U.S.A.* 102(43): p. 15545-50 (2005)) was performed to summarize the integrated ranking into pathway rankings. The value and FDR were derived by permuting the proteins sets for 1,000 times in a core pathway extracted from GO, KEGG, and Hallmark. Pathways with FDR <0.05 were accepted as enriched pathways.

TOMAHAQ Targeted MS Validation Assay

The TOMAHAQ analysis was executed as described in Dey, K. K., et al., Clin Proteomics. 16: p. 16 (2019) using an established protocol (Erickson, B. K., et al., *Mol Cell.* 65(2): p. 361-370). The selected AK2 and PCK2 peptides were synthesized, purified, and labeled by a TMT0 reagent from Thermo Fisher Scientific, and were then spiked into the TMT11-labeled pooled samples with optimized quantities. These labeled synthetic and target peptide mixture were analyzed on an Orbitrap Fusion mass spectrometer following the same steps as described in Dey, K. K., et al., Clin Proteomics. 16: p. 16 (2019). Acquired targeted MS3 level quantification were compared with the original discovery MS analyses. Finally, Pearson correlation between the TOMAHAQ and the discovery MS assays were carried out to confirm the validity of these biomarker candidates.

ELISA Validation Assay

GPNMB protein levels in the CSF samples from 7 AD and 7 healthy controls were detected by human Osteoactivin (GPNMB) ELISA kit (RayBiotech, US). CSF samples were diluted 3-fold with the diluent buffer before the assay. ELISA were carried out in accordance with the manufacturer's manual. Student T test was applied for the DE analysis between AD and Ctl groups, and Pearson correlation was performed to compare the quantification between ELISA and the discovery MS assay.

Example 1: Comprehensive Integration of Ultra-Deep AD Proteomes in Cortex, CSF and Serum To systematically investigate AD biofluid biomarkers that are associated with AD pathogenesis, comprehensive integrated analyses of 10 independent AD proteomic datasets covering 5 ultra-deep discovery datasets and 5 deep reference datasets from brain cortex, CSF and serum was performed (Table 1). The cortex proteome consists of 2 discovery cohorts and 2 reference cohorts. The CSF proteome consists of 1 discovery cohort and 3 reference cohorts. The 5 reference datasets were mined from 2 independent biofluid proteome studies of AD (Higginbotham, L., et al., bioRxiv. p. 10.1101/806752 (2019); Sathe, G., et al., *Proteomics—Clinical Applications*: p. 1800105 (2019)). The integrative analyses were carried out via a CSF-centered manner, and datasets were assigned with labels from i to x (Table 1, FIG. 1A). In total, 17,541 proteins (13,254 genes) from 365 AD, MCI and healthy control cases (FIG. 1A) were analyzed, representing the most comprehensive AD proteomic data to date.

The proteomic data quality of the 5 discovery datasets from cortex, CSF and serum were first examined (data not shown). The AD and control samples were distinguishable by principle component analysis of the entire proteomic datasets (FIG. 1B). The profiling depth of these proteomic datasets were subsequently examined. Ultra-deep proteomic profiling depth was achieved through a newly established pipeline, which combines un-depleted biofluid sample processing, multiplexed tandem-mass-tag labeling, extensive two-dimensional liquid chromatography fractionation and high-resolution tandem mass spectrometry (termed TMT-LC/LC-MS/MS) (Dey, K. K., et al. *Clin Proteomics,* 16: p. 16 (2019); Bai, B., et al., Neuron (2020)). As a result, the cortex proteome (13,833 proteins from cortex datasets i and ii) described herein covers 86% of the expressed cortex transcriptome based on the human protein atlas database (Erickson, B. K., et al., *Mol Cell.* 65(2): p. 361-370 (2017)) (FIG. 1C). The CSF discovery proteome (5,941 proteins in dataset v) described herein covers 80% and 86% of reference 1 (2,731 proteins in dataset vi) and reference 2 (2,025 proteins in dataset viii), respectively, while the references 1 and 2 cover only 37% and 29% of the CSF proteome. Similarly, the serum discovery proteome described herein was compared with two recent AD serum proteome studies (Ashton, N. J., et al., *Sci Adv.* 5(2): p. eaau7220 (2019); Lan, J., et al., *J Proteome Res.* 17(4): p. 1426-35 (2018)). The dataset described herein (4,826 proteins in dataset x) covers 63% and 89% of the two reference datasets (560 and 510 proteins), respectively, while the reference datasets cover only 7% and 9% of the proteome described herein (FIG. 1D). Considering the low coverage of the two human serum datasets, the two human serum datasets were not used in the analysis described herein. Together, these comparisons confirm the high quality of the analyzed proteomes described herein, highlighting the deep coverage of the AD tissue/biofluid proteomes.

Figures 2A, 2B:
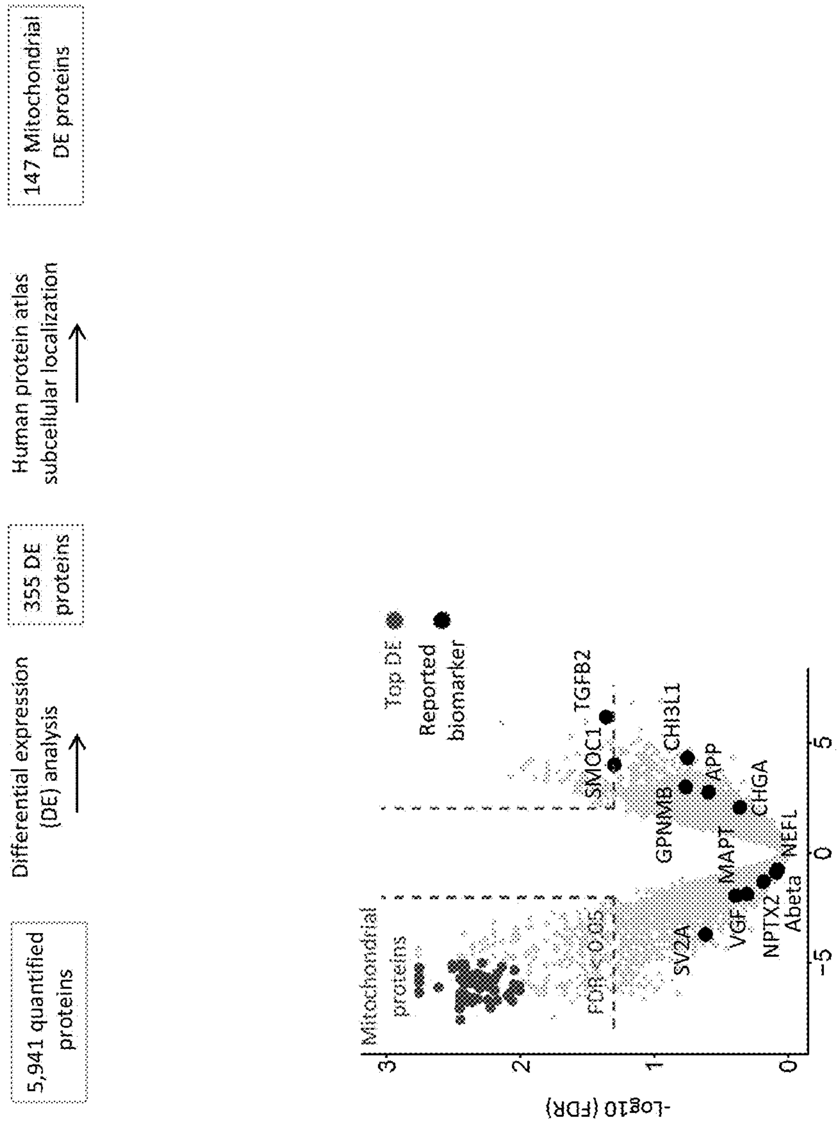
FIG. 2A depicts the workflow for the CSF proteome analysis.
FIG. 2B demonstrates that the ultra-deep CSF proteome identified decreases of mitochondrial proteins in Alzheimer's disease. The x-axis of the volcano plot for all quantified CSF proteins showed the Z score transformed log 2 level fold changes comparing AD to Ctl. The y-axis shows the −log 10 level FDR value. Previously reported AD CSF biomarkers are plotted in black. Top DE proteins with FDR <0.01 and Z value <−5 are plotted in red. Red dashed lines indicate the DE cutoff of FDR <0.05 and Z score difference >2.
Figure 2C:
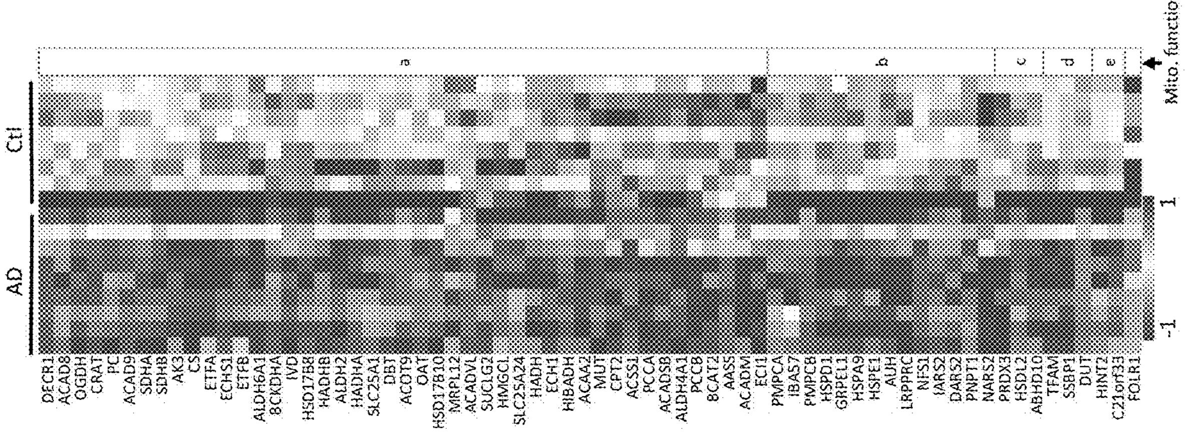
FIG. 2C shows the majority of the top DEs are mitochondrial proteins are characterized by decreased levels in AD. Heatmap shows the relative expression of the top DE proteins with Z score difference >5 and FDR <0.01 comparing AD to Ctl, these DE proteins are classified into distinct groups (a-e) according to their mitochondrial functions as indicated on the right side of the heatmap.
Figure 2D:
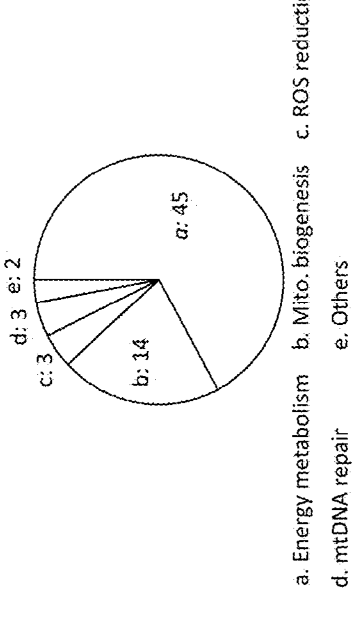
FIG. 2D shows a pie plot depicting the mitochondrial functional groups classified in panel c. The number of proteins in each subgroup is labeled.

Example 2: Ultra-Deep CSF Proteome Profiling Identifies Evident Mitochondrial Protein Reduction in Alzheimer's Disease AD CSF biomarkers have been extensively explored in shallow coverage due to technical challenges. Although many biomarkers have been proposed, most are not reproducible across laboratories. To explore novel AD biomarker candidates in an ultra-deep proteome setting, the in-depth biofluid profiling pipeline (Dey, K. K., et al. *Clin Proteomics,* 16: p. 16 (2019)) was applied to the analysis of 20 CSF samples. In total, 5,941 unique proteins were quantified with a false discovery rate (FDR) of 1% in 10 AD and 10 healthy control cases. Three sample outliers were removed due to blood contamination. DE analysis was carried out through LIMMA R package, resulting in 355 DE CSF proteins (Z value of $\log_2$Ratio >2 and FDR <0.05, FIG. 2A). The ultra-deep CSF proteome described herein identified most of the previously reported AD CSF biomarker candidates (12 out of 13, data not shown), however, the majority of these biomarker candidates displayed no statistical significance except for SMOC1 and TGFB2, which may be due to the small sample size in the pilot study and/or the small changes of these proteins in AD (FIG. 2B). Nevertheless, 60 top DE proteins were observed, even under a highly stringent threshold (Z value >5 and FDR <0.01). Remarkably, 59 out of the 60 top DE proteins are mitochondrial proteins (FIGS. 2B and 2C), and most of these are tightly correlated with the others (data not shown). These proteins are known to have functional roles in supporting energy metabolism, mitochondrial biogenesis, reactive oxygen species reduction, and mt DNA repair (FIG. 2D).

Figure 2E:
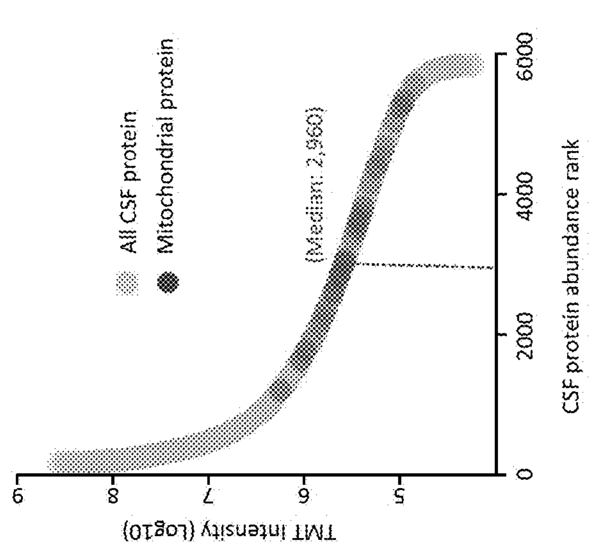
FIG. 2E demonstrates that deep profiling depth is a prerequisite for confident detection of evident mitochondrial protein changes. CSF proteins are plotted as a function of concentration rank (x-axis) and mean log 10 level TMT intensity in all samples (y-axis). Top DE mitochondrial proteins with Z score difference >5 and FDR <0.01 were plotted in red. The median concentration rank of these mitochondrial proteins is labeled and marked by dashed red line.

This correlated mitochondrial protein decrease in AD is striking but unreported in previous CSF studies. To understand why these proteins are not previously identified, all quantified proteins were ranked according to their abundance, and it was observed that these top DE mitochondrial proteins were present in the CSF at low abundance, with a median abundance rank of 2,960 (FIG. 2E). Systematic investigation of the DE proteins was then performed using distinct proteome coverage. If the coverage is as shallow as the depth of 500 proteins, it is sufficient to detect many previously reported AD biomarker candidates but will miss all of these top mitochondrial DE proteins. While a small fraction of these mitochondrial proteins start was observed with the depth of 2,000-3,000 proteins, the majority of these proteins were observed with the depth of at least 4,000 proteins (data not shown). Thus, ultra-deep profiling depth is a prerequisite for detection of protein changes in the AD CSF proteome. In summary, the CSF proteomic analysis described herein covers most of the previously reported AD CSF biomarkers and identifies evident mitochondrial protein reduction in the AD patients.

Figure 3E:
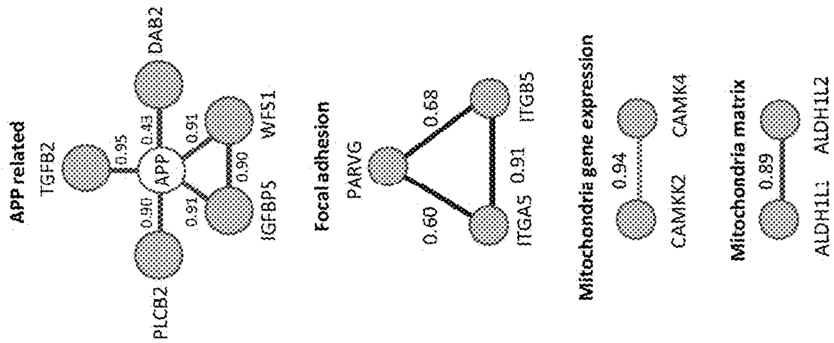
FIG. 3E shows the integration of the DE proteins and protein-protein interaction (PPI) database unveils enrichment of amyloid pathology and mitochondrial functions. Protein-protein interaction modules were derived from superimposing the 44 DE proteins along with APP and TAU on STRING PPI database. The interaction modules were built based only on the most confident interaction sources including experiments and database. The default statistic criteria of STRING with a cutoff of minimum interaction score of 0.4 was applied to derive PPI modules. The pairwise PPI interactions scores are displayed next to the edges.

Example 3: Integration of CSF and Cortex Proteomes Discovers Consistent CSF Biomarkers in Alzheimer's Disease Across Independent Studies To investigate CSF protein changes associated with AD pathology, 4 cohorts of cortex and 4 cohorts of CSF datasets from three independent MS-based proteome profiling studies were systematically integrated (FIG. 3A). The cortex proteome covered majority of proteins quantified in the CSF (FIG. 3B). A cutoff (Z value >2 and FDR <0.2) was applied for all datasets, resulting in 1,261 DE proteins in the CSF and 245 DE proteins in the cortex, 44 out of these were changed in both proteomes (FIGS. 3B-3D), with most of them showing increases in both cortex and CSF (e.g. TGFB2, IGFBP5, and SLC5A3) or an increase in the cortex but a decrease in CSF (e.g. DPYD and S100A4, similar to the expression pattern of A1342 peptide (Hansson, O., et al., Alzheimers Res Ther. 11(1): p. 34 (2019)). Interestingly, MDK, CTHRC1, and Aβ, which were reported as the most significantly elevated proteins in an AD brain cortex study (Bai, B., et al., *Neuron* (2020)), were not significantly changed in the small cohort of CSF samples (FIG. 3C). Superimposing these 44 proteins along with APP and TAU onto STRING protein-protein interaction database (Szklarczyk, D., et al., *Nucleic Acids Res.* 43: p. D447-52 (2015)) elucidated 4 protein interaction modules associated with amyloid pathology and mitochondrial functions, while no TAU related protein interaction module was identified with this small list (FIG. 3E). Notably, most of these module proteins are correlated with the amyloid level (data not shown).

Figure 3D:
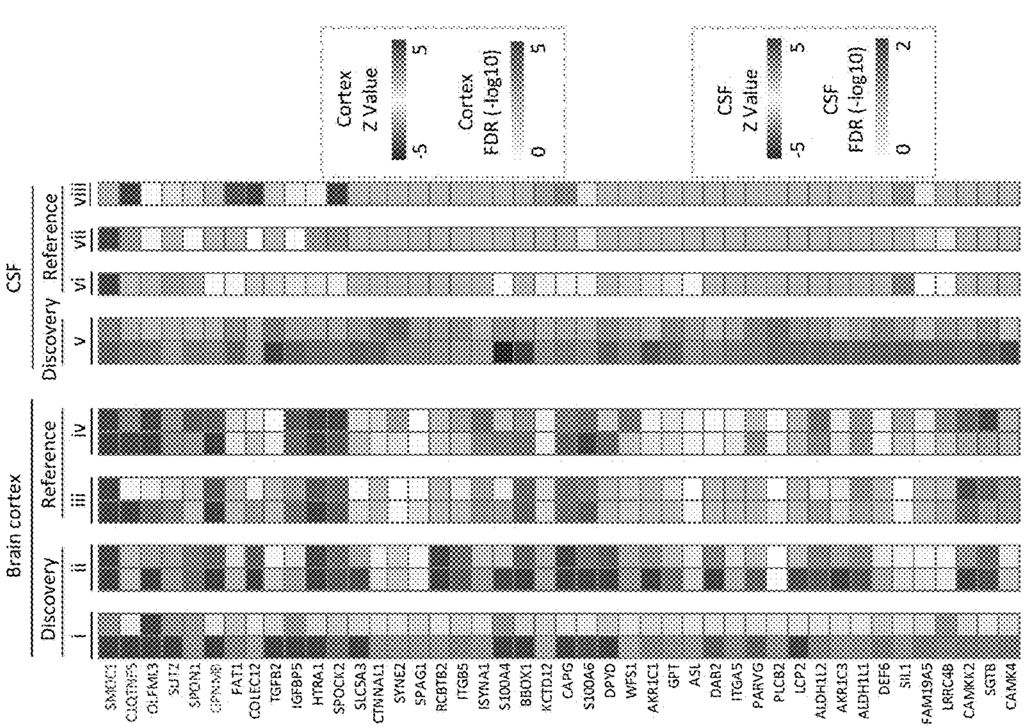
FIG. 3D depicts heatmap showing Z score transformed log 2 level fold changes and −log 10 FDR values of the 44 DE proteins comparing AD to control in the cortex and the CSF proteome datasets.
Figure 4A:
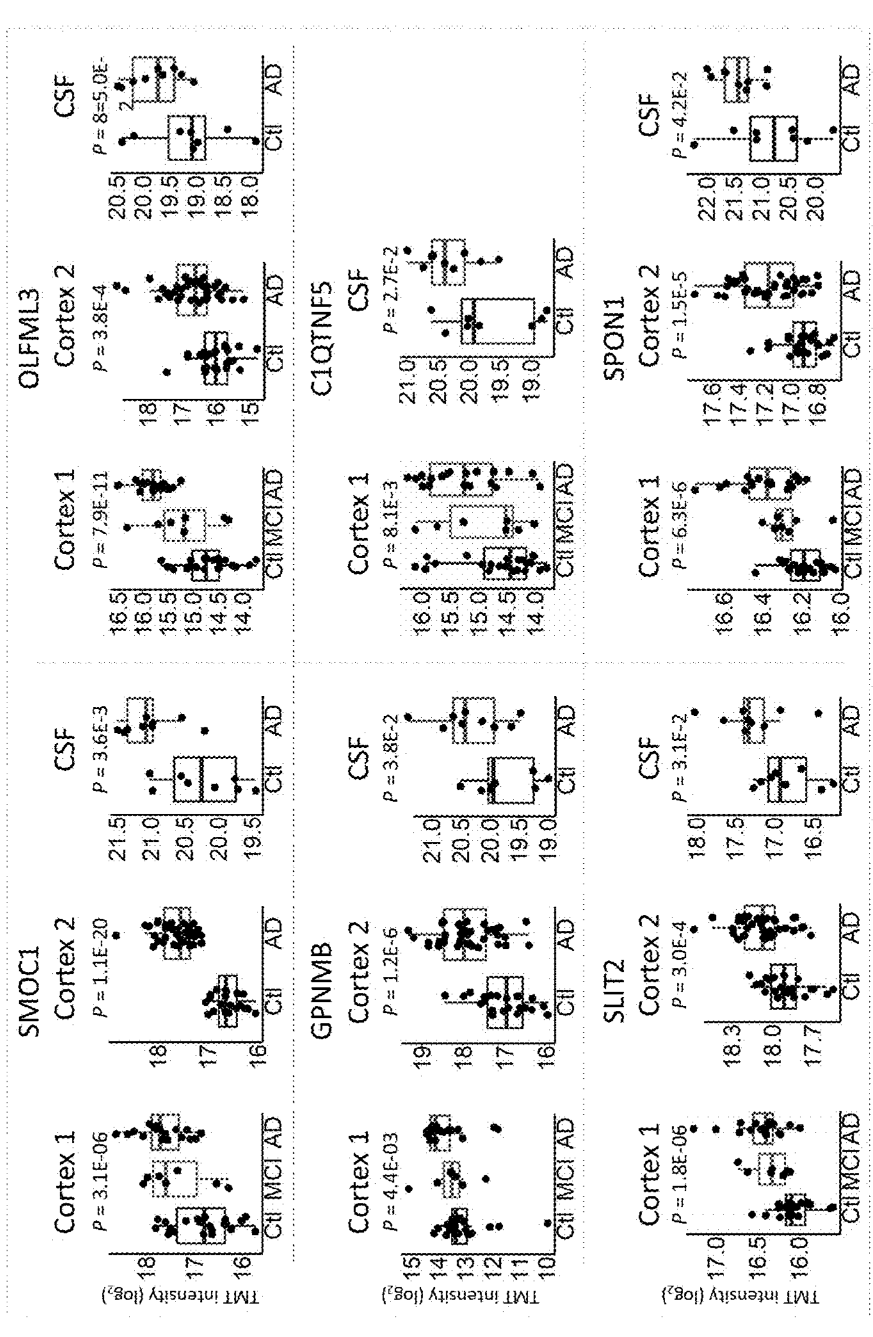
FIG. 4A depicts dot plots overlaid onto boxplots showing the expression levels of biomarker candidates that are consistently detected in at least two independent MS-based AD CSF proteome studies in the cortex and the CSF proteomes. The p values of the DE analyses between AD and healthy control are displayed on the top of the plots. DE analyses were performed through the LIMMA R package. The x-axis shows sample groups and the y-axis indicates Log 2 transformed TMT intensity. Boxplot center line, median; box limits, upper and lower quartiles; whiskers, 1.5× interquartile range; points, expression levels of each individual samples.
Figure 4B:
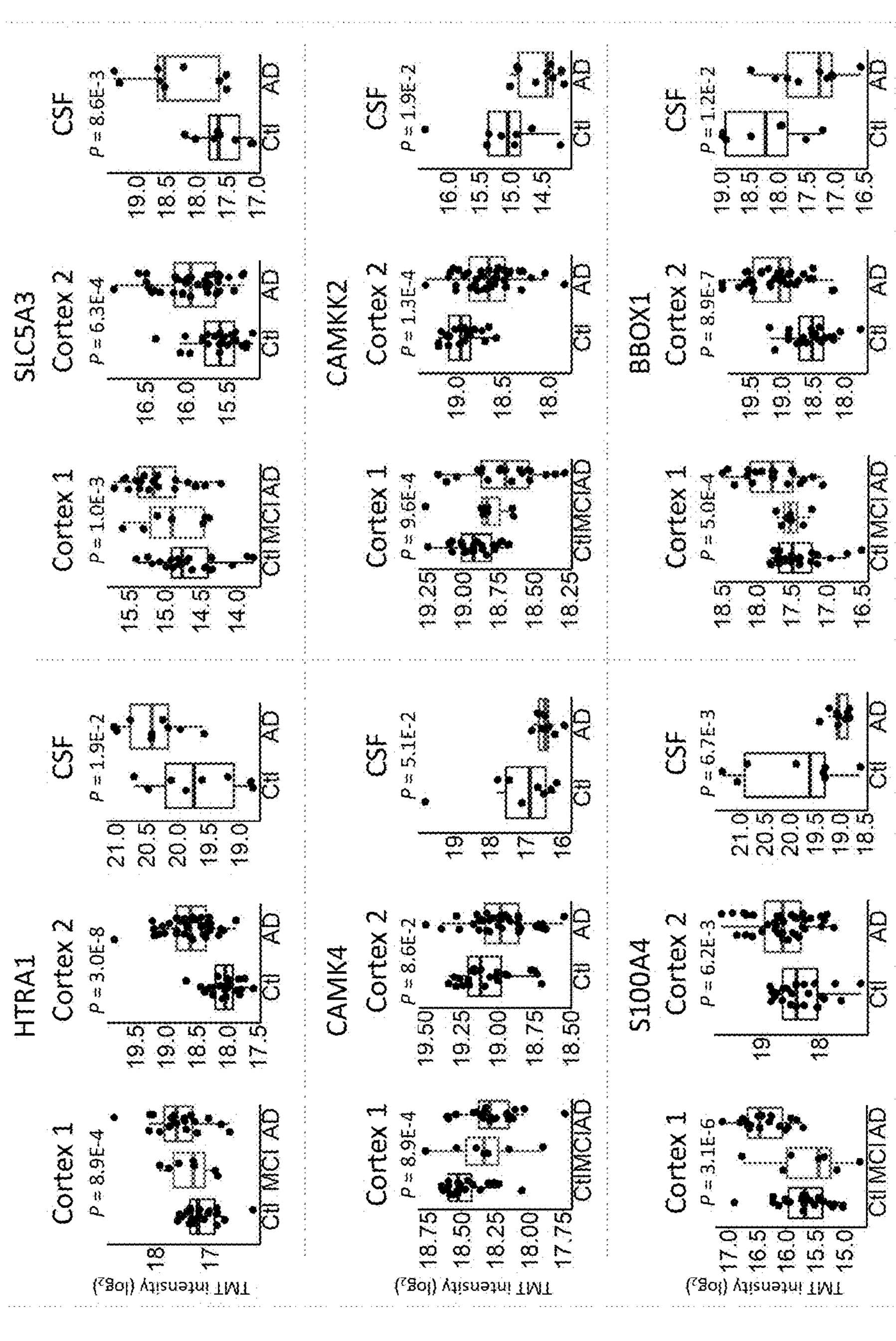
FIG. 4B shows dot plots overlaid onto boxplots showing expression levels of novel biomarker candidates detected in our ultra-deep proteome in the cortex and the CSF datasets. The p values of the DE analyses between AD and healthy control are displayed on the top of the plots. DE analyses were performed through the LIMMA R package. The x-axis shows sample groups and the y-axis indicates Log 2 transformed TMT intensity. The boxplot center line, median; box limits, upper and lower quartiles; whiskers, 1.5× interquartile range; points, expression levels of each individual samples.

To evaluate the reliability and reproducibility of these 44 DE proteins across laboratories, the CSF proteome described herein was compared with two independent MS-base CSF proteomic studies (Higginbotham, L., et al., bioRxiv. p. 10.1101/806752 (2019); Sathe, G., et al., *Proteomics—Clinical Applications*. p. 1800105 (2019)). SMOC1 and C1QTNF5 was observed in all three independent studies. OLFML3, SPON1, and SLIT2 were notable in the analysis described herein and in reference study 1 (data vi) (Higginbotham, L., et al., bioRxiv. p. 10.1101/806752 (2019)). GPNMB was observed in this study and reference study 2 (data viii) (Sathe, G., et al., *Proteomics—Clinical Applications*. p. 1800105 (2019)) (FIGS. 3C and 3D). All six proteins were reported to be tightly associated with AD pathogenesis (Bai, B., et al., Neuron (2020)]. While, SMOC1 and GPNMB have been reported as putative CSF biomarkers in previous studies, C1QTNF5, OLFML3, SPON1 and SLIT2 are novel candidates described herein that show reproducibility across distinct laboratories and pipelines (e.g. depletion vs un-depletion CSF). Notably, the expression level of all six proteins started to increase in the cortex of mild cognitive impairment patients, implicating their potential as early diagnosis biomarkers for Alzheimer's disease (FIG. 4A). Moreover, the CSF proteome profiling described herein also identified potential AD biomarkers of low abundance that were beyond the detection limits of other studies. For example, the abundance rankings of SLC5A3, BBOX1, CAMK4, and CAMKK2 in the CSF were 3,039, 3,040, 4,191, and 5,787, respectively, all beyond the detection limits of previously reported studies (FIGS. 3D and 4B). The levels of CAMK4 and CAMKK2 were decreased in both the cortex and CSF. Finally, HTRA1, a possible genetic risk factor for AD, and an enzyme that degrades ApoE4 and APP, was also identified as a novel DE protein in the CSF proteome described herein (FIG. 4B). Collectively, the integration of CSF and cortex proteomes identified consistent CSF biomarker candidates in AD.

Figures 5D, 5E:
FIG. 5D shows the expression levels of representative mitochondrial DE proteins in the human cortex, the human CSF and the mouse CSF. Dot plots overlaid onto boxplots showing expression of representative DE proteins in panel c and d. The p values of the DE analyses between AD and healthy control are displayed on the top of the plots. DE analyses were carried out through the LIMMA R package. The x-axis shows sample groups and the y-axis indicates Log 2 transformed TMT intensity. Boxplot center line, median; box limits, upper and lower quartiles; whiskers, 1.5× interquartile range; points, expression levels of each individual samples.
FIG. 5E shows the expression levels of the representative top DE proteins in human cortex and mouse CSF. Dot plots are overlaid onto boxplots showing expression of representative DE proteins in panel c and d. The p values of the DE analyses between AD and healthy control are displayed on the top of the plots. The DE analyses were performed through the LIMMA R package. The x-axis shows sample groups and the y-axis indicates Log 2 transformed TMT intensity. Boxplot center line, median; box limits, upper and lower quartiles; whiskers, 1.5× interquartile range; points, expression levels of each individual samples.

Example 4. Integration of Human and Mouse CSF Proteomes Identifies Consistent Mitochondrial Protein Decrease in Alzheimer's Disease CSF biomarkers that are conserved in human and mouse models are valuable for the AD community to explore AD-related molecular mechanism. Proteomic analysis was conducted to identify Aβ-induced protein changes in CSF from 5×FAD mouse, in which mutant APP and PSEN1 are overexpressed to generate a high level of Aβ peptide. An 11-plex TMT-LC/LCMS/MS analysis (6 samples from 5×FAD and 5 samples from age-matched wild type mice) allowed the quantification of 1,056 mouse CSF proteins, with 85 DE proteins (Z value >2 and p value <0.05, FIGS. 5A and 5B). 11 out of these 85 proteins were overlaid with the human CSF DE proteins (FIG. 5C). Strikingly, more than 50% of these consistent DEs are from mitochondria, suggesting that mitochondrial dysfunction is highly conserved in AD and the 5×FAD mouse. Many of these mitochondrial proteins were changed in the AD cortex with an expression pattern similar to Aβ42 peptide (i.e. increase in cortex and decrease in CSF), such as HADHA and CYB5R3 (FIGS. 5C and 5D). C4B and SPP1, which are known to be tightly associated with AD pathogenesis, were discovered to be among the top DE proteins in the mouse CSF (FIG. 5B). The increase of C4B and SPP1 in the AD cortex was detected, but the data failed to demonstrate their significant changes in the small human CSF cohort described herein (FIG. 5E). In summary, the integrative analysis of mouse and human CSF elucidated Aβ-induced protein changes in mouse CSF and demonstrated consistent mitochondrial disorder in AD in both human and mouse CSF.

Example 5. Integration of CSF, Serum, and Cortex Proteomes Indicates Consistent Mitochondrial Signatures in Alzheimer's Disease Compared with CSF biomarkers, blood-based biomarkers are more promising for first-line diagnosis and are urgently needed. Systematic comparison of the CSF, serum and cortex proteomes were performed to investigate AD pathogenesis signatures. An ultra-deep serum profiling of 6 AD and 5 healthy control cases was performed to quantify 4,826 unique proteins (Dey, K. K., et al., Clin Proteomics. 16: p. 16 (2019)). As the serum samples may be contaminated with proteins from red blood cells, this variable was first corrected using a linear regression model-based approach (Zhang, B., et al., Cell. 153(3): p. 707-720 (2013)), and then defined 396 DE proteins (Z value >2 and p value <0.05). Comparison with DE proteins in CSF and cortex led to 94 DE proteins in serum and cortex, 107 DE proteins in serum and CSF, and 37 proteins in all three layers of proteomes. Notably, 22 out of these 37 proteins are mitochondrial proteins (FIG. 6A), highlighting mitochondrial changes as the most consistent AD signature across cortex, CSF and serum.

Figure 6B:
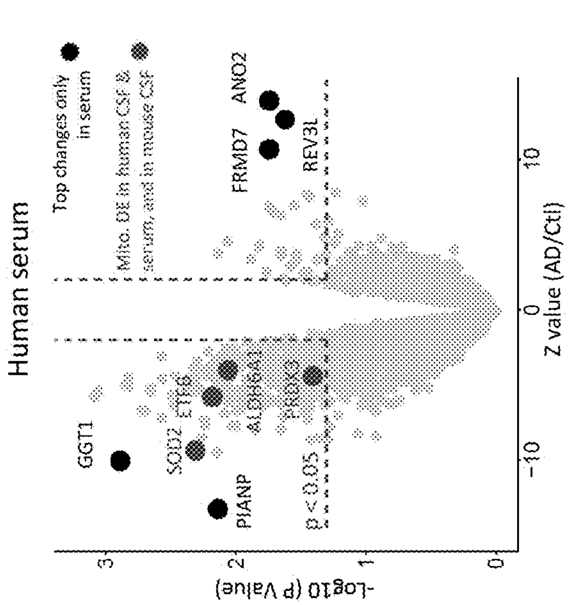
FIG. 6B demonstrates that the deep serum proteome analysis identifies decreases of mitochondrial proteins. The x-axis of the volcano plot shows the Z score transformed log 2 fold change comparing AD to Ctl and the y-axis indicates −log 10 p value. The top DE proteins in the serum are plotted in black and labeled. Proteins that are differentially expressed in human CSF, mouse CSF, and human serum proteomes are plotted in red and labeled. The red dashed lines indicate the DE cutoff of p value <0.05 and Z value difference >2.
Figure 6A:
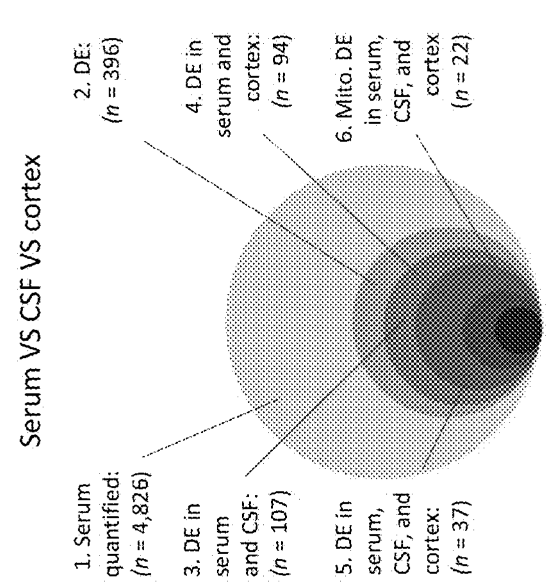
FIG. 6A depicts a summary of the DE analysis of the serum proteome and its integration with the CSF and the cortex proteome. 4,826 proteins were quantified in AD serum samples. 395 proteins were identified as differentially expressed proteins with a Z-score transformed log 2 fold difference >2 and p value <0.05. 107 out of these proteins are differentially expressed in both serum and CSF proteomes, 94 of these proteins are differentially expressed in both serum and brain proteomes, 37 proteins are differentially expressed in the serum, the CSF, and the cortex proteomes. 22 out of the 37 DE proteins are mitochondrial proteins.
Figure 6D:
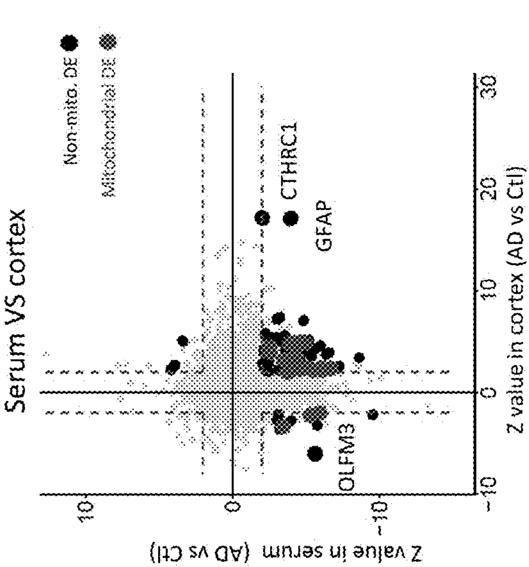
FIG. 6D shows the integration of serum and cortex proteomes unveils mitochondrial protein changes and amyloid-correlated protein panel. Proteins that are quantified in both serum and cortex are plotted as a function of their Z value change comparing AD to Ctl in cortex (x-axis) and in serum (y-axis). 70 non-mitochondrial DE proteins with Z value difference >2 and FDR <0.2 in cortex or p value <0.05 in serum were plotted in black. Three top DE proteins that were reported in the amyloid-correlated protein panel in previous cortex study were labeled. 24 mitochondrial DE proteins are plotted in red. Red dashed lines indicate Z value difference >2 in serum and cortex.
Figure 6C:
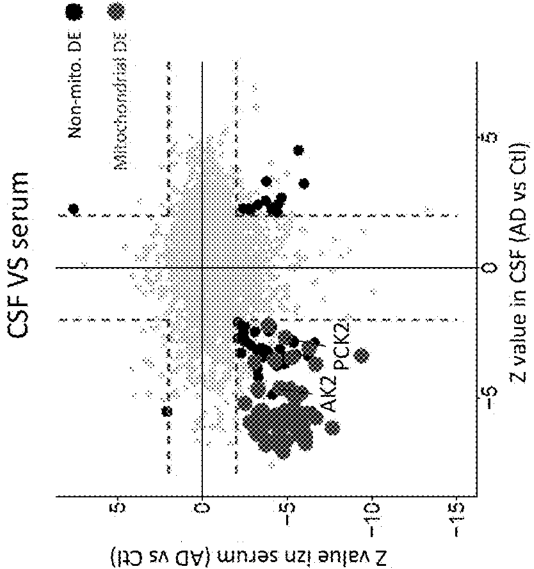
FIG. 6C shows the integration of the serum and the CSF proteomes identifies consistent and massive mitochondrial protein decrease. Proteins that are quantified in both serum and CSF are plotted as a function of their Z values comparing AD to Ctl in CSF (x-axis) and in serum (y-axis). 55 non-mitochondrial DE proteins with Z value difference >2 and FDR <0.2 in CSF or p value <0.05 in serum are plotted in black, and 52 mitochondrial DE proteins are plotted in red. The identity of two mitochondrial proteins that were applied for TOMAHAQ targeted MS assay (see FIG. 8) were labeled. The red dashed lines indicate Z value difference >2 in CSF and serum.
Figure 6E:
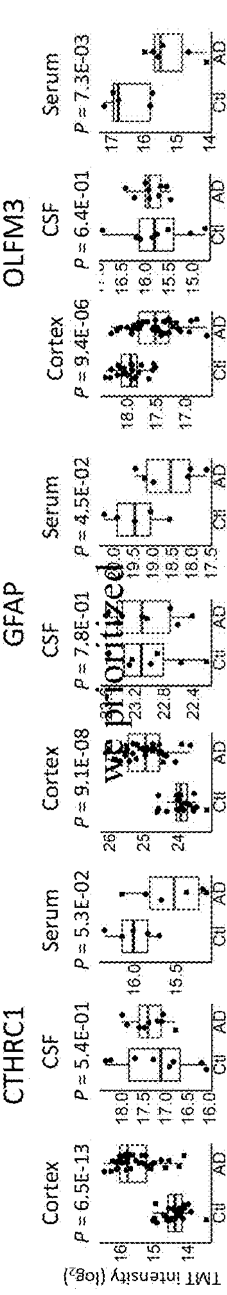
FIG. 6E depicts the expression levels of representative DE proteins in cortex and serum. Dot plots overlaid onto box-plots showing expression of representative DE proteins in cortex, CSF, and serum proteomes. The p values of the DE analyses between AD and healthy control are displayed on the top of the plots. The DE analyses were performed through the LIMMA R package. The x-axis shows sample groups and the y-axis indicates Log 2 transformed TMT intensity. Boxplot center line, median; box limits, upper and lower quartiles; whiskers, 1.5× interquartile range; points, expression levels of each individual samples.

The DE analysis in serum identified several AD relevant changes among the top DE proteins (e.g. GGT1 and ANO2) (FIG. 6B). Interestingly, 4 out of the 6 mitochondrial proteins that were decreased in AD in both human and mouse CSFs were also reduced in the AD serum (i.e. ALDH6A1, ETFB, SOD2, and PRDX3), highlighting the robustness as the AD biofluid signature (FIG. 6B). Proteins that were differentially expressed in both CSF and serum were subsequently investigated. 52 out of a total of 107 DE proteins were mitochondrial proteins and demonstrated decreased levels in AD in both serum and CSF (FIG. 6C). All of the 94 DE proteins in the serum and cortex were further examined and it was demonstrated that most of these proteins were increased in the cortex and decreased in the serum, including 21 mitochondrial proteins (FIG. 6D), which is reminiscent of the distribution pattern of Aβ peptides (high in cortex and low in serum in AD cases) (Janelidze, S., et al., *Scientific reports*. 6: p. 26801-26801 (2016)). The accumulation of proteins in the cortex may be, at least partially, due to prominent protein aggregation in the brain. Interestingly, an AD-correlated protein panel of CTHRC1, GFAP and OLFM3 in the brain were revealed as top DE proteins in AD serum (FIGS. 6D and 6E). Together, the integrated analysis demonstrates mitochondrial protein changes were the most consistent AD signature carried over from brain cortex to CSF and serum.

Figure 7A:
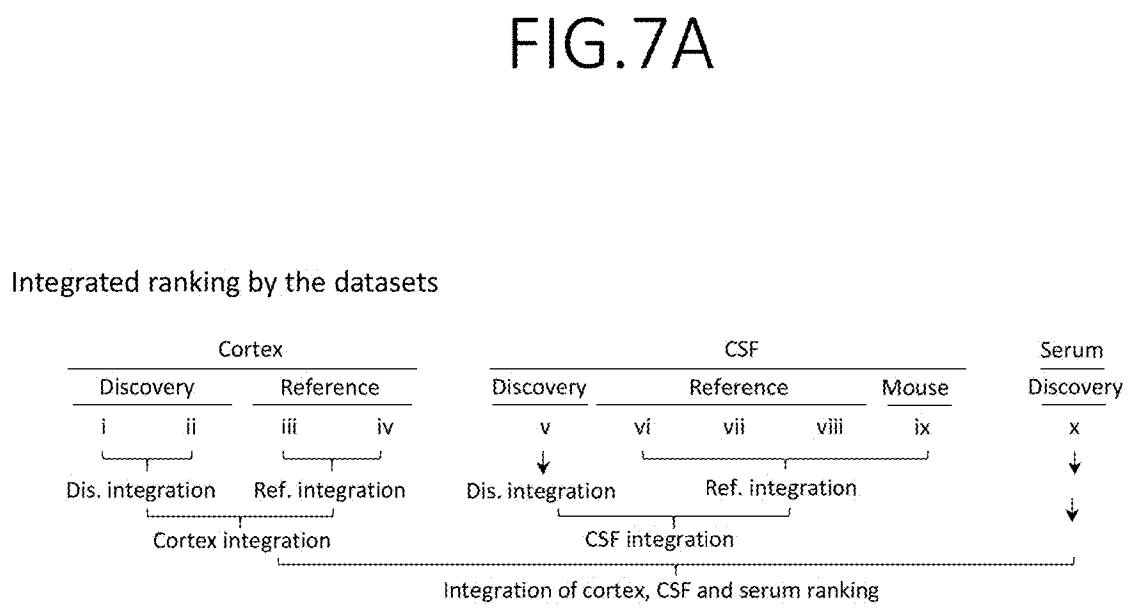
Figure 7C:
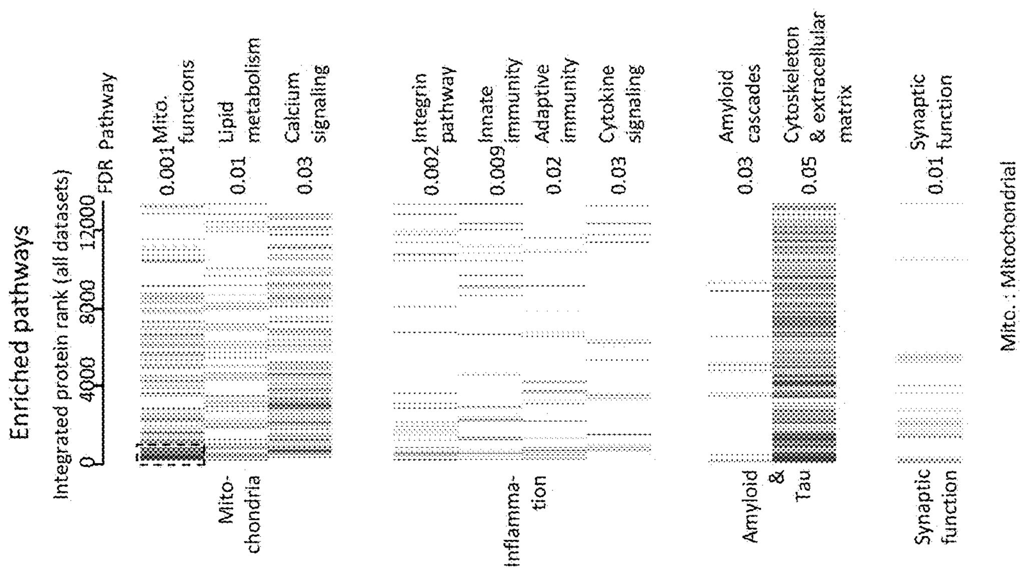
FIG. 7C shows mitochondrial function is the most significantly enriched pathway in the integrated ranking. Pathways are enriched by GSEA and further categorized into four groups. The barcode plots represent the positions of proteins in the sorted integrated ranking.
Figure 7B:
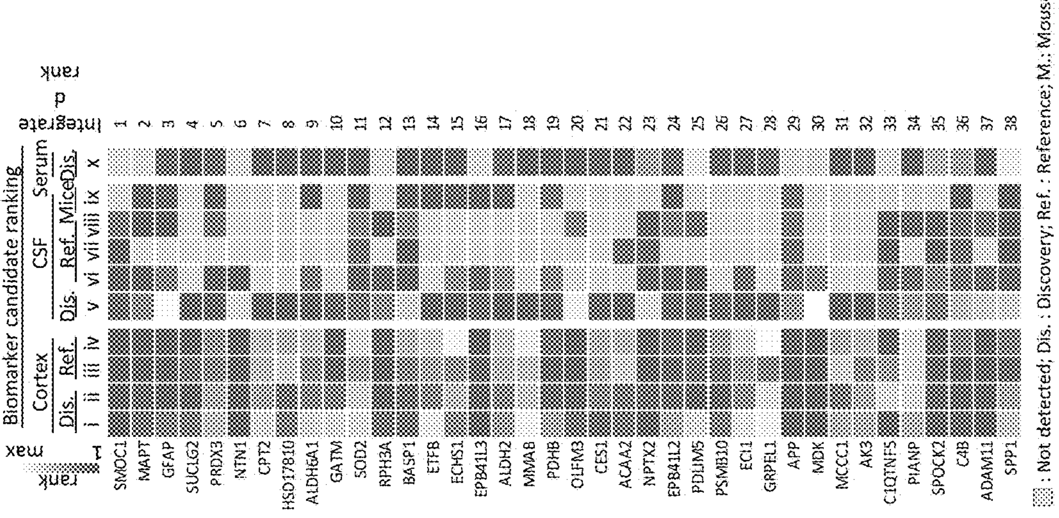
FIG. 7B shows the top proteins signatures of Alzheimer's disease prioritized through the integrated ranking. Heatmap shows the ranking of top AD signature proteins with a final integrated ranking p value <0.001 in each of the ten datasets. Protein ranks are labeled on the right side of the heatmap. The rankings of proteins are shown by boxes of two-color gradients, with missing values indicated by grey boxes.
Figure 8B:
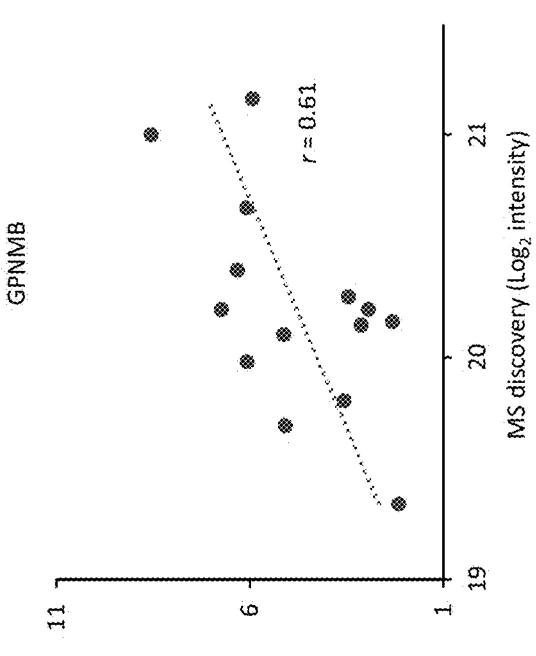
FIG. 8B shows a scatter plot depicting the correlation between the ELISA and the discovery MS data. Pearson correlation coefficient (r) is displayed. The x-axis shows the Log 2TMT ion intensities of GPNMB quantified by MS. The y-axis indicates the CSF concentration of GPNMB (ng/ml) quantified by ELISA.
Figure 8A:
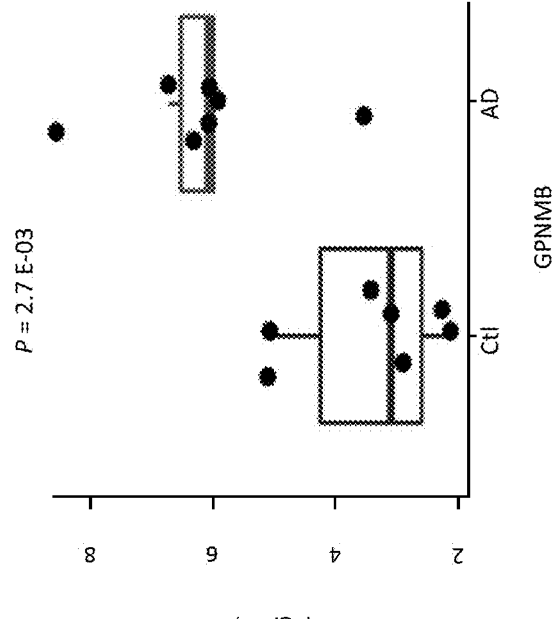
FIG. 8A shows the validation of MS discoveries by ELISA assay. Dots overlaid onto box-plots showing expression level of the AD biomarker candidate GPNMB in CSF quantified by ELISA assay. 7 healthy control and 7 AD samples were analyzed. The p value of the DE analysis between AD and healthy control by Student's t-test is displayed on the top of the plots. The x-axis shows the sample groups and the y-axis indicates the ELISA measurement of GPNMB concentration in CSF (ng/ml). Boxplot center line, median; box limits, upper and lower quartiles; whiskers, 1.5× interquartile range; points, expression levels of individual samples.
Figure 8C:
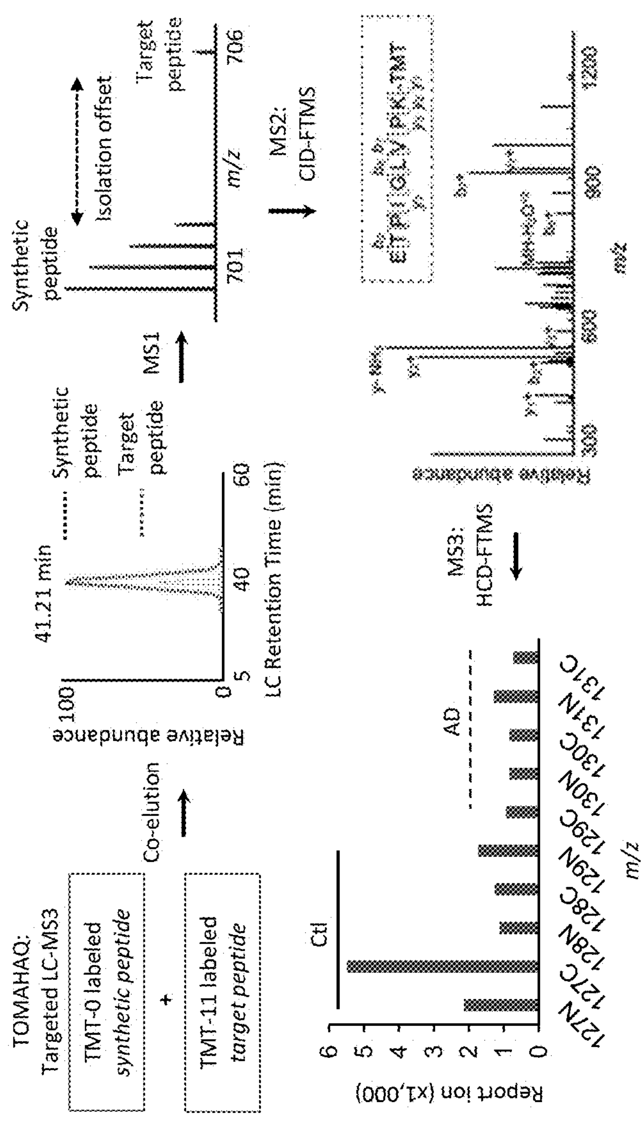
FIG. 8C shows the workflow for the TOMAHAQ targeted MS validation assay. A synthetic trigger peptide was spiked into the mixture of multiplexed samples to validate the quantification of a candidate biomarker peptide. The synthetic peptide and native peptide were co-eluted, and the synthetic peptide was presented at high concentration, triggering the MS instrument to quantify the native peptide by MS3 using a predefined isolation offset. MS3 ions were produced by pre-determined y or b ions from targeted MS2 spectra, and the resulting reporter ions were applied for the quantification of the targeted biomarker candidate.
Figures 8D, 8E, 8F:
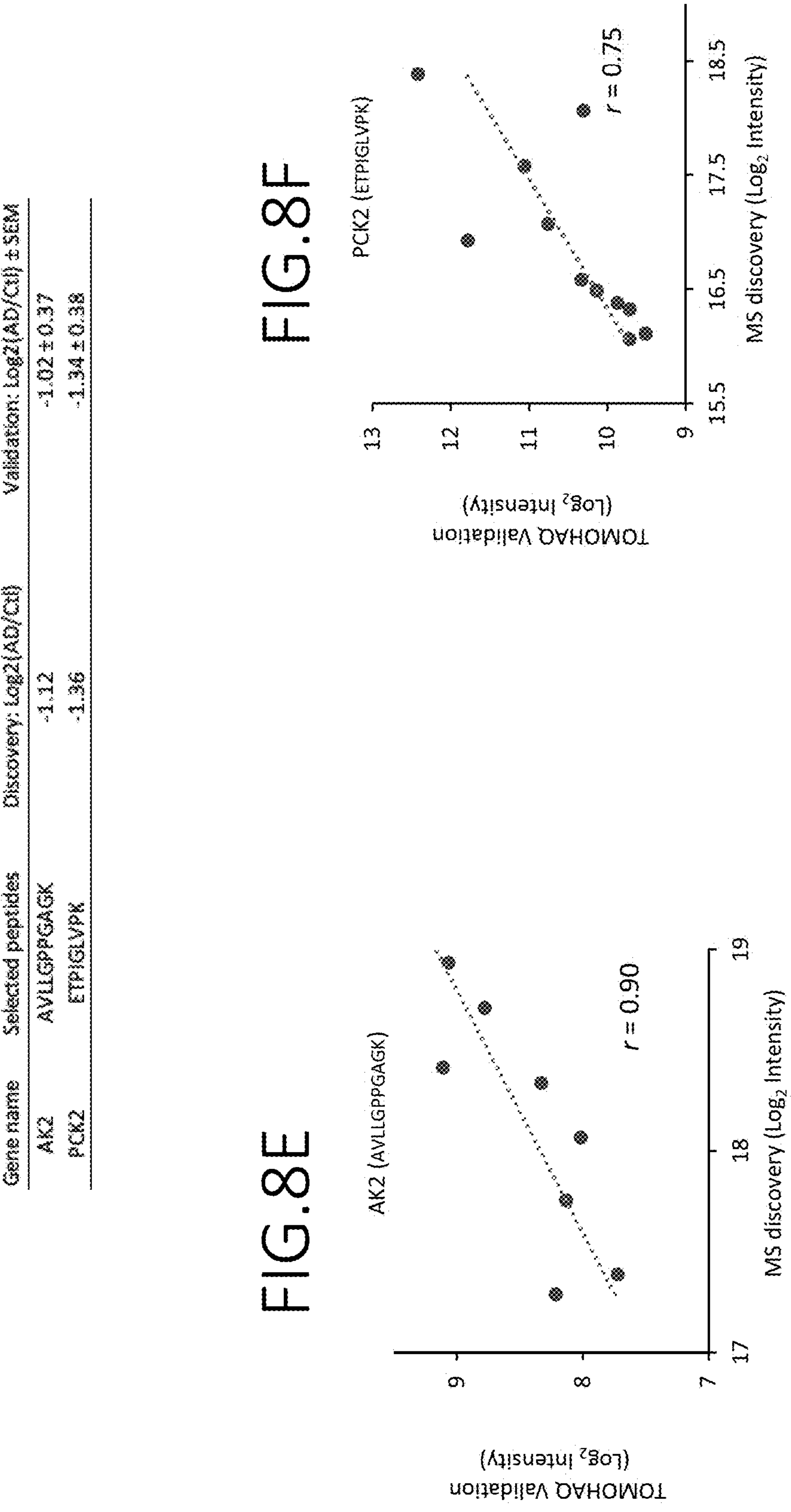
FIG. 8D shows a comparison of the TOMAHAQ results and the discovery MS data.
FIG. 8E shows scatter plots show the correlations between the TOMAHAQ and the discovery MS results of AK2 in the in human CSF samples. Pearson correlation coefficient (r) are displayed. The x- and y-axes indicate the $Log_2$ TMT intensities from the discovery MS and TOMAHAQ assay, respectively.
FIG. 8F shows scatter plots show the correlations between the TOMAHAQ and the discovery MS results of PCK2 in the in human CSF samples.

Example 6. Integrating the Rankings of Ten Individual Datasets Through Order Statistics Prioritizes Top AD Protein Signatures Integration of multiple dimensions of data has proven powerful for prioritizing core disease proteins and pathways. As described herein, datasets were combined from distinct AD tissue/biofluids and independent studies to rank disease proteins and pathways using order statistics (Aerts, S., et al., Nat Biotechnol. 24(5): p. 537-44 (2006)) and gene set enrichment analysis (GSEA). The integration was performed in a 3-step manner. Specifically, discovery cohorts or reference cohorts were separately combined. Proteomes of individual tissue/biofluids were then combined into cortex, CSF, or serum datasets for ranking. Finally, the three ranks were integrated into a final integrated rank (FIG. 7A). SMOC1 and tau proteins were ranked the top 2 of the list. Other proteins such as GFAP, NTN1, OLFM3, NPTX2, APP, MDK, C1QTNF5, C4B, and SPP1 were also shown to be important proteins. Moreover, a number of mitochondrial proteins were ranked high in the list as well (e.g. SUCLG2, PRDX3, CPT2, HSD17B10, ALDH6A1, GATM, and SOD2) (FIG. 7*b*). signaling pathways were prioritized by GSEA and identified 10 major pathways (FDR <0.05; FIG. 7C) out of the 16 core pathways detected in the deep AD cortex study (Bai, B., et al., Neuron. (2020)). Collectively these 10 pathways can be classified into 4 major categories including mitochondrial functions, inflammation, amyloid and tau pathway, and synaptic function. Finally, two alternative validation assays were performed to confirm the MS discoveries. ELISA assay was used to analyze the CSF samples of 7 healthy controls and 7 AD cases, confirming an increase of the candidate biomarker GPNMB in the AD samples (FIGS. 8A and 8*b*). Due to the limitation of available ELISA kits, the TOMAHAQ-based targeted MS assay was also implemented to validate the change of two mitochondrial proteins (AK2 and PCK2) in the CSF samples. In this TOMAHAQ assay, tryptic peptides in AK2 and PCK2 were synthesized as internal standards to guide the quantification of native corresponding peptides (FIG. 8C). Consistently, both mitochondrial proteins were confirmed to be reduced in the CSF AD samples (FIGS. 8D-8F). Together, a list of promising AD signatures was prioritized through a systems biology approach and provided a foundation for large-scale biomarker validation studies for the AD community.

Example 7: Multi-Omics Integration of Serum Samples with a Brain Tissue Data Set and a CSF Dataset Discovers Consistent AD Serum Biomarkers Serum samples from two independent cohorts, i.e., a Banner Sun cohort (n=45, AD: 24, Control: 21; see Table 2), and a PrecisionMed cohort (n=16, AD: 6, MCI (mild cognitive impairment): 5, Control: 5; see Table 3) were analyzed by TMT-LC/LC-MS/MS mass spectrometry.

TABLE 2

| Disease Diagnosis | Gender (1 = Male; 2 = Female) | Age | Postmortem Interval | Sample |
|---|---|---|---|---|
| AD | 2 | 96 | 2.75 | Serum |
| AD | 2 | 86 | 1.83 | Serum |
| AD | 1 | 76 | 4 | Serum |
| AD | 1 | 78 | 2.25 | Serum |
| AD | 2 | 84 | 2.53 | Serum |
| AD | 2 | 76 | 3.08 | Serum |
| AD | 2 | 92 | 3.73 | Serum |
| AD | 2 | 81 | 3.85 | Serum |
| AD | 1 | 83 | 3.58 | Serum |
| AD | 1 | 88 | 2.38 | Serum |
| AD | 1 | 81 | 3.08 | Serum |
| AD | 1 | 83 | 2.8 | Serum |
| AD | 1 | 81 | 1.75 | Serum |
| AD | 2 | 74 | 2 | Serum |
| AD | 2 | 79 | 1.5 | Serum |
| AD | 1 | 85 | 3 | Serum |
| AD | 1 | 86 | 3.16 | Serum |
| AD | 2 | 75 | 2.83 | Serum |
| AD | 2 | 75 | 2.75 | Serum |
| AD | 2 | 57 | 2.16 | Serum |
| AD | 1 | 86 | 2.3 | Serum |
| AD | 2 | 85 | 2.66 | Serum |
| AD | 1 | 82 | 2.95 | Serum |
| AD | 1 | 78 | 1.83 | Serum |
| AD | NA | NA | 3 | Serum |
| Non-AD Control | 2 | 90 | 3 | Serum |
| Non-AD Control | 2 | 80 | 2 | Serum |
| Non-AD Control | 1 | 86 | 2.8 | Serum |
| Non-AD Control | 1 | 86 | 2.75 | Serum |
| Non-AD Control | 2 | 83 | 3.25 | Serum |
| Non-AD Control | 2 | 88 | 4.5 | Serum |
| Non-AD Control | 1 | 84 | 4.25 | Serum |
| Non-AD Control | 1 | 89 | 3.33 | Serum |

TABLE 2-continued

| Disease Diagnosis | Gender (1 = Male; 2 = Female) | Age | Postmortem Interval | Sample |
|---|---|---|---|---|
| Non-AD Control | 1 | 97 | 1.87 | Serum |
| Non-AD Control | 2 | 99 | 3.5 | Serum |
| Non-AD Control | 1 | 87 | 3.55 | Serum |
| Non-AD Control | 2 | 82 | 2.07 | Serum |
| Non-AD Control | 2 | 87 | 2.02 | Serum |
| Non-AD Control | 1 | 86 | 2.5 | Serum |
| Non-AD Control | 2 | 87 | 2.5 | Serum |
| Non-AD Control | 1 | 92 | 3 | Serum |
| Non-AD Control | 1 | 86 | 3 | Serum |
| Non-AD Control | 1 | 80 | 2.16 | Serum |
| Non-AD Control | 1 | 91 | 3.33 | Serum |
| Non-AD Control | 1 | 61 | 2.33 | Serum |

TABLE 3

| Disease Diagnosis | Gender (1 = Male; 2 = Female) | Age | Sample Type | Sample |
|---|---|---|---|---|
| Non-AD Control | 1 | 56 | Fresh | Serum |
| Non-AD Control | 1 | 63 | Fresh | Serum |
| Non-AD Control | 1 | 55 | Fresh | Serum |
| Non-AD Control | 1 | 57 | Fresh | Serum |
| Non-AD Control | 1 | 62 | Fresh | Serum |
| AD | 2 | 63 | Fresh | Serum |
| AD | 1 | 51 | Fresh | Serum |
| AD | 1 | 55 | Fresh | Serum |
| AD | 1 | 76 | Fresh | Serum |
| AD | 1 | 55 | Fresh | Serum |
| AD | 1 | 51 | Fresh | Serum |
| MCI | 1 | 66 | Fresh | Serum |
| MCI | 1 | 73 | Fresh | Serum |
| MCI | 2 | 74 | Fresh | Serum |
| MCI | 2 | 75 | Fresh | Serum |
| MCI | 2 | 70 | Fresh | Serum |

The serum dataset was subsequently integrated with a brain cortex tissue dataset (n=192, AD: 106, Control: 86; (dataset extracted from: Bai B, et al., Neuron 2020, 105: 975-991.; Higginbotham L, et al., Sci Adv 2020, 6:eaaz9360; Wang Z, Yu K W, Tan H, Wu Z, Cho J H, Han X, Sun H, Beach T G, Peng J M: 27-plex Tandem Mass Tag Mass Spectrometry for Profiling Brain Proteome in Alzheimer's Disease. Anal Chem 2020: [Epub ahead of print]; and Sathe G, et al., J Neurochem 2020) and a CSF dataset (n=260, AD: 121, Control: 139; (dataset extracted from Bai B, et al., Neuron 2020, 105:975-991.; Higginbotham L, et al., Sci Adv 2020, 6:eaaz9360; Sathe G, et al., Proteomics Clin Appl 2019, 13:e1800105.; Bader J M, et al., Mol Syst Biol 2020, 16:e9356; and Wang H et al., Mol Neurodegener 2020, 15:43). The analysis was performed in the following steps:

Step1: Define consistent AD serum biomarker using multi-omics integration (Bai B, et al., Neuron 2020, 105: 975-991):

1. Category A: top changed serum proteins with FDR <0.05: n=7.
2. Category B: proteins changed in serum (P<0.05), CSF (BH FDR <0.05), Brain cortex tissue (BH FDR <0.05); consistent change of directions: n=4.
3. Category C: protein highly changed in serum (log FC (fold change)>2SD (standard deviation), P<0.05) and brain cortex tissue (log FC >2SD, BH FDR <0.05), consistent change of direction: n=15.
4. Category D: protein highly changed in serum (log FC >2SD, P<0.05) and CSF (log FC >2SD, BH FDR <0.05), consistent change of direction: n=9.
5. Category E: protein changed in serum samples of Banner Sun cohort (log FC >2SD, P<0.05) and serum samples of PrecisionMed cohort (log FC >2SD, P<0.05), consistent change of direction: n=2

The foregoing Step 1 analysis resulted in the identification of 37 candidate proteins.

Step 2: Prioritize the 37 candidate proteins in Step 1 by cell of origin, subcellular localization, and GWAS risk factor.

Brain cell origin with enriched expression in brain tissues: n=6

Protein with subcellular location of mitochondria: n=5

Known AD risk genes: n=1

Step 2 prioritization reduced the biomarker list from 37 to 12 proteins (i.e., NPTX2, OLFM1, NGEF, DGKG, SLC6A1, GRIN1, APOC2, SDHA, ECI1, HSPA9, ETFB, and MYL3; FIG. 9).

In addition, this analysis identified the following candidate biomarkers as top changed proteins in brain cortex tissue (n=12) and CSF (n=12), although they were not detected in serum: the top 12 proteins in brain cortex tissue: MAPT, SMOC1, VGF, GPNMB, RPH3A, HSPB1, MDK, CD109, ICAM1, CTHRC1, NTN1, and APP (Aβ); and the top 12 proteins in CSF: CHI3L1, ENO2, SOD1, MDH1, PGAM1, LDHA, GOT1, GDA, YWHAZ, ALDOA, YWHAG, and PKM (FIG. 9).

The invention claimed is:

1. A method of treating Alzheimer's disease in a subject, said method comprising:

a) detecting an increased level or a decreased level of at least three signature proteins selected from the group consisting of SUCLG2, NTN1, CIQTNF5, OLFML3, SLIT2, SPON1, GPNMB, SOD2, PRDX3, ALDH6A1, ETFB, HADHA, CYB5R3, CTHRC1, OLFM3, SMOC1, NPTX2, OLFM1, NGEF, DGKG, SLC6A1, GRIN1, APOC2, SDHA, ECI1, HSPA9, and MYL3 in a biological sample from the subject compared to the level of the corresponding signature protein in the control sample, wherein the increased level or the decreased level of the at least three signature proteins in the biological sample relative to the level of the corresponding signature protein from the control sample indicates that the subject has or is at risk of developing Alzheimer's disease, or indicates a progression of Alzheimer's disease in the subject, and b) administering to the subject an Alzheimer's disease treatment regimen that is designed configured to modulate increase or decrease the level of at least one of the at least three signature proteins, based upon the level of the at least three signature proteins detected in step a).

2. The method of claim 1, wherein the at least three signature proteins are selected from one or more of ALDH6A1, ETFB, SOD2, PRDX3, CTHRC1, OLFM3, NPTX2, OLFM1, NGEF, DGKG, SLC6A1, GRIN1, APOC2, SDHA, ECI1, HSPA9, and MYL3.

3. The method of claim 1, wherein the level of at least two signature proteins, at least three signature proteins, at least four signature proteins, at least five signature proteins, at least six signature proteins, at least seven signature proteins, at least eight signature proteins, at least nine signature proteins, at least ten signature proteins, or at least eleven signature proteins is increased, and wherein the increased level indicates the subject has or is at risk of developing Alzheimer's disease or indicates a progression of Alzheimer's disease in said subject.

4. The method of claim 3, wherein the level of at least one-two signature proteins selected from the group consisting of SLIT2, SPON1, GPNMB, C1QTNF5, OLFML3, SMOC1, SUCLG2, PRDX3, and NTN1 is increased.

5. The method of claim 1, wherein the level of at least two signature proteins, at least three signature proteins, at least four signature proteins, at least five signature proteins, at least six signature proteins, at least seven signature proteins, at least eight signature proteins, or at least nine signature proteins is decreased, and wherein the decreased level indicates the subject has or is at risk of developing Alzheimer's disease or indicates a progression of Alzheimer's disease in said subject.

6. The method of claim 5, wherein the level of at least ene-two signature proteins selected from the group consisting of SOD2, PRDX3, ALDH6A1, ETFB, HADHA, CYB5R3, CTHRC1, and OLFM3 is decreased.

7. The method of claim 1, wherein said biological sample comprises a blood sample, a serum sample, a plasma sample, a lymph sample, a urine sample, a saliva sample, a tear sample, a sweat sample, a semen sample, a vaginal sample, a bronchial sample, a mucosal sample, a cerebrospinal fluid (CSF) sample, or brain microdialysate.

8. The method of claim 1, wherein the level of said at least three signature proteins are measured or detected using an immunoassay, a western blot analysis, mass spectrometry, tandem mass (MS/MS) spectrometry, multiplexed tandem mass-tag, liquid chromatography (LC) fractionation, TOMAHAQ, a TMT-LC/LC/MS/MS platform, or an ultra-deep proteomic platform.

9. The method of claim 1, wherein the at least three signature proteins further comprise GFAP or TAU.

10. The method of claim 3, wherein the level of at least three signature proteins, at least four signature proteins, at least five signature proteins, at least six signature proteins, at least seven signature proteins, at least eight signature proteins, at least nine signature proteins, at least ten signature proteins, at least eleven signature proteins, at least twelve signature proteins, at least thirteen signature proteins, at least fourteen signature proteins, at least fifteen signature proteins, at least sixteen signature proteins, or at least seventeen signature proteins is increased, and wherein the increased level indicates the subject has or is at risk of developing Alzheimer's disease or indicates a progression of Alzheimer's disease in said subject.

11. The method of claim 10, wherein the level of at least three signature proteins selected from the group consisting of SLIT2, SPON1, GPNMB, C1QTNF5, OLFML3, SMOC1, TAU, GFAP, SUCLG2, PRDX3, and NTN1 is increased.

12. The method of claim 5, wherein the level of at least three signature proteins, at least four signature proteins, at least five signature proteins, at least six signature proteins, at least seven signature proteins, at least eight signature proteins, or at least nine signature proteins is decreased, and wherein the decreased level indicates the subject has or is at risk of developing Alzheimer's disease or indicates a progression of Alzheimer's disease in said subject.

13. The method of claim 12, wherein the level of at least three signature proteins selected from the group consisting of SOD2, PRDX3, ALDH6A1, ETFB, HADHA, CYB5R3, CTHRC1, GFAP and OLFM3 is decreased.

14. The method of claim 7, wherein said biological sample comprises a serum sample, a cerebrospinal fluid (CSF) sample, or brain microdialysate.

15. The method of claim 1, wherein the treating comprises administering to the subject a therapeutically effective amount of an antagonist/agonist of SUCLG2, an antagonist/agonist of NTN1, an antagonist/agonist of C1QTNF5, an antagonist/agonist of OLFML3, an antagonist/agonist of SLIT2, an antagonist/agonist of SPON1, an antagonist/agonist of GPNMB, an antagonist/agonist of SOD2, an antagonist/agonist of PRDX3, an antagonist/agonist of ALDH6A1, an antagonist/agonist of ETFB, an antagonist/agonist of HADHA, an antagonist/agonist of CYB5R3, an antagonist/agonist of CTHRC1, an antagonist/agonist of OLFM3, an antagonist/agonist of SMOC1, an antagonist/agonist of TAU, an antagonist/agonist of GFAP, an antagonist/agonist of NPTX2, an antagonist/agonist of OLFM1, an antagonist/agonist of NGEF, an antagonist/agonist of DGKG, an antagonist/agonist of SLC6A1, an antagonist/agonist of GRIN1, an antagonist/agonist of APOC2, an antagonist/agonist of SDHA, an antagonist/agonist of ECI1, an antagonist/agonist of HSPA9, and an antagonist/agonist of MYL3, or any combination thereof.

16. A composition comprising one or more reagents for assaying for the level of signature proteins in a sample of a subject, wherein the signature proteins comprise (i) at least six signature proteins selected from the group consisting of ETFB, NPTX2, OLFM1, NGEF, DGKG, SLC6A1, GRIN1, APOC2, SDHA, ECI1, HSPA9, and MYL3, or fragments or variants thereof;

(ii) at least six signature proteins selected from the group consisting of MAPT, SMOC1, VGF, GPNMB, RPH3A, HSPB1, MDK, CD109, ICAM1, CTHRC1, NTN1, and APP (Aβ) or fragments or variants thereof; or iii) at least six signature proteins selected from the group consisting of CHI3L1, ENO2, SOD1, MDH1, PGAM1, LDHA, GOT1, GDA, YWHAZ, ALDOA, YWHAG, and PKM or fragments or variants thereof.

17. The composition of claim 16, wherein the signature proteins comprise (i) ETFB, NPTX2, OLFM1, NGEF, DGKG, SLC6A1, GRIN1, APOC2, SDHA, ECI1, HSPA9, and MYL3, or fragments or variants thereof;

(ii) MAPT, SMOC1, VGF, GPNMB, RPH3A, HSPB1, MDK, CD109, ICAM1, CTHRC1, NTN1, and APP (Aβ) or fragments or variants thereof; or iii) CHI3L1, ENO2, SOD1, MDH1, PGAM1, LDHA, GOT1, GDA, YWHAZ, ALDOA, YWHAG, and PKM or fragments or variants thereof.

18. A method of treating Alzheimer's disease in a subject, said method comprising:

a) detecting an increased level or a decreased level of at least one three signature proteins selected from SUCLG2, NTN1, CIQTNF5, OLFML3, SLIT2, SPON1, GPNMB, SOD2, PRDX3, ALDH6A1, ETFB, HADHA, CYB5R3, CTHRC1, OLFM3, SMOC1, NPTX2, OLFM1, NGEF, DGKG, SLC6A1, GRIN1, APOC2, SDHA, ECI1, HSPA9, and MYL3 in a biological sample from the subject, wherein i) the level of two or more of SLIT2, SPON1, GPNMB, CIQTNF5, OLFML3, SMOC1, SUCLG2, PRDX3, NTN1, NPTX2, OLFM1, NGEF, DGKG, SLC6A1, GRIN1, APOC2, SDHA, ECI1, HSPA9, and MYL3 is increased, or ii) the level of two or more of SOD2, PRDX3, ALDH6A1, ETFB, HADHA, CYB5R3, CTHRC1, GFAP, OLFM3, NPTX2, OLFM1, NGEF, DGKG, SLC6A1, GRIN1, APOC2, SDHA, ECI1, HSPA9, and MYL3 is decreased, in the biological sample compared to the level of the corresponding signature protein in a control sample, wherein the increased level or the decreased level of the at least one signature protein in the biological sample relative to the level of the corresponding signature protein from the control sample indicates that the subject has or is at risk of developing Alzheimer's disease, or indicates a progression of Alzheimer's disease in the subject, and b) administering to the subject an Alzheimer's disease treatment regimen that reduces the level of at least one of the at least three signature proteins having an increased level or increases the level of at least one of the at least three signature proteins having a decreased level, based upon the level of the at least three signature proteins detected in step a).

19. The method of claim 18, further comprising detecting an increased or decreased level of GFAP, and/or an increased level of TAU.

20. The method of claim 18, wherein the treating comprises administering to the subject a therapeutically effective amount of an agent, wherein the agent is an antagonist/agonist of SUCLG2, an antagonist/agonist of NTN1, an antagonist/agonist of C1QTNF5, an antagonist/agonist of OLFML3, an antagonist/agonist of SLIT2, an antagonist/agonist of SPON1, an antagonist/agonist of GPNMB, an antagonist/agonist of SOD2, an antagonist/agonist of PRDX3, an antagonist/agonist of ALDH6A1, an antagonist/agonist of ETFB, an antagonist/agonist of HADHA, an antagonist/agonist of CYB5R3, an antagonist/agonist of CTHRC1, an antagonist/agonist of OLFM3, an antagonist/agonist of SMOC1, an antagonist/agonist of TAU, an antagonist/agonist of GFAP, an antagonist/agonist of NPTX2, an antagonist/agonist of OLFM1, an antagonist/agonist of NGEF, an antagonist/agonist of DGKG, an antagonist/agonist of SLC6A1, an antagonist/agonist of GRIN1, an antagonist/agonist of APOC2, an antagonist/agonist of SDHA, an antagonist/agonist of ECI1, an antagonist/agonist of HSPA9, and an antagonist/agonist of MYL3, or any combination thereof, and wherein the agent decreases the activity of the at least one signature protein having the increased level, or increases the activity of the at least one signature protein having the decreased level, in the subject.

* * * * *